United States Patent
Potarine Juhasz et al.

(10) Patent No.: US 11,001,582 B2
(45) Date of Patent: May 11, 2021

(54) SOLID STATE FORMS OF VENETOCLAX AND PROCESSES FOR PREPARATION OF VENETOCLAX

(71) Applicant: ASSIA CHEMICAL INDUSTRIES LTD., Petach Tikva (IL)

(72) Inventors: Zsuzsa Potarine Juhasz, Debrecen (HU); Szabolcs Struba, Balmazujvaros (HU); Csilla Nemethne Racz, Debrecen (HU); Zoltan Gabor Toth, Debrecen (HU); Andrea Szilagyi, Debrecen (HU); Renata Kerti-Ferenczi, Hajdusamson-Samsonkert (HU); Sandor Janos Molnar, Debrecen (HU); Nora Pasztor-Debreczeni, Debrecen (HU); Janos Hajko, Debrecen (HU)

(73) Assignee: ASSIA CHEMICAL INDUSTRIES LTD., Petach Tikva (IL)

( * ) Notice: Subject to any disclaimer, the term of this patent is extended or adjusted under 35 U.S.C. 154(b) by 0 days.

(21) Appl. No.: 16/083,693

(22) PCT Filed: Mar. 10, 2017

(86) PCT No.: PCT/US2017/021785
§ 371 (c)(1),
(2) Date: Sep. 10, 2018

(87) PCT Pub. No.: WO2017/156398
PCT Pub. Date: Sep. 14, 2017

(65) Prior Publication Data
US 2019/0135806 A1 May 9, 2019

Related U.S. Application Data

(60) Provisional application No. 62/380,715, filed on Aug. 29, 2016, provisional application No. 62/493,761, filed on Jul. 13, 2016, provisional application No. 62/321,416, filed on Apr. 12, 2016, provisional application No. 62/306,314, filed on Mar. 10, 2016.

(51) Int. Cl.
C07D 471/04 (2006.01)

(52) U.S. Cl.
CPC ........ C07D 471/04 (2013.01); C07B 2200/13 (2013.01)

(58) Field of Classification Search
CPC .................................................. C07D 471/04
See application file for complete search history.

(56) References Cited

U.S. PATENT DOCUMENTS

| | | | |
|---|---|---|---|
| 5,006,549 A | * | 4/1991 | Zambias .............. C07D 307/79 514/337 |
| 8,546,399 B2 | | 10/2013 | Bruncko et al. |
| 2006/0074102 A1 | * | 4/2006 | Cusack .............. A61K 31/4743 514/301 |
| 2009/0306083 A1 | * | 12/2009 | Sivasankaran ....... A61K 31/428 514/248 |
| 2011/0230457 A1 | * | 9/2011 | Berghausen ......... C07D 217/24 514/210.02 |
| 2014/0275540 A1 | * | 9/2014 | Chan ................... C07D 471/04 544/362 |
| 2018/0354950 A1 | * | 12/2018 | Wang .................. C07D 471/04 |

FOREIGN PATENT DOCUMENTS

| | | |
|---|---|---|
| WO | 2010138588 A2 | 5/2010 |
| WO | 2012058392 A1 | 5/2012 |
| WO | 2012071336 A1 | 5/2012 |
| WO | 2012121758 A1 | 9/2012 |
| WO | 2014165044 A1 | 10/2014 |
| WO | 2017063572 A1 | 4/2017 |
| WO | 2017212431 A1 | 12/2017 |
| WO | 2018029711 A1 | 2/2018 |
| WO | 2018069941 A2 | 4/2018 |

OTHER PUBLICATIONS

Priority Document IN 201641022742 filed Jul. 1, 2016 for WO 2017-212431.*
Caira, Mino R.; "Crystalline Polymorphism of Organic Compounds"; Topics in Current Chemistry, vol. 198: 1998; pp. 163-208.
International Search Report for International Application No. PCT/US2017/021785, International Filing Date Mar. 10, 2017, dated Jun. 19, 2017, 8 pages.
Written Opinion for International Application No. PCT/US2017/021785, International Filing Date Mar. 10, 2017, dated Jun. 19, 2017, 12 pages.
Hughes, David L.; "Patent Review of Manufacturing Routes to Oncology Drugs: Carfilzomib, Osimertinib, and Venetoclax"; Organic Process Research & Development; vol. 20; 2016: pp. 2028-2042.
Park, Cheol-Min et al.; "Discovery of an Orally Bioavailable Small Molecule Inhibitor of Prosurvival B-Cell Lymphoma 2 Proteins"; J. Med. Chem., vol. 51; 2008: pp. 6902-6915.
Sleebs, Brad E. et al.; "Quinazoline Sulfonamides as Dual Binders of the Proteins B-Cell Lymphoma 2 and B-Cell Lymphoma Extra Long with Potent Proapoptotic Cell-Based Activity"; Journal of Medicinal Chemistry, vol. 54; 2011: pp. 1914-1926.

(Continued)

Primary Examiner — Emily A Bernhardt
(74) Attorney, Agent, or Firm — Cantor Colburn LLP

(57) ABSTRACT

Processes for the preparation of Venetoclax and Venetoclax produced by the processes are disclosed. Intermediate compounds used in the processes are further disclosed including the compound of formula 5

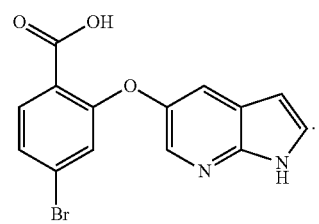

31 Claims, 24 Drawing Sheets

(56) References Cited

OTHER PUBLICATIONS

Ku, Yi-Yin et al.; "Development of a Convergent Large-Scale Synthesis for Venetoclax, a First-in-Class BCL-2 Selective Inhibitor"; The Journal of Organic Chemistry; 84, 2019, p. 4814-4829.

* cited by examiner

SOLID STATE FORMS OF VENETOCLAX AND PROCESSES FOR PREPARATION OF VENETOCLAX

CROSS-REFERENCE TO RELATED APPLICATIONS

This application is a U.S. National Stage application of International Application No. PCT/US17/21785, filed Mar. 10, 2017, which claims the benefit of U.S. Provisional Application No. 62/306,314, filed Mar. 10, 2016, U.S. Provisional Application No. 62/321,416, filed Apr. 12, 2016, U.S. Provisional Application No. 62/493,761, filed Jul. 13, 2016, U.S. Provisional Application No. 62/380,715, filed Aug. 29, 2016, each of which is incorporated herein in its entirety.

FIELD OF THE DISCLOSURE

The present disclosure encompasses solid state forms of Venetoclax and pharmaceutical compositions thereof and processes for preparation of Venetoclax.

BACKGROUND OF THE DISCLOSURE

Venetoclax, 4-(4-{[2-(4-chlorophenyl)-4,4-dimethyl-cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, has the following chemical structure:

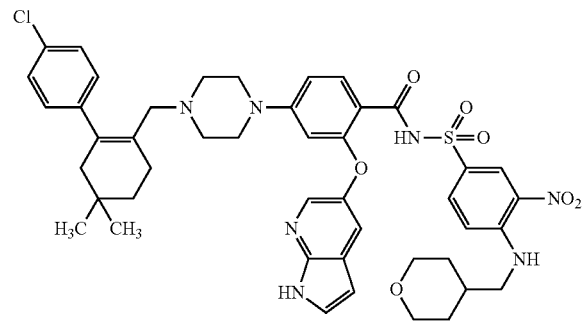 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

Compound 1

Venetoclax is described in U.S. Pat. No. 8,546,399. Solid state forms of Venetoclax and of the HCl salt and sulfate salt thereof are described in WO 2012/071336. WO 2012/121758 and WO 2012/058392 describe solid dispersions comprising Venetoclax.

Polymorphism, the occurrence of different crystalline forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, and solid state ($^{13}$C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Venetoclax.

Use of solvates as starting material for preparation of the final dosage form requires monitoring the residual solvent content in the final dosage form. Further, the known synthetic processes have several drawbacks such as lower overall yield, use of column chromatography and use of toxic and costly solvents. For at least these reasons, there is a need to develop robust, high yield and plant friendly processes for preparation of Venetoclax that afford non solvated stable forms or solvated stable forms that can be easily converted to other crystalline forms that do not contain residual solvents, amorphous or premix that can be used directly for formulation.

SUMMARY OF THE DISCLOSURE

The present disclosure provides solid state forms of Venetoclax, processes for preparation thereof, and pharmaceutical compositions thereof. These solid state forms can be used to prepare other solid state forms of Venetoclax, Venetoclax salts and solid state forms thereof.

The present disclosure provides solid state forms of venetoclax for use in the preparation of pharmaceutical compositions comprising venetoclax.

The present disclosure also encompasses the use of the venetoclax solid state forms of the present disclosure for the preparation of pharmaceutical compositions of venetoclax.

The present disclosure comprises processes for preparing the above mentioned pharmaceutical compositions. The processes comprise combining the Venetoclax solid state forms with at least one pharmaceutically acceptable excipient.

The solid state forms and the pharmaceutical compositions of Venetoclax of the present disclosure can be used as medicaments, particularly for the treatment of chronic lymphocytic leukemia.

The present disclosure also provides methods of chronic lymphocytic leukemia comprising administering a therapeutically effective amount of a venetoclax solid state form of the present disclosure, or at least one of the above pharmaceutical compositions, to a subject in need of the treatment.

The present disclosure also provides processes for preparation of venetoclax and provides a novel intermediate that can be advantageously used for the preparation of venetoclax.

DETAILED DESCRIPTION OF THE DISCLOSURE

Figure 1:
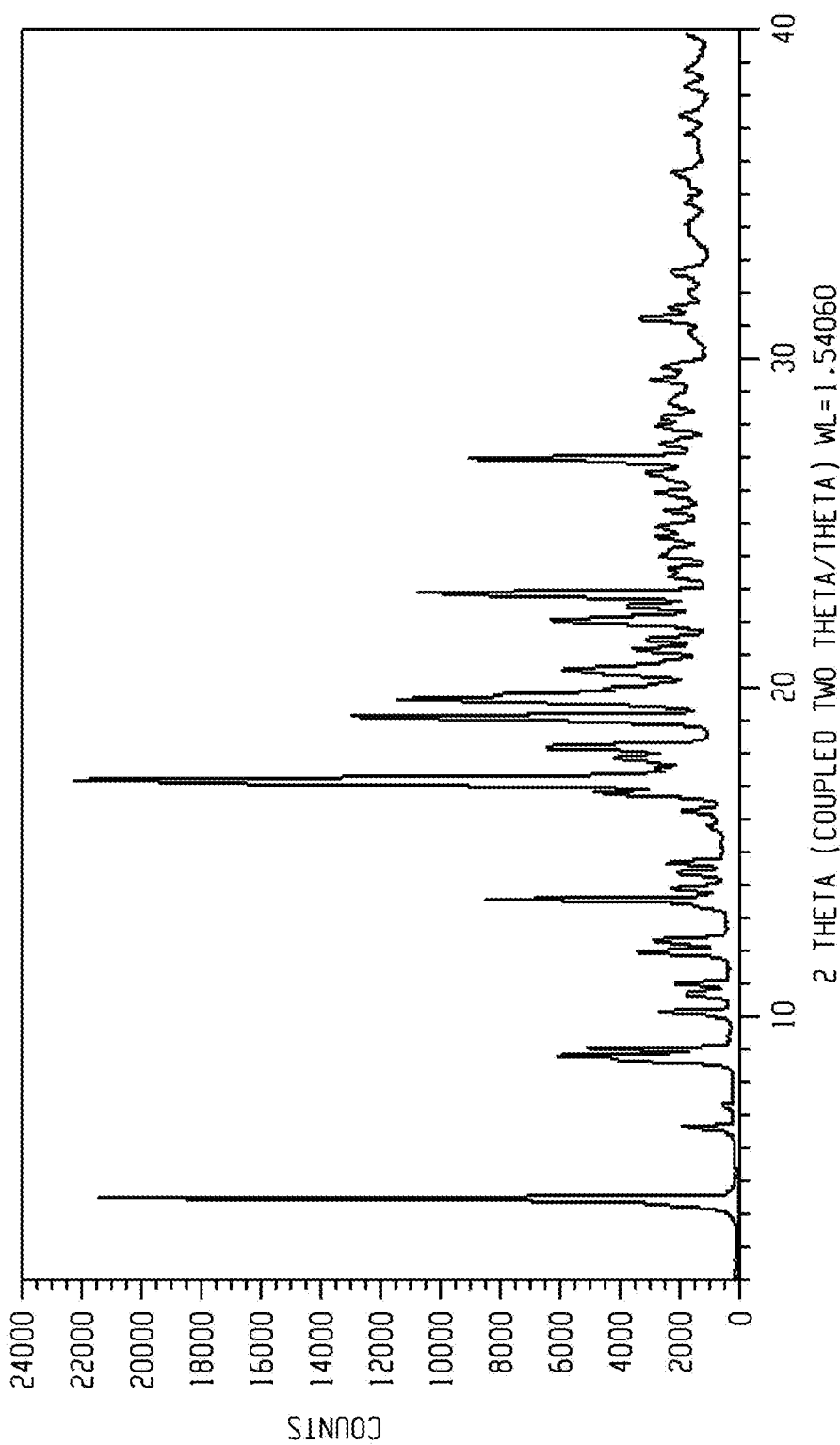
FIG. 1 shows a characteristic X-ray powder diffraction pattern of form 1 of Venetoclax.

The present disclosure encompasses solid state forms of Venetoclax. Solid state properties of Venetoclax can be influenced by controlling the conditions under which the Venetoclax is obtained in solid form.

The present disclosure further encompasses novel processes for preparation of Venetoclax.

The processes described in the literature have significant disadvantages. WO 2010/138588, discloses a process having a low overall yield (32%), and requiring the use of column chromatography for purification in several steps. The process also uses toxic and costly solvents such as diglyme which is a strong teratogen and 1,4-dioxane.

An alternative approach is disclosed in WO 2014/165044. A key step in both processes is the preparation of either Methyl 4-fluoro-2-(1H-pyrrolo[2,3-b]pyridine-5-yloxy)benzoate from methyl 2,4,-difluorobenzoate or tert-Butyl 4-bromo-2-(1H-pyrrolo[2,3-b]pyridine-5-yloxy)benzoate from tert-Butyl 2-fluoro-4-bromo benzoate. Replication of the WO 2010/138588 process for preparation of Methyl 4-fluoro-2-(1H-pyrrolo[2,3-b]pyridine-5-yloxy)benzoate by the applicant of the present disclosure proved the formation of a regioisomer which is very difficult to remove. Moreover, the disclosure in WO 2010/138588 involves use of diglyme which is a teratogenic solvent. Preparation of tert-Butyl 4-bromo-2-(1H-pyrrolo[2,3-b]pyridine-5-yloxy) benzoate involves use of Sodium tert-butoxide salt which is an expensive and sensitive base that requires handling under inert gas atmosphere and decomposes in contact with humidity. Further, in both processes the previously mentioned intermediates are coupled with 1-[[2-(4-Chlorophenyl)-4,4-dimethylcyclohex-1-enyl]methyl]piperazine to afford methyl 2-[(1H-Pyrrolo[2,3-b]pyridine-5-yl)oxy]-4-[4-[[2-(4-chlorophenyl)-4,4-dimethylcyclohex-1-enyl] methyl]piperazin-1-yl]benzoate or tert-butyl 2-[(1H-Pyrrolo[2,3-b] pyridine-5-yl)oxy]-4-[4-[[2-(4-chlorophenyl)-4,4-dimethylcyclohex-1-enyl]methyl]piperazin-1-yl]benzoate, respectively, both of which are isolated and then undergo hydrolysis in a separate step to afford 2-[(1H-Pyrrolo[2,3-b]pyridine-5-yl)oxy]-4-[4-[[2-(4-chlorophenyl)-4,4-dimethylcyclohex-1-enyl]methyl]piperazin-1-yl]benzoic acid.

In contrast to the prior art processes, in the processes of the present disclosure the starting material of the present disclosure, methyl 4 bromo-2-fluorobenzoate is cheaper than the tert-Butyl 4 bromo-2-fluorobenzoate known from the literature and offers a regioselective reaction. Further, $K_3PO_4$ and NaOH, which are cheaper and non-sensitive bases are used in preparation of the novel intermediate, 4-Bromo-2-(1H-pyrrolo[2,3-b]pyridine-5-yloxy)benzoic acid. This process allows direct isolation of 4-Bromo-2-(1H-pyrrolo[2,3-b]pyridine-5-yloxy)benzoic acid and the reaction to proceed in near quantitative yields. The reaction of the novel intermediate, 4-Bromo-2-(1H-pyrrolo[2,3-b]6yridine-5-yloxy)benzoic acid with 1-[[2-(4-Chlorophenyl)-4,4-dimethylcyclohex-1-enyl]methyl]piperazine in performed in the presence of LiHMDS (lithium bis(trimethylsilyl)amide, or lithium hexamethyldisilazide, $LiN(SiMe_3)_2$) which provides for shorter reaction times. Therefore, the processes of the present disclosure avoid use of hazardous or non-economical reagents and solvents, involve less steps and therefore can be adapted to production in an industrial scale, i.e., greater than 1 kilogram scale.

In some embodiments, the crystalline forms of Venetoclax of the disclosure are substantially free of any other forms of Venetoclax, or of specified polymorphic forms of Venetoclax, respectively.

As used herein, "substantially free" is meant that the solid state forms of the present disclosure contain about 20% (w/w) or less of polymorphs, or of a specified polymorph of Venetoclax. According to some embodiments, the solid state forms of the present disclosure contain about 10% (w/w) or less, about 5% (w/w) or less, about 2% (w/w) or less, about 1% (w/w) or less, about 0.5% (w/w) or less, or about 0.2% (w/w) or less of polymorphs, or of a specified polymorph of Venetoclax. In other embodiments, solid state forms of Venetoclax of the present disclosure contain from about 1% to about 20% (w/w), from about 5% to about 20% (w/w), or from about 5% to about 10% (w/w) of any solid state forms or of a specified polymorph of Venetoclax.

A solid state form (or polymorph) may be referred to herein as polymorphically pure or as substantially free of any other solid state (or polymorphic) forms. As used herein in this context, the expression "substantially free of any other forms" will be understood to mean that the solid state form contains 20% or less, 10% or less, 5% or less, 2% or less, or 1% or less of any other forms of the subject compound as measured, for example, by PXRD. Thus, solid state of Venetoclax described herein as substantially free of any other solid state forms would be understood to contain greater than 80% (w/w), greater than 90% (w/w), greater than 95% (w/w), greater than 98% (w/w), or greater than 99% (w/w) of the subject solid state form of Venetoclax. Accordingly, in some embodiments of the invention, the described solid state forms of Venetoclax may contain from 1% to 20% (w/w), from 5% to 20% (w/w), or from 5% to 10% (w/w) of one or more other solid state forms of the same Venetoclax.

Depending on the other solid state forms to which comparison is made, the crystalline forms of Venetoclax of the present disclosure have advantageous properties selected from at least one of the following: chemical purity, flowability, solubility, dissolution rate, morphology or crystal habit, stability (such as chemical stability as well as thermal and mechanical stability with respect to polymorphic conversion, stability towards dehydration and/or storage stability), low content of residual solvent, a lower degree of hygroscopicity, flowability, and advantageous processing and handling characteristics such as compressibility, and bulk density.

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Venetoclax referred to herein as being characterized by graphical data "as depicted in" or "as substantially depicted in" a Figure will thus be understood to include any crystal forms of Venetoclax characterized with the graphical data having such small variations, as are well known to the skilled person, in comparison with the Figure.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9-1.1.

As used herein, and unless stated otherwise, the term "anhydrous" in relation to crystalline forms of Venetoclax, relates to a crystalline form of Venetoclax which does not include any crystalline water (or other solvents) in a defined, stoichiometric amount within the crystal. Moreover, an "anhydrous" form would typically not contain more than 1% (w/w) of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless indicated otherwise, the term "wet crystalline form" refers to a polymorph that was not dried using any conventional techniques to remove residual solvent. Examples for such conventional techniques can be, but not limited to, evaporation, vacuum drying, oven drying, drying under nitrogen flow etc.

As used herein, and unless indicated otherwise, the term "dry crystalline form" refers to a polymorph that was dried using any conventional techniques to remove residual solvent. Examples for such conventional techniques can be, but not limited to, evaporation, vacuum drying, oven drying, drying under nitrogen flow, etc.

As used herein, unless indicated otherwise, the term "elevated temperature" refers to any temperature above room temperature, preferably above about 20° C., and more preferably above about 25° C.

As used herein, the term "isolated" in reference to solid state forms of Venetoclax of the present disclosure corresponds to a solid state form of Venetoclax that is physically separated from the reaction mixture in which it is formed.

As used herein, unless stated otherwise, the XRPD measurements are taken using copper K$\alpha$ radiation wavelength 1.5418 Å.

As used herein, unless stated otherwise, chemical purity (area percent) may be measured by HPLC analysis. Preferably, the HPLC analysis is carried out using a reversed phase silica gel column (e.g. C18 column) using UV detection at suitable wavelength (e.g. 230 nm). Any suitable eluent can be used to carry out the separation (preferably a mixture of acetonitrile/water or methanol/water is used). Chemical purity may also be measured by wt %.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refers to atmospheric pressure, 22-24° C.

As used herein, and unless stated otherwise, the term Venetoclax Premix refers to a solid dispersion of Venetoclax with a pharmaceutically acceptable carrier, and optionally other pharmaceutically acceptable excipients. Such a solid dispersion can be a co-precipitate of Venetoclax with a pharmaceutically acceptable carrier, and optionally other pharmaceutically acceptable excipients. Such a co-precipitate may be prepared by mixing Venetoclax and a pharmaceutically acceptable carrier and optionally other pharmaceutically acceptable excipients in solvent(s) to form a mixture, and removing the solvent(s) from the mixture. The mixture may be a solution (e.g. wherein the components are dissolved), or a suspension or dispersion (e.g. wherein none of the components are dissolved but form a suspension or dispersion, or wherein some but not all of the components are dissolved). In a preferred embodiment according to any aspect of the present disclosure, the term Venetoclax Premix refers to a coprecipitate of Venetoclax with copovidone, and optionally other pharmaceutically acceptable excipients.

In a preferred embodiment, a co-precipitate of Venetoclax can be prepared by mixing Venetoclax and a pharmaceutically acceptable carrier and optionally other pharmaceutically acceptable excipients in solvent(s) to form a solution, and removing the solvent(s) from the solution.

In another preferred embodiment, a co-precipitate of Venetoclax can be prepared by mixing Venetoclax and a pharmaceutically acceptable carrier and optionally other pharmaceutically acceptable excipients in solvent(s) to form a mixture wherein the pharmaceutically acceptable carrier is dissolved and the Venetoclax is substantially undissolved, and removing the solvent(s) from the mixture.

In another preferred embodiment, a co-precipitate of Venetoclax can be prepared by mixing Venetoclax and a pharmaceutically acceptable carrier and optionally other pharmaceutically acceptable excipients in solvent(s) to form a mixture wherein both the Venetoclax and the pharmaceutically acceptable carrier form a suspension, and removing the solvent(s) from the mixture.

As used herein, and unless indicated otherwise, the term amorphous premix refers to a premix comprising substantially amorphous Venetoclax. In a preferred embodiment, an amorphous premix may be prepared dissolving Venetoclax and a pharmaceutically acceptable carrier and optionally other pharmaceutically acceptable excipients in solvent(s) to form a solution, and removing the solvent(s) from the solution.

As used herein, and unless indicated otherwise, the term crystalline premix refers to a premix comprising Venetoclax wherein the Venetoclax is in substantially crystalline form. In a preferred embodiment, a crystalline premix can be prepared by mixing Venetoclax and a pharmaceutically acceptable carrier and optionally other pharmaceutically acceptable excipients in solvent(s) to form a mixture wherein the pharmaceutically acceptable carrier is dissolved and wherein the Venetoclax is substantially undissolved, and removing the solvent(s) from the mixture.

As used herein, and unless indicated otherwise, the term "substantially amorphous" is intended to mean greater than about 70%; or greater than about 75%; or greater than about 80%; or greater than about 85%; or greater than about 90%; or greater than about 95%, or greater than about 99% of the compound present in a composition is in amorphous form.

As used herein, and unless state indicated otherwise, the term "substantially crystalline" is intended to mean that greater than about 70%; or greater than about 75%; or greater than about 80%; or greater than about 85%; or greater than about 90%; or greater than about 95%, or greater than about 99% of the compound is present in a composition is in crystalline form.

The present disclosure comprises a crystalline form of Venetoclax, designated form 1. The crystalline form 1 of Venetoclax may be characterized by data selected from one or more of the following: an X-ray powder diffraction pattern substantially as depicted in FIG. 1; an X-ray powder diffraction pattern having peaks at 4.5, 6.7, 10.2, 12.0 and 13.6 degrees two theta±0.2 degrees two theta; and combinations of these data.

Crystalline form 1 of Venetoclax may be further characterized by an X-ray powder diffraction pattern having peaks as described above and also having any one, two, three, four or five additional peaks selected from 12.3, 17.2, 19.2, 20.6 and 22.9 degrees two theta±0.2 degrees two theta.

Crystalline form 1 of Venetoclax may be characterized by each of the above characteristics alone/or by all possible combinations, e.g. an XRPD pattern having peaks at 12.3, 17.2, 19.2, 20.6 and 22.9 degrees two theta±0.2 degrees two theta; an XRPD pattern as depicted in FIG. 1.

In one embodiment of the present disclosure, form 1 of Venetoclax is isolated.

In another embodiment of the present disclosure, form 1 of Venetoclax is polymorphically pure.

In some embodiments, form 1 of Venetoclax may be a methyl-isobutyl ketone (MIBK) monosolvate. In certain embodiments, form 1 may contain from about 8.0% to about 12.0% of MIBK, specifically about 10.3% of MIBK.

Figure 18:
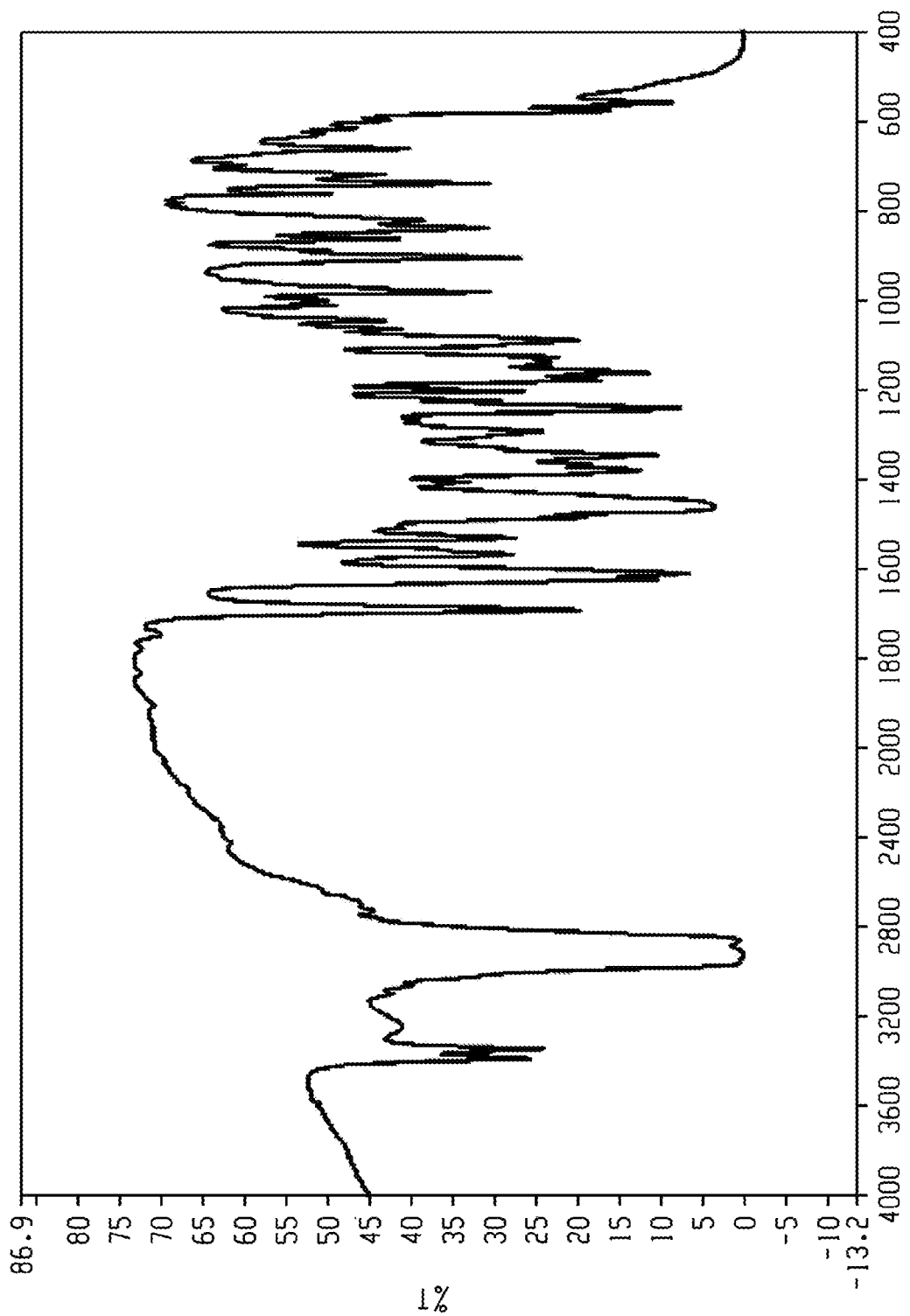
FIG. 18 shows a FT-IR spectrum of form 2a of Venetoclax.

In another aspect, the present disclosure relates to a crystalline form of Venetoclax, designated form 2a. The crystalline form 2a of Venetoclax may be characterized by data selected from one or more of the following: an X-ray powder diffraction pattern substantially as depicted in FIG. 2; an X-ray powder diffraction pattern having peaks at 5.2, 10.3, 13.7, 17.4 and 24.3 degrees two theta±0.2 degrees two theta; an FT-IR spectrum substantially as depicted in FIG. 18; an FT-IR spectrum having absorptions at 3384, 3341, 1690, 1528, 1482, 1342, 1239, 1204, 1164, 1093, 985, 907, 891, 829, 822 and 741 cm$^{-1}$±1 cm$^{-1}$; and combinations of these data.

Crystalline form 2a of Venetoclax may be further characterized by an X-ray powder diffraction pattern having peaks as described above and also having any one, two, three, four or five additional peaks selected from 8.0, 8.8, 11.5, 17.0 and 20.7 degrees two theta±0.2 degrees two theta.

Figure 2:
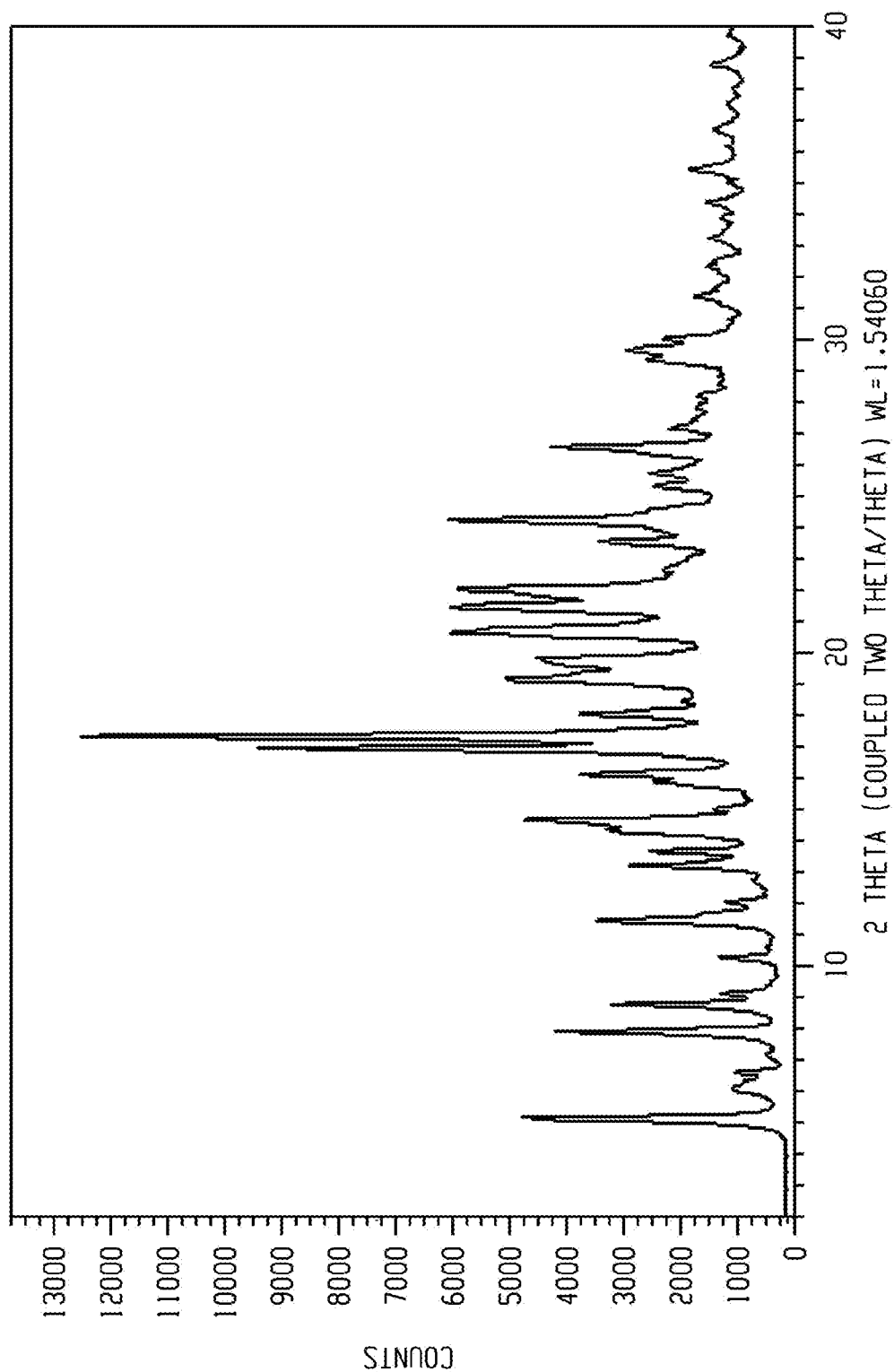
FIG. 2 shows a characteristic X-ray powder diffraction pattern of form 2a of Venetoclax.

Crystalline form 2a of Venetoclax may be characterized by each of the above characteristics alone/or by all possible combinations, e.g. an XRPD pattern having peaks at 8.0, 8.8, 11.5, 17.0 and 20.7 degrees two theta±0.2 degrees two theta; an XRPD pattern as depicted in FIG. 2.

In one embodiment of the present disclosure, form 2a of Venetoclax is isolated.

In another embodiment of the present disclosure, form 2a of Venetoclax is polymorphically pure.

In some embodiments, form 2a of venetoclax may be a cyclohexane solvate. In certain embodiments, form 2a may contain from about 2.0% to about 6.0% of cyclohexane, specifically about 2.5% of cyclohexane.

Figure 3:
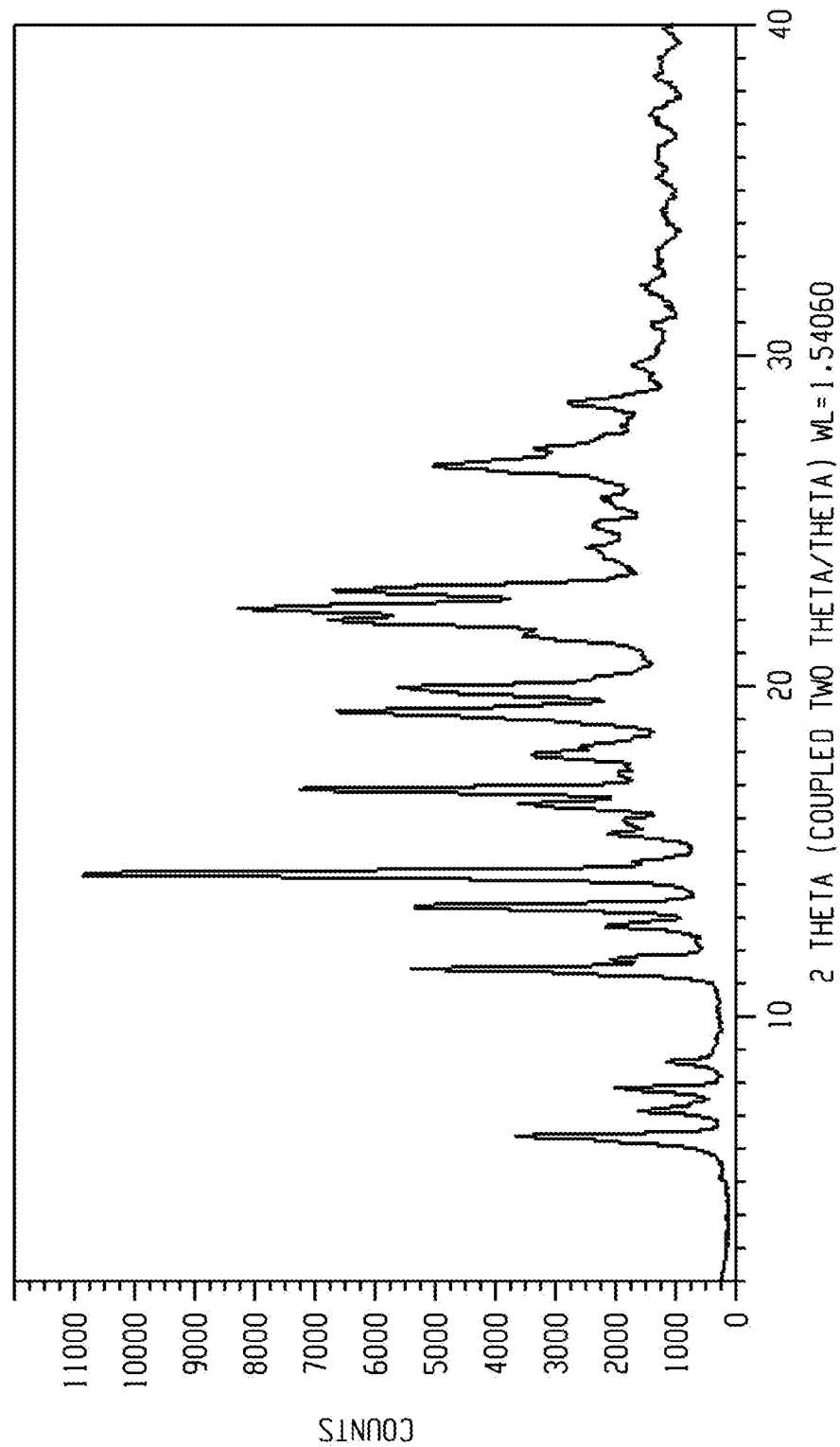
FIG. 3 shows a characteristic X-ray powder diffraction pattern of form 2 of Venetoclax.
Figure 19:
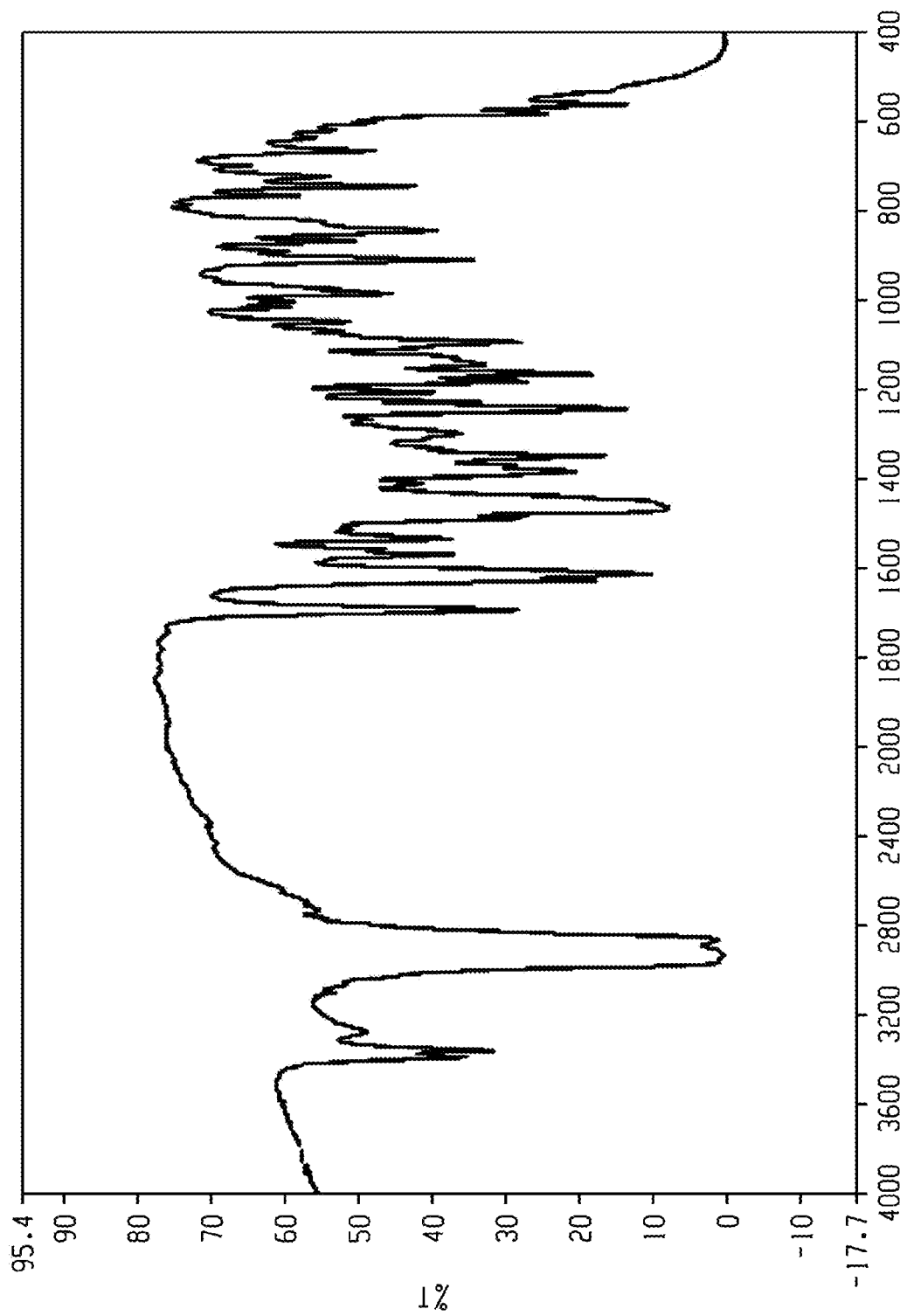
FIG. 19 shows a FT-IR spectrum of form 2 of Venetoclax.
Figure 20:
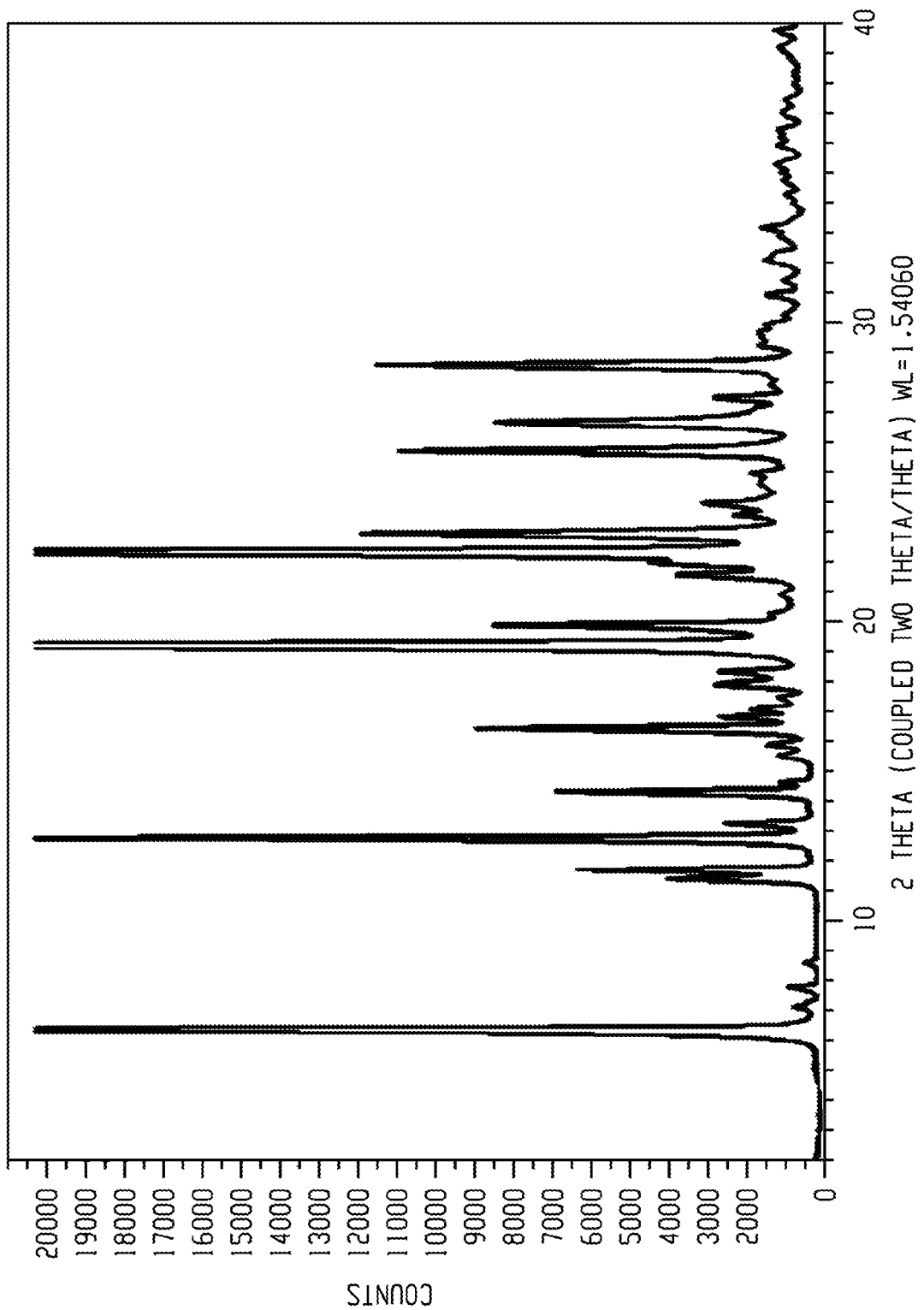
FIG. 20 shows an X-ray powder diffraction pattern of form 2 obtained by procedure 5 of example 4.
Figure 21:
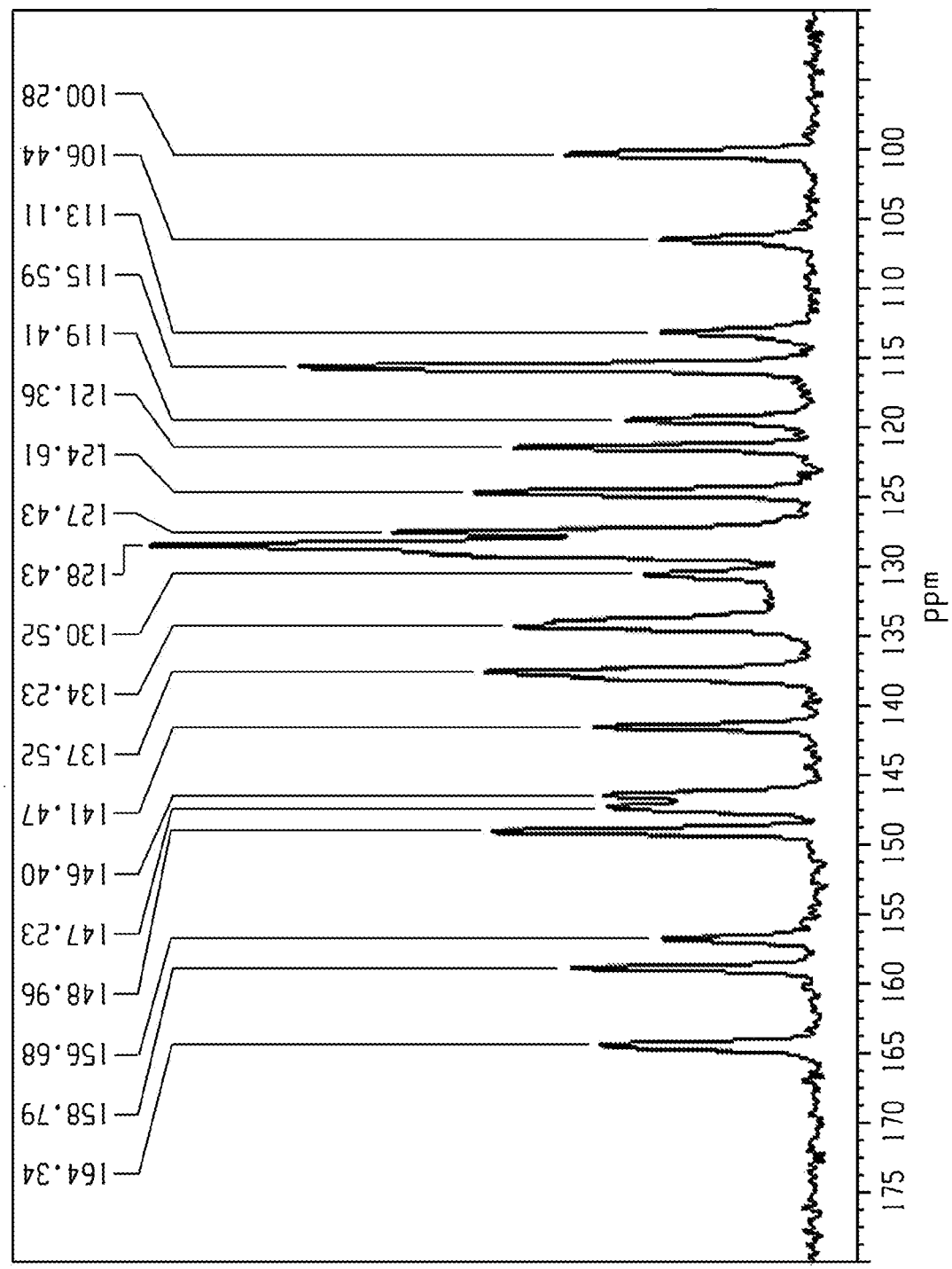
FIG. 21 shows a Solid-state $^{13}C$ NMR spectrum of form 2 of Venetoclax obtained by procedure 5 of example 4.

In another aspect, the present disclosure relates to a crystalline form of Venetoclax, designated form 2. The crystalline form 2 of Venetoclax may be characterized by data selected from one or more of the following: an X-ray powder diffraction pattern substantially as depicted in FIG. 3 or an X-ray powder diffraction pattern substantially as depicted in FIG. 20; an X-ray powder diffraction pattern having peaks at 7.8, 11.4, 13.3, 14.3 and 16.8 degrees two theta±0.2 degrees two theta; an FT-IR spectrum substantially as depicted in FIG. 19; an FT-IR spectrum having absorptions at 3383, 3353, 1688, 1528, 1482, 1342, 1260, 1237, 1204, 1164, 1093, 908, 889, 843 and 697 cm$^{-1}$±1 cm$^{-1}$; a solid state $^{13}$C NMR spectrum substantially as depicted in FIG. 21; a solid state $^{13}$C NMR spectrum having peaks at 128.4, 124.6, 121.4, 115.6 and 100.3 ppm±0.2 ppm; a solid state $^{13}$C NMR spectrum having the following chemical shift absolute differences between said characteristic peaks at 128.4, 124.6, 121.4, 115.6 and 100.3 ppm±0.2 ppm and a reference peak at 149.0 ppm±1 ppm of 20.6, 24.4, 27.6, 33.4 and 48.7 ppm±0.1 ppm; a solid state $^{13}$C NMR spectrum having peaks at 164.3, 158.8, 156.7, 149.0, 147.2, 146.4, 141.5, 137.5, 134.2, 130.5, 128.4, 127.4, 124.6, 121.4, 119.4, 115.6, 113.1, 106.4 and 100.3 ppm±0.2 ppm; and combinations of these data.

Crystalline form 2 of Venetoclax may be further characterized by an X-ray powder diffraction pattern having peaks as described above and also having any one, two, three, four or five additional peaks selected from 6.4, 8.6, 12.8, 19.2 and 19.9 degrees two theta±0.2 degrees two theta.

Crystalline form 2 of Venetoclax may be characterized by the data set forth in the following table.

TABLE

| X-ray powder diffraction peaks of Form 2 of Venetoclax peak position (degrees two theta ± 0.2 degrees two theta) |
|---|
| 6.4 |
| 7.8 |
| 8.6 |
| 11.4 |
| 11.7 |
| 12.8 |
| 13.3 |
| 14.3 |
| 16.5 |
| 16.8 |
| 19.2 |
| 19.9 |
| 22.4 |
| 23.0 |
| 25.7 |
| 26.7 |
| 28.6 |

Crystalline form 2 of Venetoclax may be characterized by each of the above characteristics alone/or by all possible combinations, e.g. an XRPD pattern having peaks at 6.4, 8.6, 12.8, 19.2 and 19.9 degrees two theta±0.2 degrees two theta; an XRPD pattern as depicted in FIG. 3.

In one embodiment of the present disclosure, form 2 of Venetoclax is isolated.

In another embodiment of the present disclosure, form 2 of Venetoclax is polymorphically pure.

In some embodiments, form 2 of Venetoclax may be anhydrous.

In another aspect, the present disclosure relates to a crystalline form of Venetoclax, designated form 3. The crystalline form 3 of Venetoclax may be characterized by data selected from one or more of the following: an X-ray powder diffraction pattern substantially as depicted in FIG. 4; an X-ray powder diffraction pattern having peaks at 6.3, 9.2, 9.6, 15.4 and 17.2 degrees two theta±0.2 degrees two theta; and combinations of these data.

Crystalline form 3 of Venetoclax may be further characterized by an X-ray powder diffraction pattern having peaks as described above and also having any one, two, three, four or five additional peaks selected from 5.3, 8.0, 12.1, 13.5 and 19.5 degrees two theta±0.2 degrees two theta.

Figure 4:
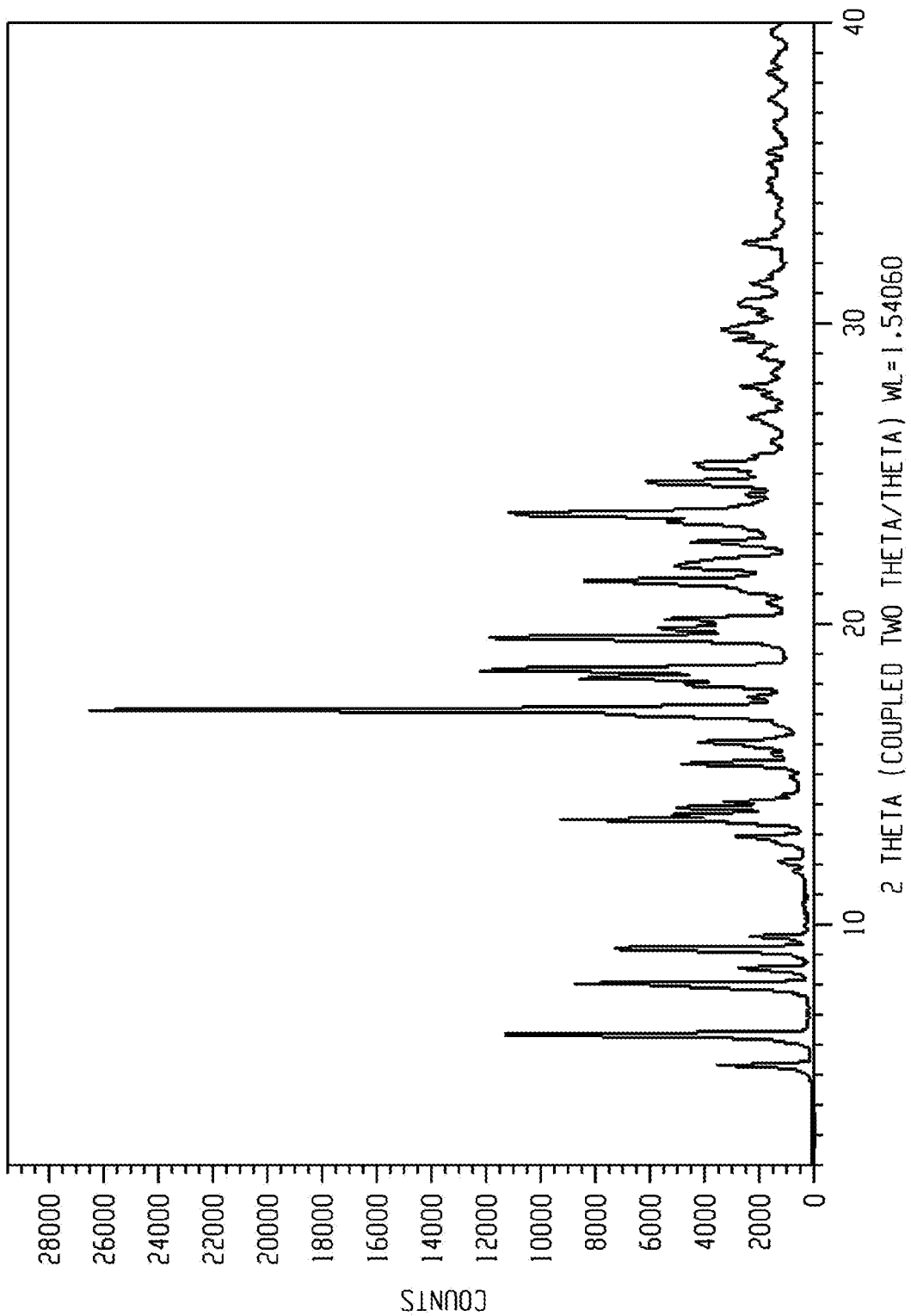
FIG. 4 shows a characteristic X-ray powder diffraction pattern of form 3 of Venetoclax.

Crystalline form 3 of Venetoclax may be characterized by each of the above characteristics alone/or by all possible combinations, e.g. an XRPD pattern having peaks at 5.3, 8.0, 12.1, 13.5 and 19.5 degrees two theta±0.2 degrees two theta; an XRPD pattern as depicted in FIG. 4.

In one embodiment of the present disclosure, form 3 of Venetoclax is isolated.

In another embodiment of the present disclosure, form 3 of Venetoclax is polymorphically pure.

In some embodiments, form 3 of Venetoclax may be a toluene monosolvate. In certain embodiments, form 3 may contain from about 8.0% to about 12.0% of toluene, specifically about 9.6% of toluene.

In another aspect, the present disclosure relates to a crystalline form of Venetoclax, designated form 4. The crystalline form 4 of Venetoclax may be characterized by data selected from one or more of the following: an X-ray powder diffraction pattern substantially as depicted in FIG. 5; an X-ray powder diffraction pattern having peaks at 3.8, 7.7, 8.1, 9.9 and 14.8 degrees two theta±0.2 degrees two theta; and combinations of these data.

Crystalline form 4 of Venetoclax may be further characterized by an X-ray powder diffraction pattern having peaks as described above and also having any one, two, three, four or five additional peaks selected from 15.3, 15.8, 16.5, 17.4 and 18.9 degrees two theta±0.2 degrees two theta.

Figure 5:
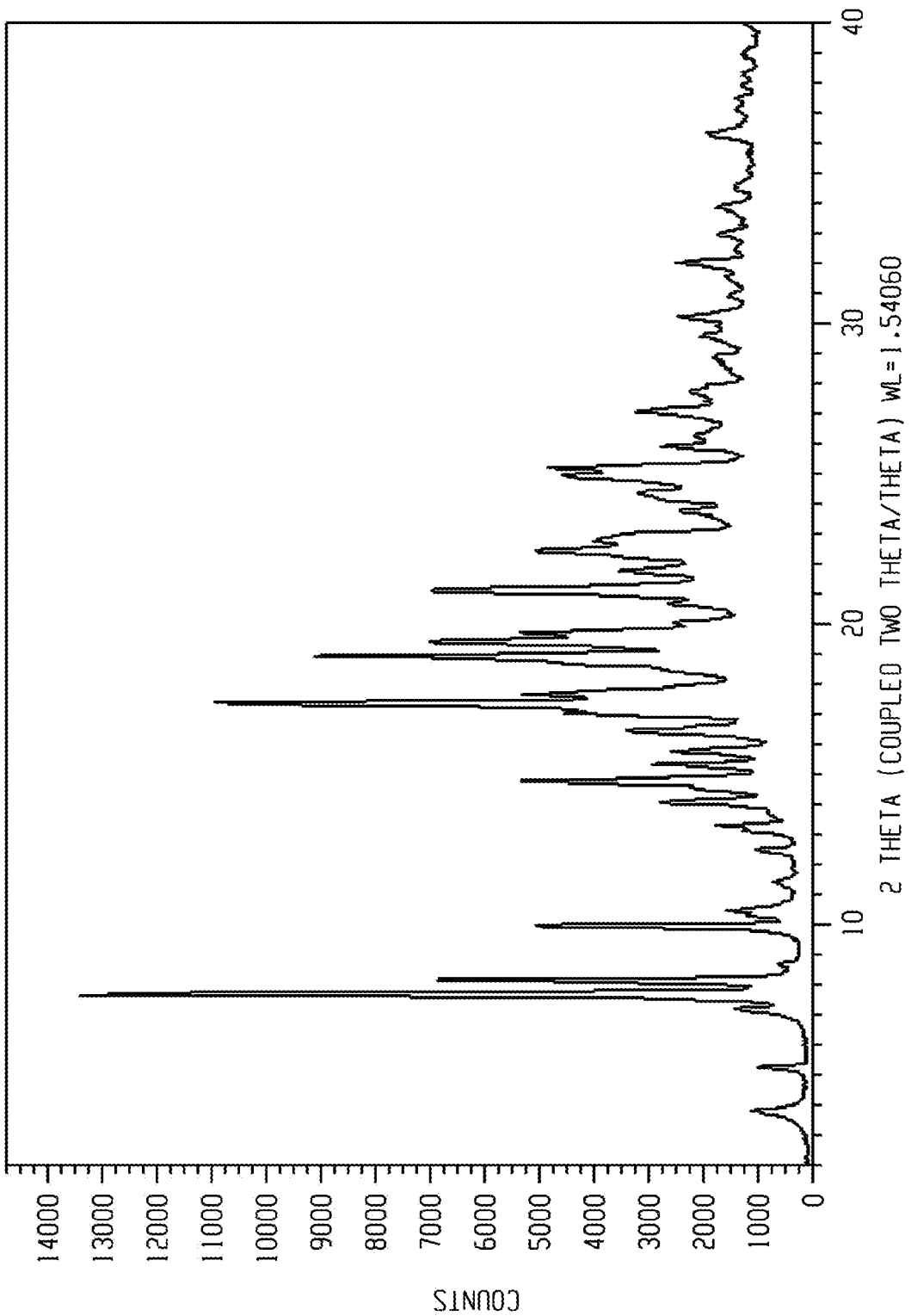
FIG. 5 shows a characteristic X-ray powder diffraction pattern of form 4 of Venetoclax.

Crystalline form 4 of Venetoclax may be characterized by each of the above characteristics alone/or by all possible combinations, e.g. an XRPD pattern having peaks at 15.3, 15.8, 16.5, 17.4 and 18.9 degrees two theta±0.2 degrees two theta; an XRPD pattern as depicted in FIG. 5.

In one embodiment of the present disclosure, form 4 of Venetoclax is isolated.

In another embodiment of the present disclosure, form 4 of Venetoclax is polymorphically pure.

In another aspect, the present disclosure relates to a crystalline form of Venetoclax, designated form 5. The crystalline form 5 of Venetoclax may be characterized by data selected from one or more of the following: an X-ray powder diffraction pattern substantially as depicted in FIG. 6; an X-ray powder diffraction pattern having peaks at 5.2, 10.4, 11.4, 13.8 and 15.2 degrees two theta±0.2 degrees two theta; and combinations of these data.

Crystalline form 5 of Venetoclax may be further characterized by an X-ray powder diffraction pattern having peaks as described above and also having any one, two, three, four or five additional peaks selected from 9.1, 14.3, 19.7, 21.8 and 22.8 degrees two theta±0.2 degrees two theta.

Figure 6:
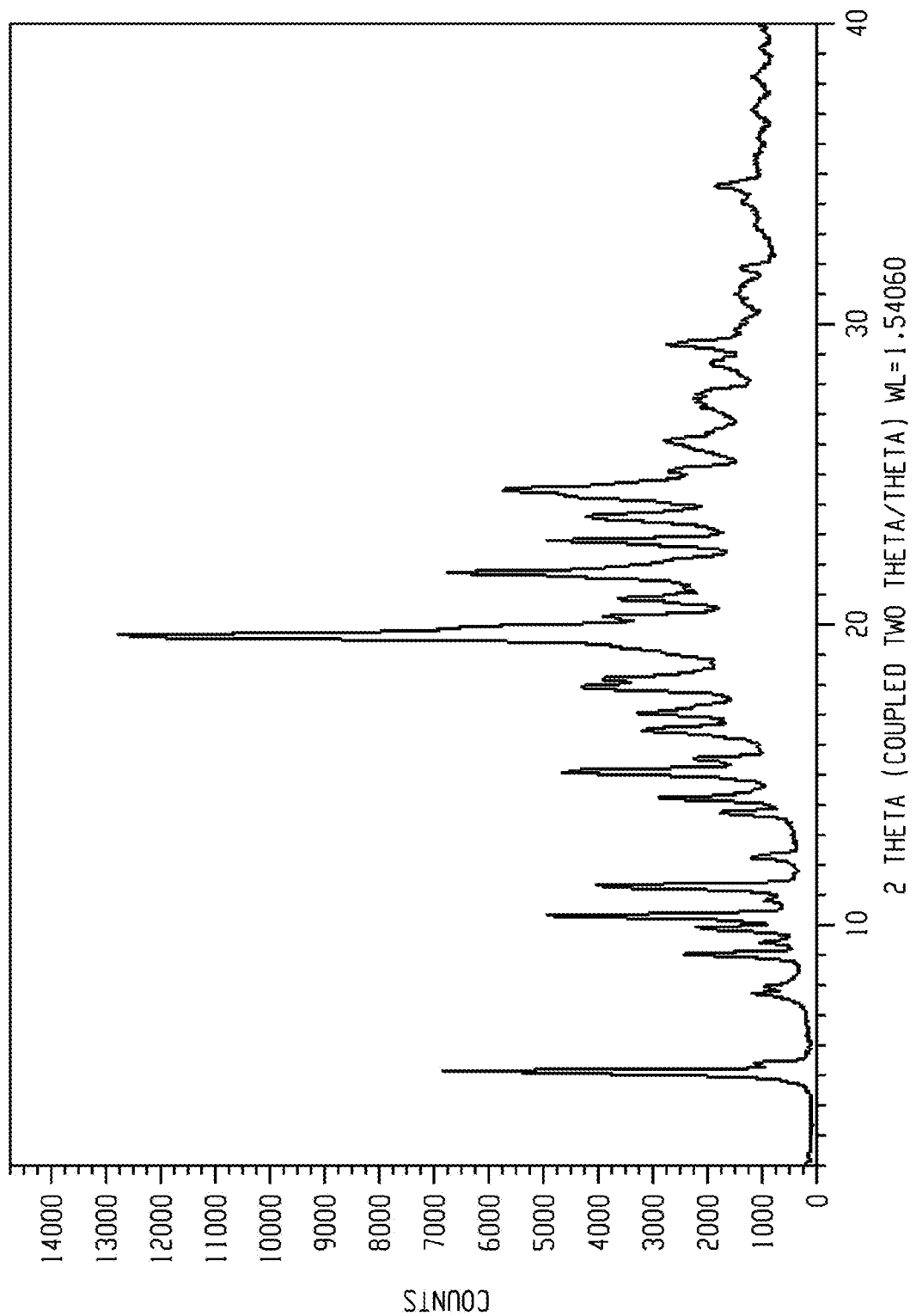
FIG. 6 shows a characteristic X-ray powder diffraction pattern of form 5 of Venetoclax.

Crystalline form 5 of Venetoclax may be characterized by each of the above characteristics alone/or by all possible combinations, e.g. an XRPD pattern having peaks at 9.1, 14.3, 19.7, 21.8 and 22.8 degrees two theta±0.2 degrees two theta; an XRPD pattern as depicted in FIG. 6.

In one embodiment of the present disclosure, form 5 of Venetoclax is isolated.

In another embodiment of the present disclosure, form 5 of Venetoclax is polymorphically pure.

In some embodiments, form 5 of Venetoclax may be anhydrous.

In another aspect, the present disclosure relates to a crystalline form of Venetoclax, designated form 6. The crystalline form 6 of Venetoclax may be characterized by an X-ray powder diffraction pattern having peaks at 5.1, 7.1, 9.4, 15.2 and 18.7 degrees two theta±0.2 degrees two theta.

Crystalline form 6 of Venetoclax may be further characterized by an X-ray powder diffraction pattern having peaks as described above and also having any one, two, three, four or five additional peaks selected from 10.2, 13.0, 14.4, 16.3 and 20.1 degrees two theta±0.2 degrees two theta.

In one embodiment of the present disclosure, form 6 of Venetoclax is isolated.

In some embodiments, form 6 of Venetoclax may be a methyl-isobutyl ketone (MIBK) hemisolvate. In certain embodiments, form 6 may contain from about 5.0% to about 6.0% of MIBK, specifically about 5.5% of MIBK.

In another aspect, the present disclosure relates to a crystalline form of Venetoclax, designated form 7. The crystalline form 7 of Venetoclax may be characterized by data selected from one or more of the following: an X-ray powder diffraction pattern substantially as depicted in FIG. 8; an X-ray powder diffraction pattern having peaks at 3.7, 7.4, 13.3, 14.3 and 16.2 degrees two theta±0.2 degrees two theta; and combinations of these data.

Crystalline form 7 of Venetoclax may be further characterized by an X-ray powder diffraction pattern having peaks as described above and also having any one, two, three, four, five or more additional peaks selected from 6.5, 8.9, 11.8, 17.5, 17.8, 18.8, 20.3, 20.9, 21.4, 23.8, 26.6 and 29.6 degrees two theta±0.2 degrees two theta.

Figure 8:
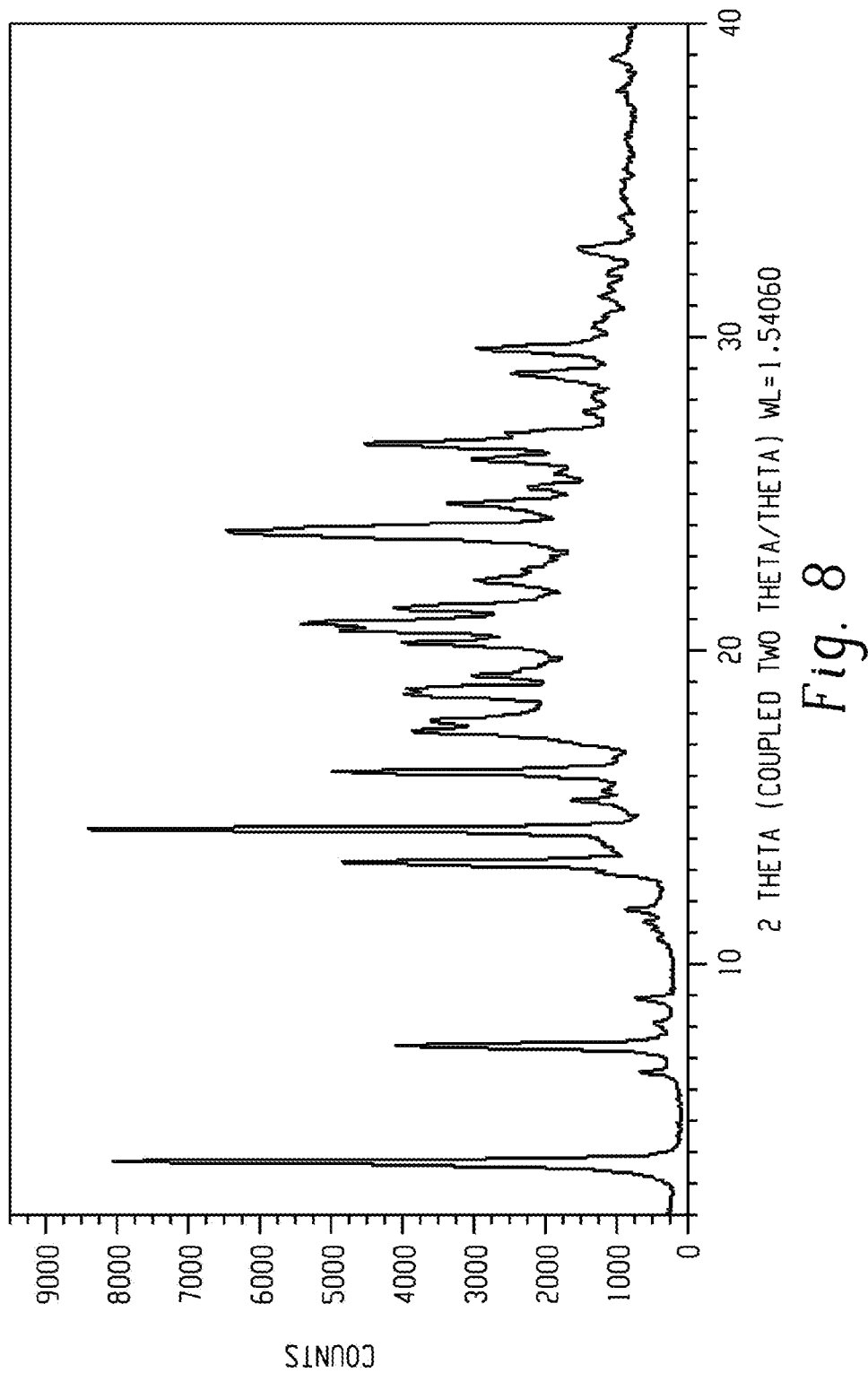
FIG. 8 shows a characteristic X-ray powder diffraction pattern of form 7 of Venetoclax.

Crystalline form 7 of Venetoclax may be characterized by each of the above characteristics alone/or by all possible combinations, e.g. an XRPD pattern having peaks at 3.7, 7.4, 13.3, 14.3 and 16.2 degrees two theta±0.2 degrees two theta; an XRPD pattern as depicted in FIG. 8.

In one embodiment of the present disclosure, form 7 of Venetoclax is isolated.

In some embodiments, form 7 of Venetoclax may be an n-propyl acetate monosolvate. In certain embodiments, form 7 may contain from about 9.0% to about 12.0% of n-propyl acetate, specifically about 10.5% of n-propyl acetate.

In another embodiment of the present disclosure, form 7 of Venetoclax is polymorphically pure.

In another aspect, the present disclosure relates to a crystalline form of Venetoclax, designated form 8. The crystalline form 8 of Venetoclax may be characterized by data selected from one or more of the following: an X-ray powder diffraction pattern substantially as depicted in FIG. 9; an X-ray powder diffraction pattern having peaks at 4.1, 8.2, 13.8, 15.5 and 18.6 degrees two theta±0.2 degrees two theta; and combinations of these data.

Crystalline form 8 of Venetoclax may be further characterized by an X-ray powder diffraction pattern having peaks as described above and also having any one, two, three, four, five or six additional peaks selected from 12.9, 17.7, 18.1, 20.8, 24.8 and 27.9 degrees two theta±0.2 degrees two theta.

Figure 9:
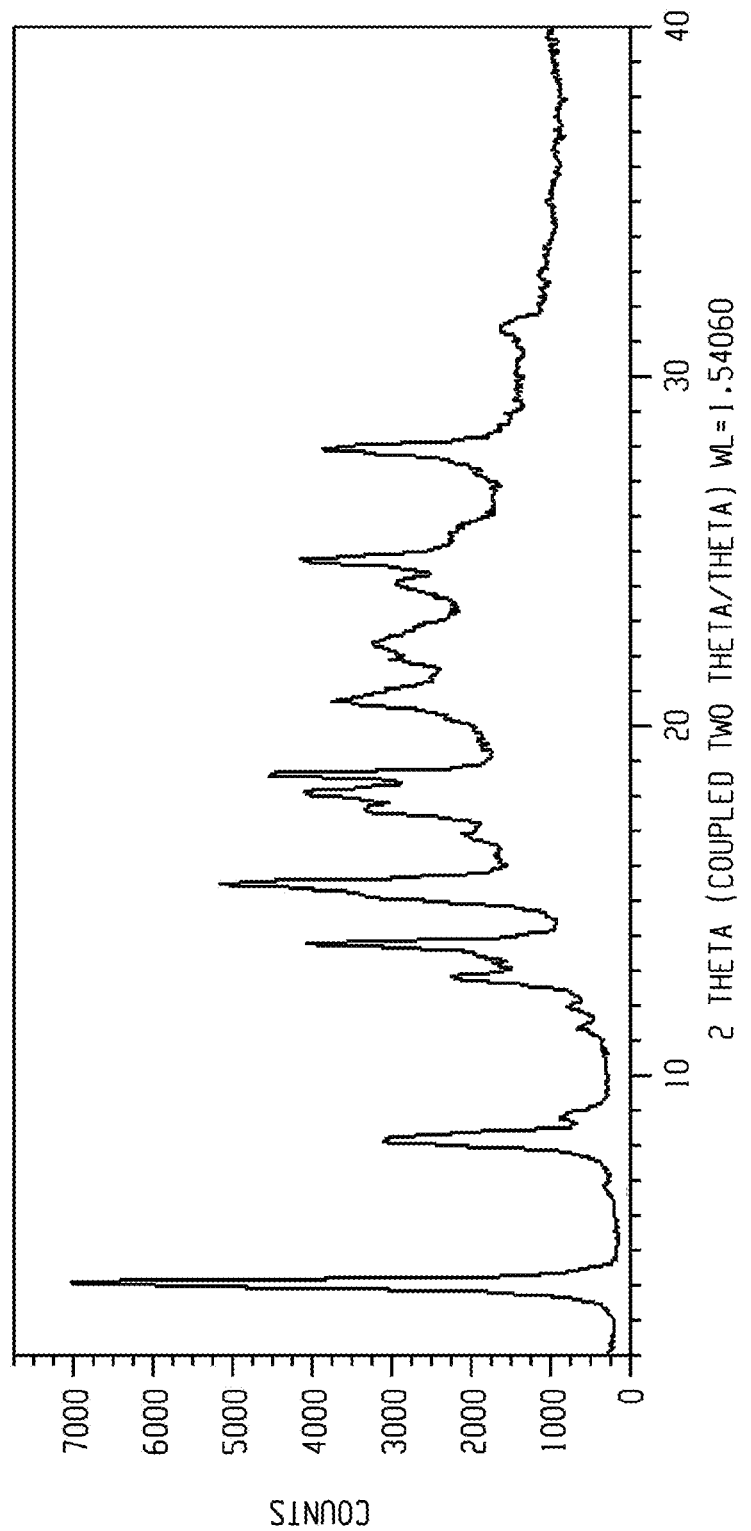
FIG. 9 shows a characteristic X-ray powder diffraction pattern of form 8 of Venetoclax.

Crystalline form 8 of Venetoclax may be characterized by each of the above characteristics alone/or by all possible combinations, e.g. an XRPD pattern having peaks at 4.1, 8.2, 13.8, 15.5 and 18.6 degrees two theta±0.2 degrees two theta; an XRPD pattern as depicted in FIG. 9.

In one embodiment of the present disclosure, form 8 of Venetoclax is isolated.

In another embodiment of the present disclosure, form 8 of Venetoclax is polymorphically pure.

In some embodiments, form 8 of Venetoclax may be anhydrous.

In another aspect, the present disclosure relates to a crystalline form of Venetoclax, designated form 9. The crystalline form 9 of Venetoclax may be characterized by data selected from one or more of the following: an X-ray powder diffraction pattern substantially as depicted in FIG. 10; an X-ray powder diffraction pattern having peaks at 7.4, 11.5, 13.8, 15.2 and 16.0 degrees two theta±0.2 degrees two theta; and combinations of these data.

Crystalline form 9 of Venetoclax may be further characterized by an X-ray powder diffraction pattern having peaks as described above and also having any one, two, three, four, five or more additional peaks selected from 8.5, 12.0, 13.4, 14.3, 17.1, 17.7, 18.4, 19.6, 20.4, 21.1, 24.0, 26.3 and 29.6 degrees two theta±0.2 degrees two theta.

Figure 10:
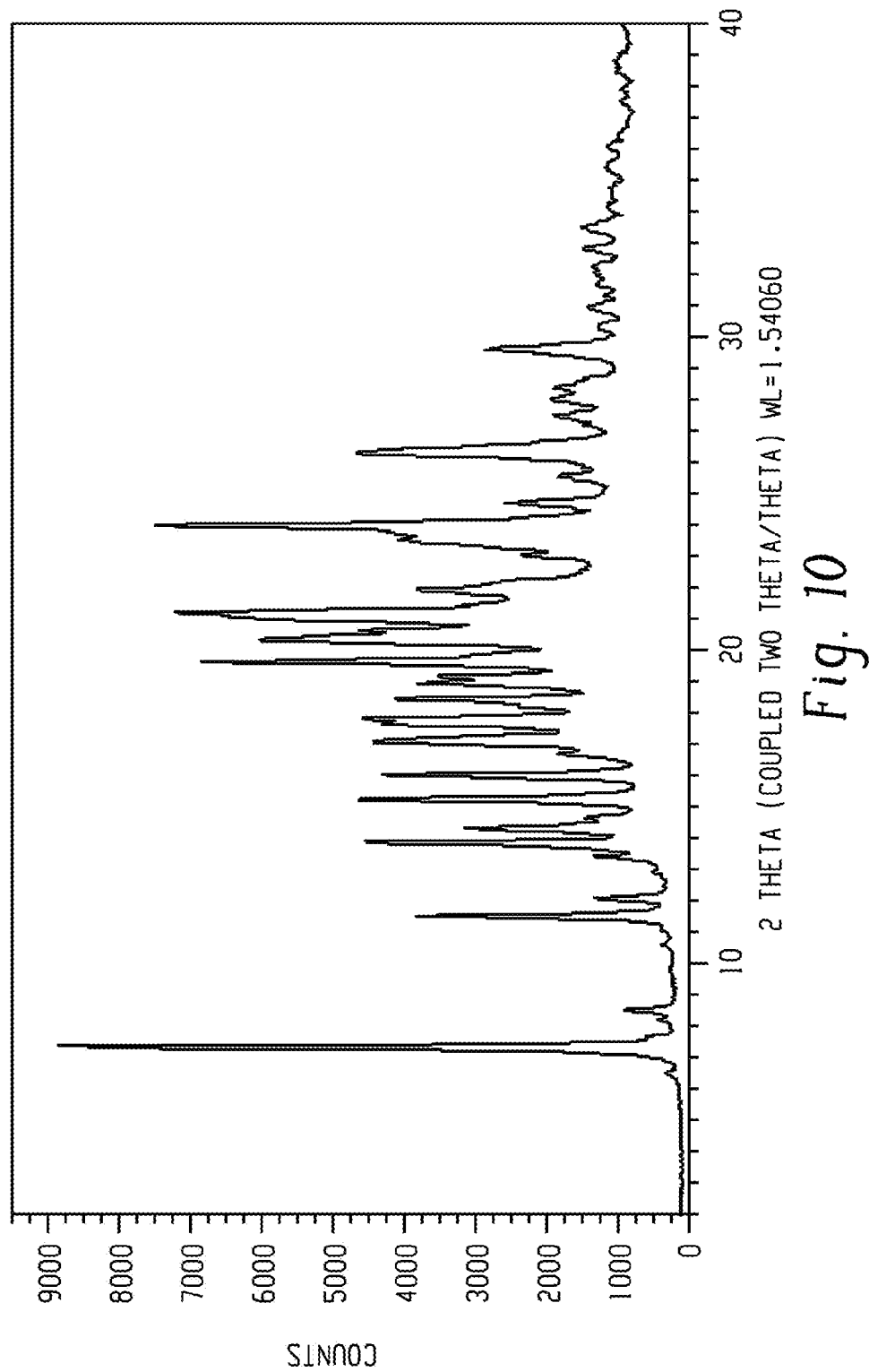
FIG. 10 shows a characteristic X-ray powder diffraction pattern of form 9 of Venetoclax.

Crystalline form 9 of Venetoclax may be characterized by each of the above characteristics alone/or by all possible combinations, e.g. an XRPD pattern having peaks at 7.4, 11.5, 13.8, 15.2 and 16.0 degrees two theta±0.2 degrees two theta; an XRPD pattern as depicted in FIG. 10.

In one embodiment of the present disclosure, form 9 of Venetoclax is isolated.

In another embodiment of the present disclosure, form 9 of Venetoclax is polymorphically pure.

In some embodiments, form 9 of Venetoclax may be a dimethyl carbonate solvate. In certain embodiments, form 9 may contain from about 4.0% to about 6.0% of dimethyl carbonate, specifically about 4.9% of dimethyl carbonate.

In another aspect, the present disclosure relates to a crystalline form of Venetoclax, designated form 10. The crystalline form 10 of Venetoclax may be characterized by data selected from one or more of the following: an X-ray powder diffraction pattern substantially as depicted in FIG. 11; an X-ray powder diffraction pattern having peaks at 5.4, 9.3, 16.2, 18.3 and 24.8 degrees two theta±0.2 degrees two theta; and combinations of these data.

Crystalline form 10 of Venetoclax may be further characterized by an X-ray powder diffraction pattern having peaks as described above and also having any one, two, three, four, five or more additional peaks selected from 7.6, 8.7, 10.9, 11.7, 14.7, 15.2, 18.6, 20.0, 20.8, 21.9, 24.0, 26.3 and 28.6 degrees two theta±0.2 degrees two theta.

Figure 11:
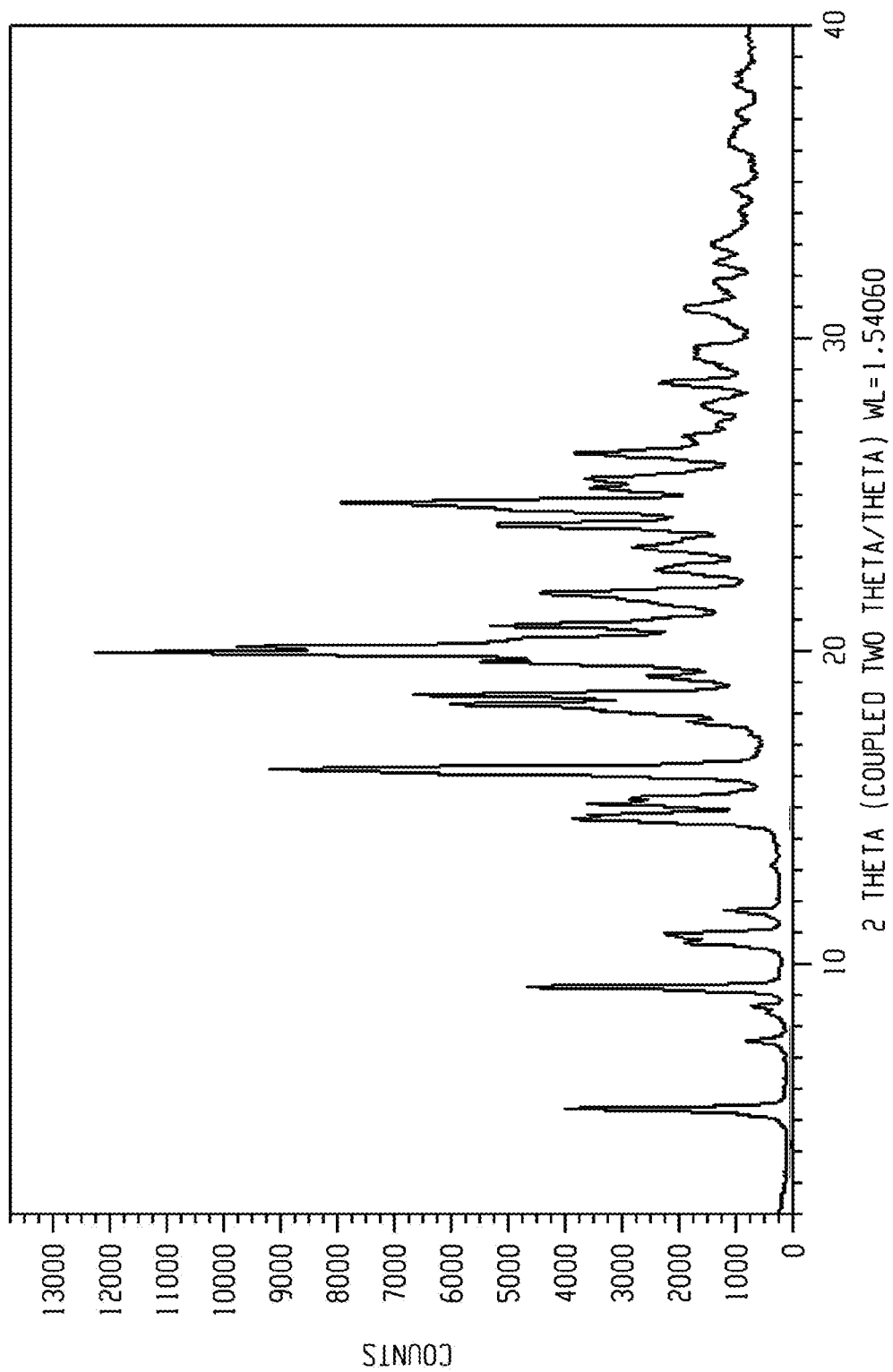
FIG. 11 shows a characteristic X-ray powder diffraction pattern of form 10 of Venetoclax.

Crystalline form 10 of Venetoclax may be characterized by each of the above characteristics alone/or by all possible combinations, e.g. an XRPD pattern having peaks at 5.4, 9.3, 16.2, 18.3 and 24.8 degrees two theta±0.2 degrees two theta; an XRPD pattern as depicted in FIG. 11.

In one embodiment of the present disclosure, form 10 of Venetoclax is isolated.

In another embodiment of the present disclosure, form 10 of Venetoclax is polymorphically pure.

In some embodiments, form 10 of Venetoclax may be a dioxane solvate. In certain embodiments, form 10 may contain from about 3.0% to about 7.0% of dioxane, specifically about 5% of dioxane.

In another aspect, the present disclosure relates to a crystalline form of Venetoclax, designated form 11. The crystalline form 11 of Venetoclax may be characterized by data selected from one or more of the following: an X-ray powder diffraction pattern substantially as depicted in FIG. 12; an X-ray powder diffraction pattern having peaks at 4.9, 8.9, 9.7, 11.2 and 19.0 degrees two theta±0.2 degrees two theta; and combinations of these data.

Crystalline form 11 of Venetoclax may be further characterized by an X-ray powder diffraction pattern having peaks as described above and also having any one, two, three, four, five or more additional peaks selected from 6.6, 8.2, 10.7, 11.3, 13.0, 13.4, 13.9, 14.9, 16.1, 17.1, 18.0, 19.8, 21.3, 23.0, 24.0, 24.5 and 27.9 degrees two theta±0.2 degrees two theta.

Figure 12:
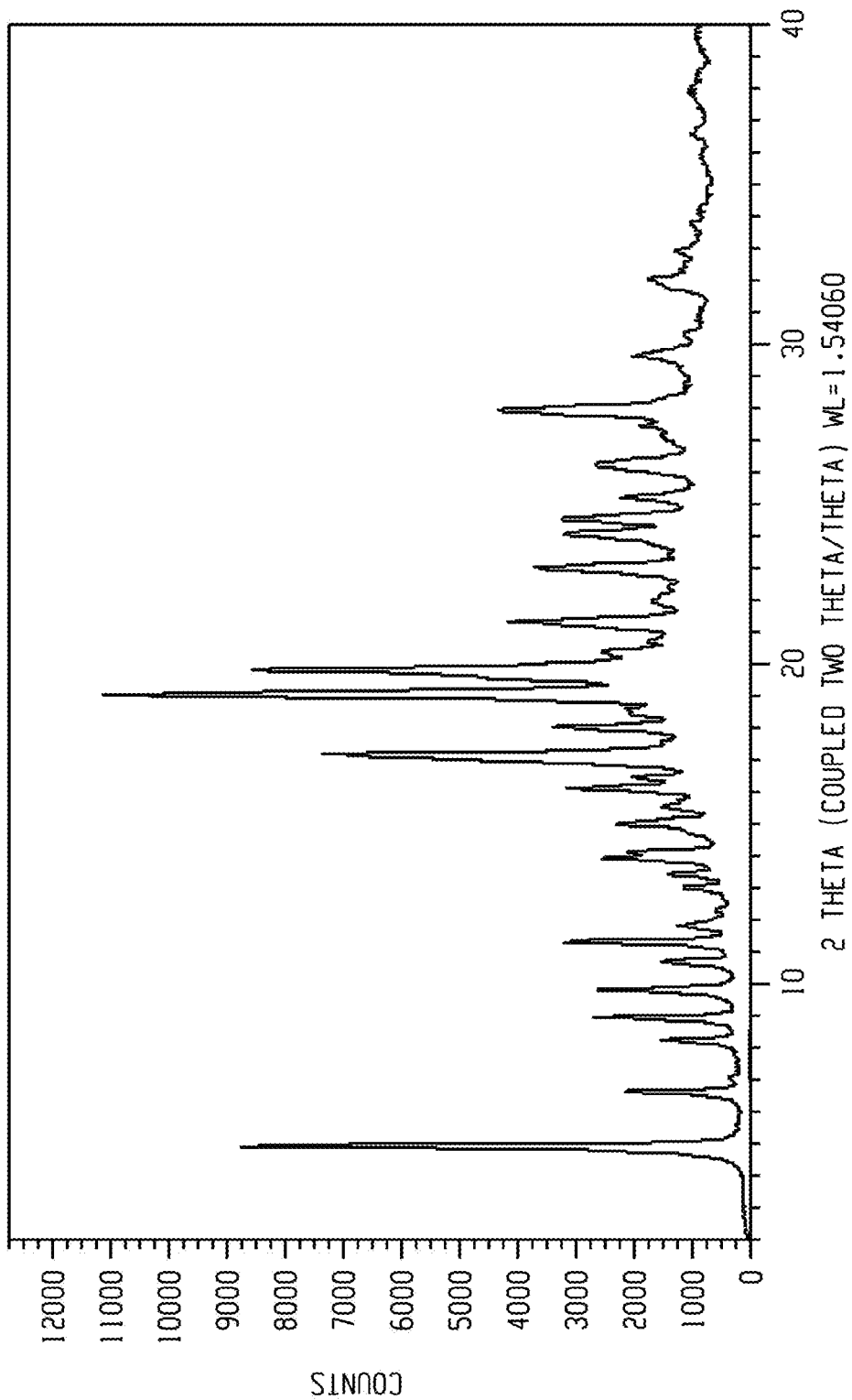
FIG. 12 shows a characteristic X-ray powder diffraction pattern of form 11 of Venetoclax.

Crystalline form 11 of Venetoclax may be characterized by each of the above characteristics alone/or by all possible combinations, e.g. an XRPD pattern having peaks at 4.9, 8.9, 9.7, 11.2 and 19.0 degrees two theta±0.2 degrees two theta; an XRPD pattern as depicted in FIG. 12.

In one embodiment of the present disclosure, form 11 of Venetoclax is isolated.

In another embodiment of the present disclosure, form 11 of Venetoclax is polymorphically pure.

In some embodiments, form 11 of Venetoclax may be an isobutyl acetate solvate.

In certain embodiments, form 11 may contain from about 4.0% to about 7.0% of isobutyl acetate, specifically about 6.2% of isobutyl acetate.

In another aspect, the present disclosure relates to a crystalline form of Venetoclax, designated form 12. The crystalline form 12 of Venetoclax may be characterized by data selected from one or more of the following: an X-ray powder diffraction pattern substantially as depicted in FIG. 14; an X-ray powder diffraction pattern having peaks at 4.4, 10.9, 16.4, 17.9 and 20.4 degrees two theta±0.2 degrees two theta; and combinations of these data.

Crystalline form 12 of Venetoclax may be further characterized by an X-ray powder diffraction pattern having peaks as described above and also having any one, two, three, four, five or more additional peaks selected from 9.1, 10.2, 12.4, 13.2, 15.7, 15.9, 19.0, 21.1, 21.4, 23.9, 24.9 and 29.0 degrees two theta±0.2 degrees two theta.

Figure 14:
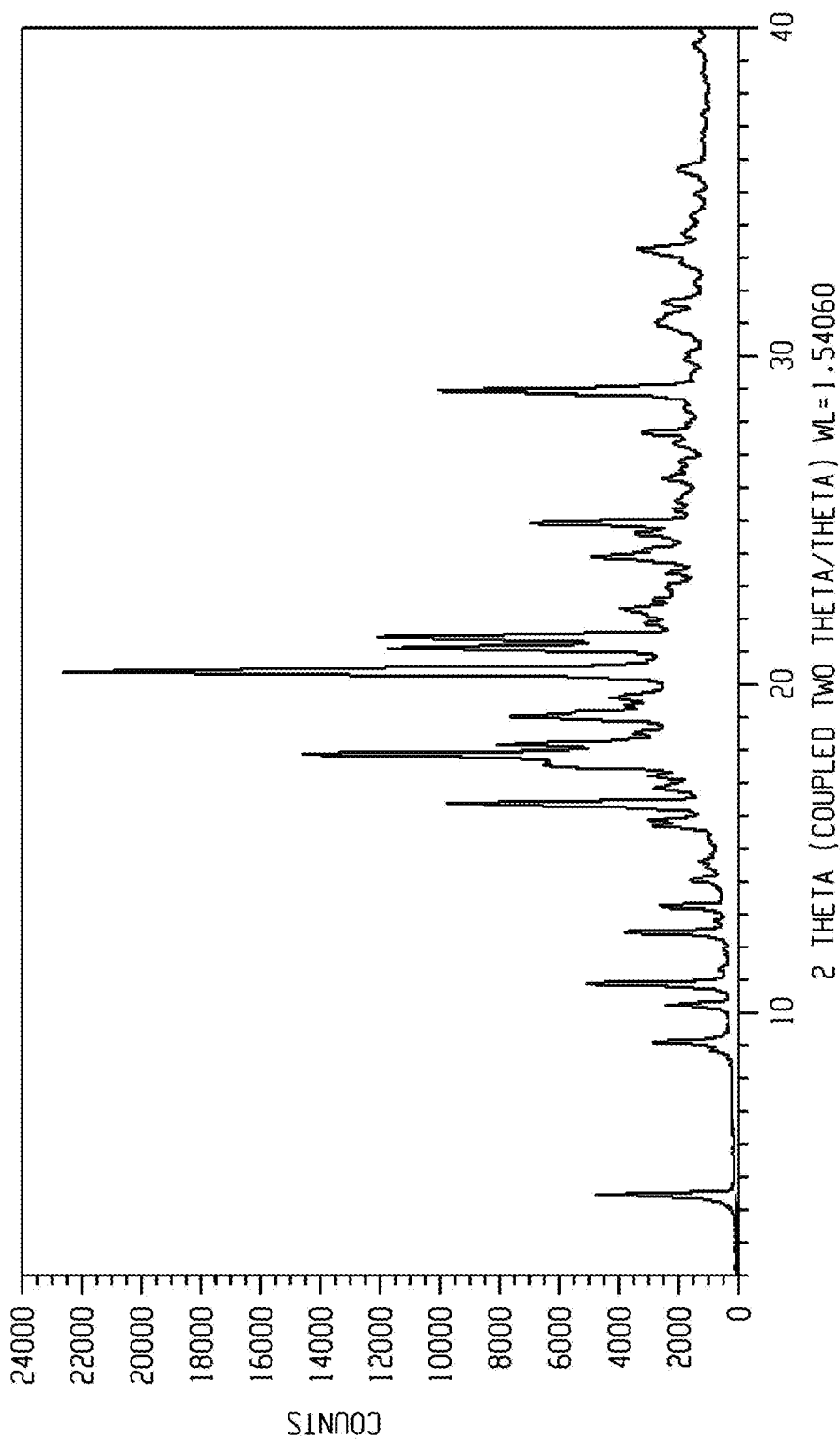
FIG. 14 shows a characteristic X-ray powder diffraction pattern of form 12 of Venetoclax.

Crystalline form 12 of Venetoclax may be characterized by each of the above characteristics alone/or by all possible combinations, e.g. an XRPD pattern having peaks at 4.4, 10.9, 16.4, 17.9 and 20.4 degrees two theta±0.2 degrees two theta; an XRPD pattern as depicted in FIG. 14.

In one embodiment of the present disclosure, form 12 of Venetoclax is isolated.

In another embodiment of the present disclosure, form 12 of Venetoclax is polymorphically pure.

In another aspect, the present disclosure relates to a crystalline form of Venetoclax, designated form 13. The crystalline form 13 of Venetoclax may be characterized by data selected from one or more of the following: an X-ray powder diffraction pattern substantially as depicted in FIG. 15; an X-ray powder diffraction pattern having peaks at 5.9, 10.7, 13.1, 15.7 and 21.3 degrees two theta±0.2 degrees two theta; and combinations of these data.

Crystalline form 13 of Venetoclax may be further characterized by an X-ray powder diffraction pattern having peaks as described above and also having any one, two, three, four, five or more additional peaks selected from 7.2, 13.5, 13.8, 14.9, 17.3, 17.7, 18.1, 19.0, 19.5, 23.5, 24.7 and 26.4 degrees two theta±0.2 degrees two theta.

Figure 15:
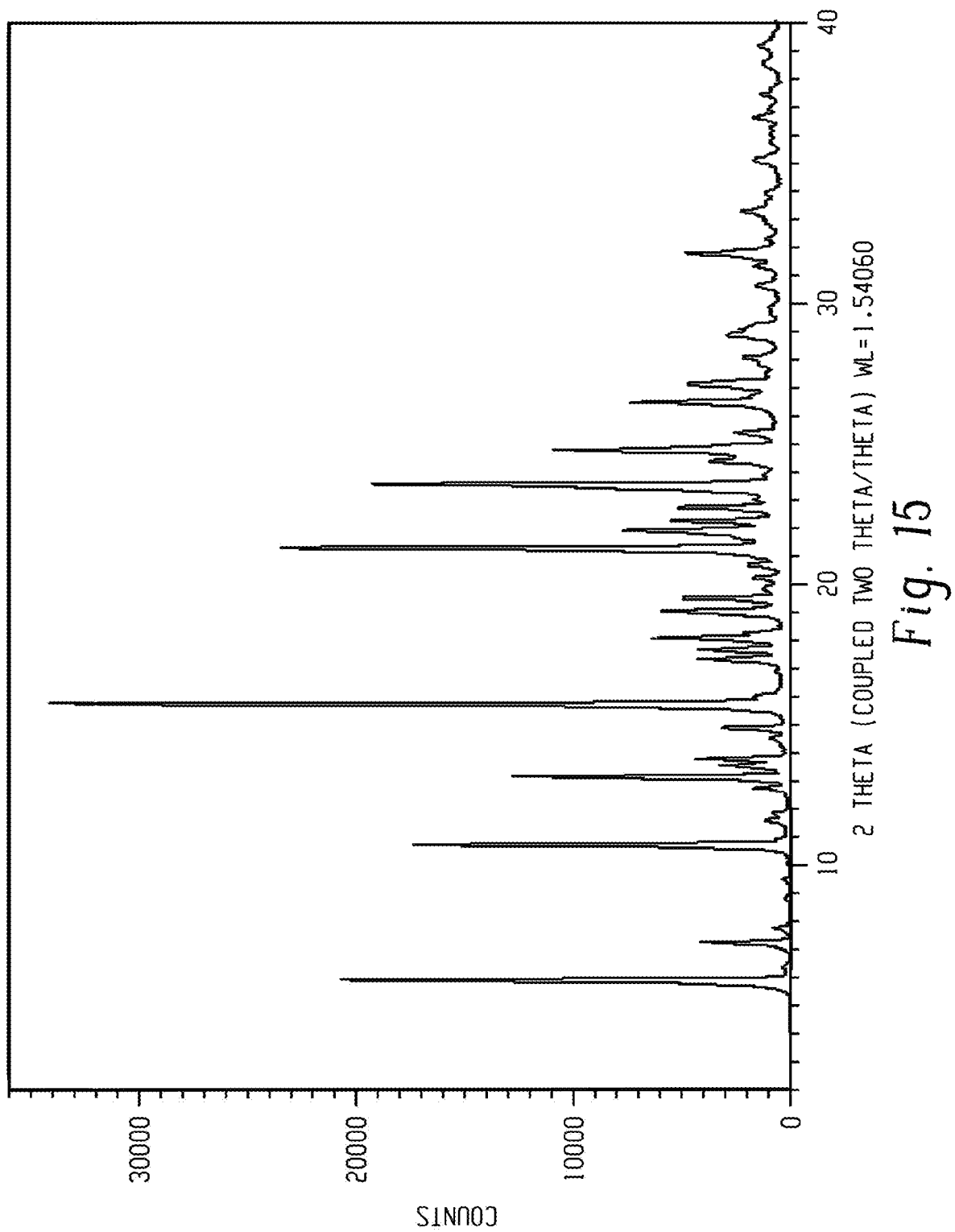
FIG. 15 shows a characteristic X-ray powder diffraction pattern of form 13 of Venetoclax.

Crystalline form 13 of Venetoclax may be characterized by each of the above characteristics alone/or by all possible combinations, e.g. an XRPD pattern having peaks at 5.9, 10.7, 13.1, 15.7 and 21.3 degrees two theta±0.2 degrees two theta; an XRPD pattern as depicted in FIG. 15.

In one embodiment of the present disclosure, form 13 of Venetoclax is isolated.

In another embodiment of the present disclosure, form 13 of Venetoclax is polymorphically pure.

In some embodiments, form 13 of Venetoclax may be a dimethyl carbonate solvate. In certain embodiments, form 13 may contain from about 2.0% to about 6.0% of dimethyl carbonate, specifically about 4.9% of dimethyl carbonate.

In another aspect, the present disclosure relates to a crystalline form of Venetoclax, designated form 14. The crystalline form 14 of Venetoclax may be characterized by data selected from one or more of the following: an X-ray powder diffraction pattern substantially as depicted in FIG. 16; an X-ray powder diffraction pattern having peaks at 4.6, 9.1, 13.4, 18.0 and 21.0 degrees two theta±0.2 degrees two theta; and combinations of these data.

Crystalline form 14 of Venetoclax may be further characterized by an X-ray powder diffraction pattern having peaks as described above and also having any one, two, three, four, five or more additional peaks selected from 10.1, 10.8, 13.9, 15.2, 17.4, 19.1, 20.2, 22.0, 25.1 and 29.4 degrees two theta±0.2 degrees two theta.

Figure 16:
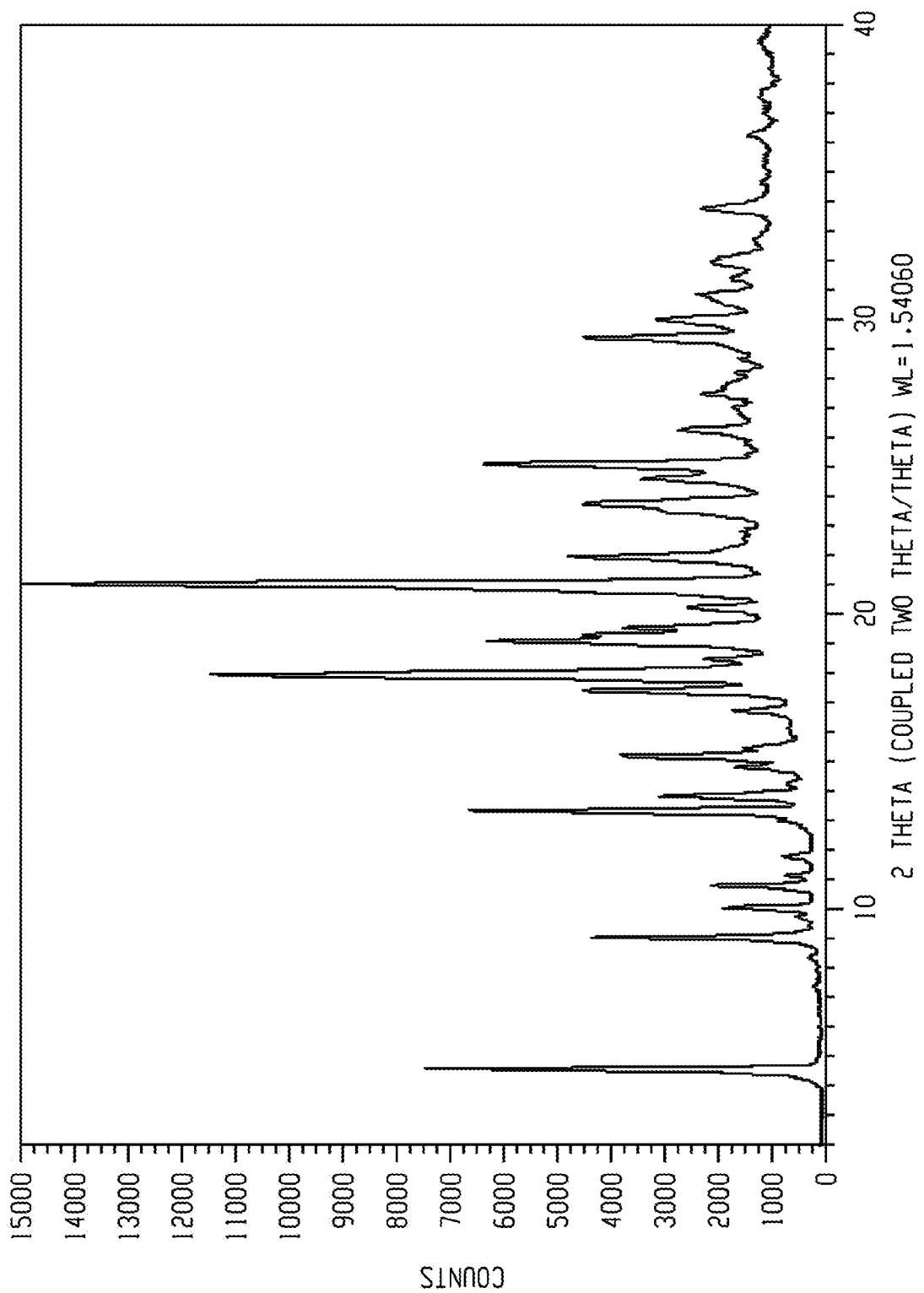
FIG. 16 shows a characteristic X-ray powder diffraction pattern of form 14 of Venetoclax.

Crystalline form 14 of Venetoclax may be characterized by each of the above characteristics alone/or by all possible combinations, e.g. an XRPD pattern having peaks at 4.6, 9.1, 13.4, 18.0 and 21.0 degrees two theta±0.2 degrees two theta; an XRPD pattern as depicted in FIG. 16.

In one embodiment of the present disclosure, form 14 of Venetoclax is isolated.

In another embodiment of the present disclosure, form 14 of Venetoclax is polymorphically pure.

Figure 22:
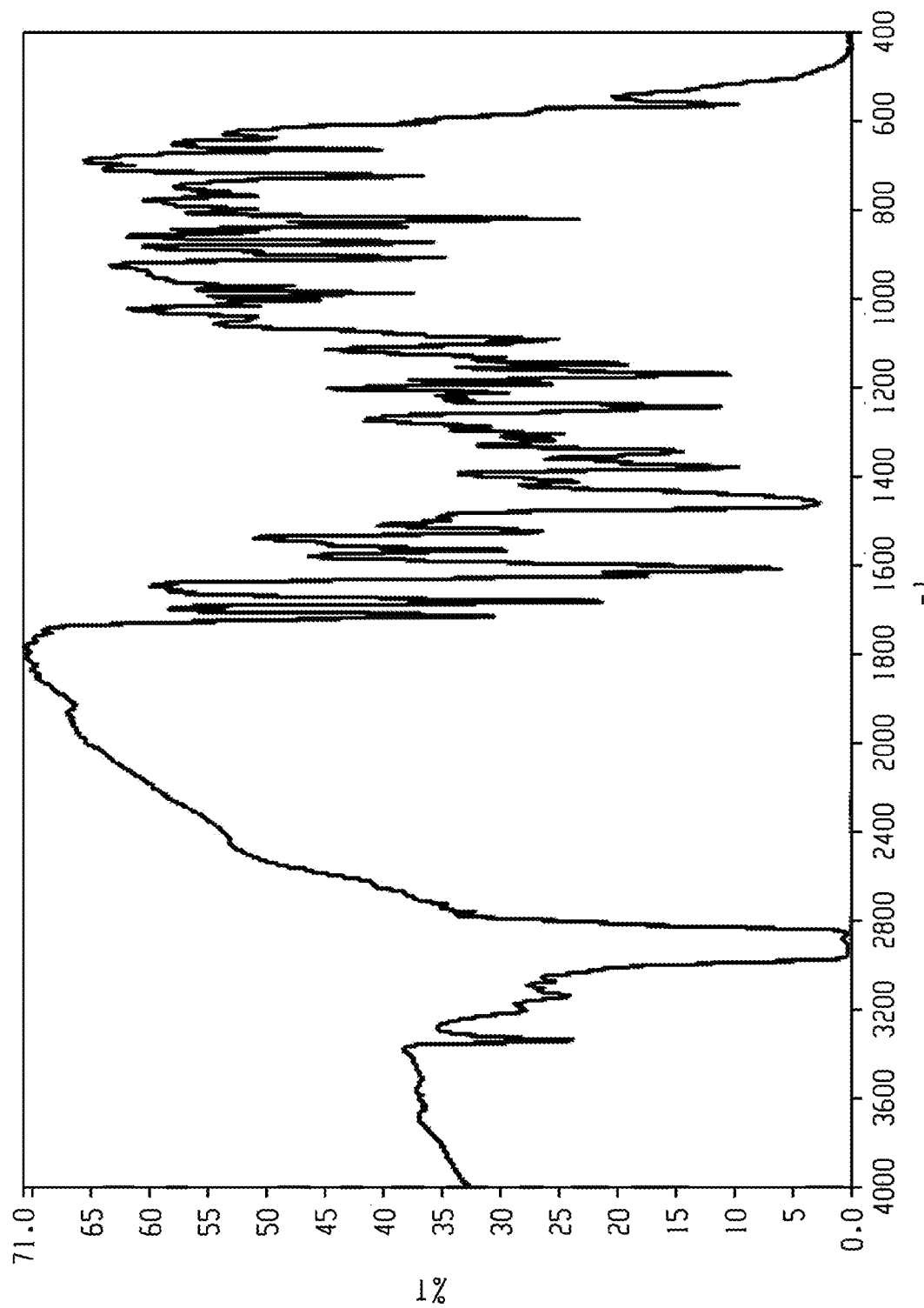
FIG. 22 shows a FT-IR spectrum of form 15 of Venetoclax.

In another aspect, the present disclosure relates to a crystalline form of Venetoclax, designated form 15. The crystalline form 15 of Venetoclax may be characterized by data selected from one or more of the following: an X-ray powder diffraction pattern substantially as depicted in FIG. 17; an X-ray powder diffraction pattern having peaks at 5.7, 7.0, 12.4, 13.4 and 14.4 degrees two theta±0.2 degrees two theta; an FT-IR spectrum substantially as depicted in FIG. 22; an FT-IR spectrum having absorptions at 3339, 1712, 1679, 1606, 1564, 1340, 1241, 1190, 1167, 1145, 985, 905, 871, 818, 720 and 662 $cm^{-1}\pm 1$ $cm^{-1}$; and combinations of these data.

Crystalline form 15 of Venetoclax may be further characterized by an X-ray powder diffraction pattern having peaks as described above and also having any one, two, three, four, five or more additional peaks selected from 10.3, 11.5, 13.0, 15.7, 17.4, 17.9, 18.8, 20.8, 24.2, 25.4 and 25.9 degrees two theta±0.2 degrees two theta.

Figure 17:
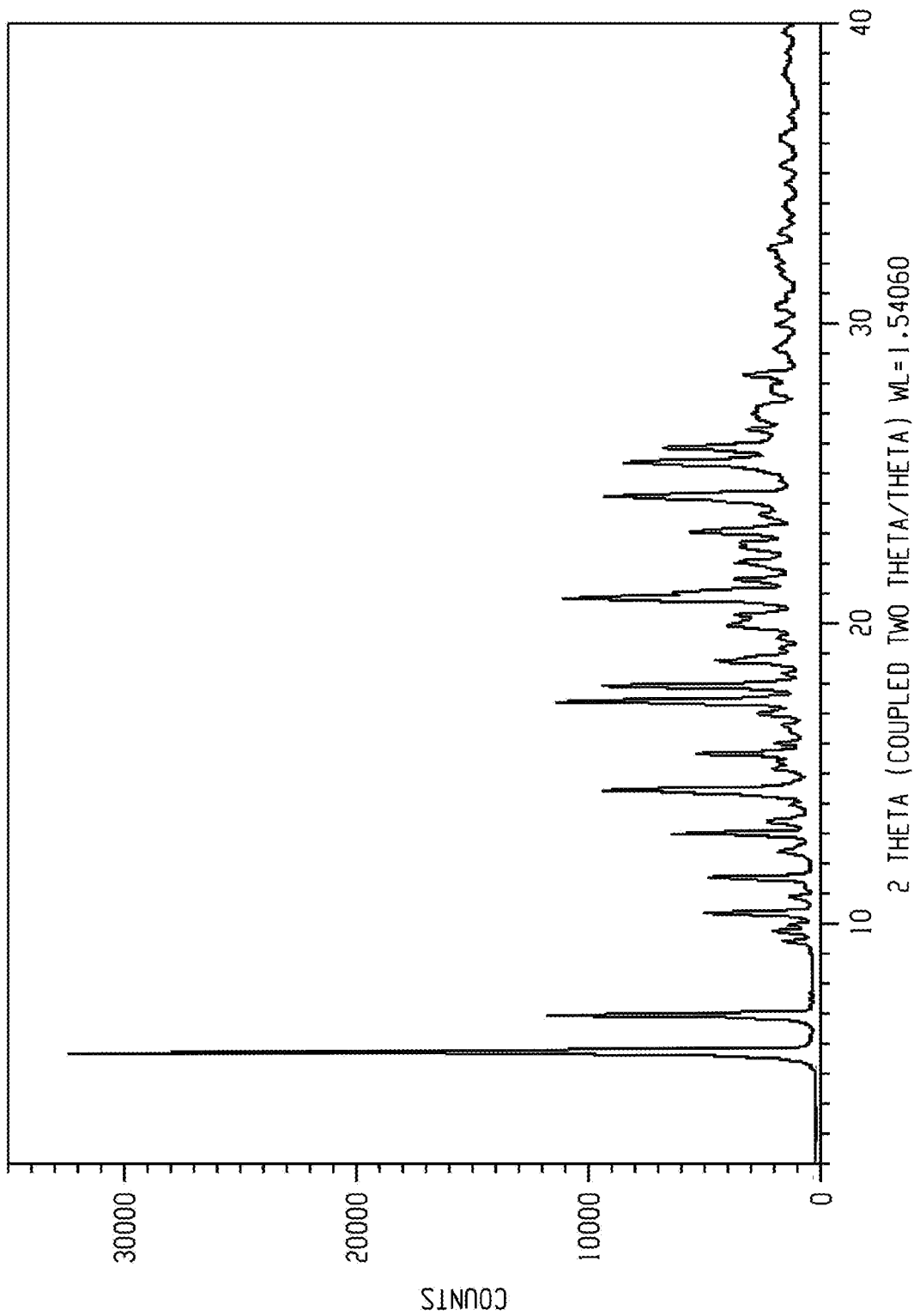
FIG. 17 shows a characteristic X-ray powder diffraction pattern of form 15 of Venetoclax.

Crystalline form 15 of Venetoclax may be characterized by each of the above characteristics alone/or by all possible combinations, e.g. an XRPD pattern having peaks at 5.7, 7.0, 12.4, 13.4 and 14.4 degrees two theta±0.2 degrees two theta; an XRPD pattern as depicted in FIG. 17.

In one embodiment of the present disclosure, form 15 of Venetoclax is isolated.

In another embodiment of the present disclosure, form 15 of Venetoclax is polymorphically pure.

In some embodiments, form 15 of Venetoclax may be a methyl ethyl ketone solvate. In certain embodiments, form 15 may contain from about 10.0% to about 15.0% of methyl ethyl ketone, specifically about 12.1% of methyl ethyl ketone.

In another aspect the present disclosure provides a process for preparing crystalline form 15 comprising slurrying Venetoclax in a solvent comprising methyl ethyl ketone. In one embodiment the present disclosure provides a process for preparing crystalline form 15 comprising a) providing Venetoclax in a solvent comprising methyl ethyl ketone and optionally stirring; b) optionally cooling and optionally stirring, and c) optionally isolating Crystalline form 15.

The starting material for this process can be any solid state form, preferably a crystalline form of Venetoclax. Preferably, the starting material is obtained by crystallization of Venetoclax from a solvent comprising dichloromethane, or a solvent comprising dichloromethane and one or both of methanol and ethylacetate. More preferably the starting material for this process may be obtained by crystallization of Venetoclax from a mixture of methanol, dichloromethane, and ethyl acetate, preferably in a volume ratio of methanol: dichloromethane:ethyl acetate of about 1:about 5-15:about 5-15, more preferably in a volume ratio of about 1:9-11:8-10, and most preferably about 1:10:9. Preferably the starting material may be obtained by dissolving Venetoclax in dichloromethane and methanol, preferably at elevated temperature, and adding ethyl acetate, and optionally cooling. The elevated temperature is preferably from about 25° C. to about 50° C., more preferably about 30° C. to about 45° C. The ethyl acetate is preferably added slowly (e.g. dropwise). The mixture is preferably cooled, more preferably cooled to about −5° C. to about 10° C., preferably about −5° C. to about 5° C. The product is preferably filtered and dried. The drying is preferably conducted under reduced pressure (e.g. 50-300 mbar, preferably 80-120 mbar), preferably for about 4 to about 12 hours, more preferably for about 6 to about 10 hours.

Preferably, the solution in step a) comprises at least a 50%, more preferably at least 70%, most preferably at least 90% of methyl ethyl ketone or at least 95% or at least 98% of methyl ethyl ketone (by volume). The solution in step a) may also comprise another solvent, preferably an organic solvent that is miscible with methyl ethyl ketone. Preferably the solution in step a) may comprise a chlorinated hydrocarbon, and/or an alcohol. More preferably the solution in step a) may comprise dichloromethane or methanol, or a combination of dichloromethane and methanol. Preferably the mixture of step a) is provided at an elevated temperature, for example, a temperature range of: about 25° C. to about 70° C., about 35° C. to about 60° C. or about 45° C. to about 55° C. Step a) may preferably comprise stirring the mixture at the elevated temperature. The stirring may be carried out for: about 0.5 to about 6 hours, or about 1 to about 4 hours, or about 1-3 hours. Step b) may comprise cooling the mixture, preferably to a temperature of: about 5° C. to about 20° C. or about 10° C. to about 18° C. Step b) may preferably comprise stirring the cooled mixture. The stirring may be carried out for about 2 to about 24 hours, about 4 to about 20 hours, about 6 to about 12 hours, or about 8 to about 10 hours.

The crystalline form 15 can be isolated by any method known in the art, For example, crystalline form 15 of Venetoclax can be separated by filtering the slurry or decanting the solvent from the slurry. The isolating method can further comprise washing the crystalline form 15 of Venetoclax.

In another aspect the disclosure relates to form 15 produced by the above described process.

In another aspect the present disclosure provides a process for preparing crystalline form 2a comprising crystallizing Venetoclax from a solvent comprising cyclohexane. In one embodiment the present disclosure provides a process for preparing crystalline form 2a comprising a) providing Venetoclax in a solvent comprising cyclohexane; b) optionally cooling and optionally stirring; and c) isolating Crystalline form 2a.

Preferably, the solvent in step a) comprises about 10% to about 90% of cyclohexane (by volume). More preferably the solvent in step a) comprises: about 15% to about 80%, about 20% to about 70% or about 20% to about 65% cyclohexane (by volume).

The solvent in step a) comprises cyclohexane and at least one polar solvent, preferably a polar aprotic solvent, preferably selected from an ether, a ketone or an ester. Particularly the solvent in step a) comprises cyclohexane and at least one solvent selected from the group consisting of ethyl acetate, acetone and THF. In some embodiments, the solvent in step a) comprises cyclohexane and THF. Preferably the mixture in step a) comprises about 15% to about 75%, about 15% to about 70%, about 20% to about 60%, or about 20% to about 40% of cyclohexane (by volume) in THF.

Preferably the stirring in step b) is performed for about 1 to about 24 hours. Preferably, step a) comprises providing a solution of Venetoclax in at least one solvent at an elevated temperature, and optionally cooling. Step a) can comprise dissolving Venetoclax in the polar solvent (e.g. at least one of ethyl acetate, acetone or THF), preferably at an elevated temperature, and adding the cyclohexane preferably at an elevated temperature, and cooling. The elevated temperature may be from about 40° C. to about 90° C., more preferably from about 45° C. to about 80° C., and particularly about 50° C. to about 75° C.

Preferably, the mixture of Venetoclax in the at least one solvent in step a) is a solution. The mixture in step a) may be cooled, preferably to a temperature of about −5° C. to about 35° C., more preferably about 0° C. to about 30° C., and more preferably about 4° C. to about 25° C.

Optionally, the mixture from step a) may be stirred, preferably at a temperature of about −5° C. to about 35° C., more preferably about 0° C. to about 30° C., and more preferably about 4° C. to about 25° C. The stirring may be carried out for about 1 to about 36 hours, preferably about 3 to about 24 hours, about 4 to about 12 hours or about 6 to about 10 hours.

Preferably the process of the present disclosure for preparation of form 2a is performed with stirring. Preferably the stirring may be at about 60 to about 500 rpm, about 70 to about 400 rpm, about 80 to about 250 rpm, or about 100 to about 350 rpm.

The crystalline form 2a can be isolated by any method known in the art, For example, crystalline form 2a of Venetoclax can be separated by filtering the slurry or decanting the solvent from the slurry. The isolating method can further comprise washing.

Crystalline form 2a may be further dried to obtain crystalline form 2. Preferably crystalline form 2a of Venetoclax is dried at a temperature of about 40° C. to about 110° C. under reduced pressure, more preferably at a temperature of about 90° C. to about 110° C. under reduced pressure in order to obtain crystalline form 2.

In another aspect the disclosure relates to form 2a produced by the above described process.

In another aspect the present disclosure provides a process for preparation of crystalline form 2 comprising drying of form 2a. Preferably crystalline form 2a of Venetoclax is dried at a temperature of about 20° C. to about 110° C., about 35° C. to about 90° C., or about 40° C. to about 80° C. More preferably, the drying is conduct under reduced pressure.

In another aspect the disclosure relates to form 2 produced by the above described process.

The solid forms of the present disclosure may exhibit advantageous properties. For example, the solid state forms of the present disclosure may exhibit high stability, e.g. thermodynamic stability, stability to polymorphic conversion, stability to chemical conversion, or stability to conditions of high humidity.

The methyl ethyl ketone solvate (e.g. Form 15 of the present disclosure) offers significant impurity purging capabilities in that crude Venetoclax having a purity of about 60 A % (as determined by HPLC) before crystallization was upgraded to about 97 A % after crystallization in a solvent comprising methyl ethyl ketone. Thus the preparation of a methyl ethyl ketone solvate of Venetoclax enables the chemical purification of crude Venetoclax. Thus the disclosure further provides a method for purifying Venetoclax via the preparation of a methyl ethyl ketone solvate. The disclosure further provides the use of a methyl ethyl ketone solvate (e.g. Form 15 of the present disclosure) as an intermediate for the purification of Venetoclax.

Therefore, the disclosure also provides a process for purification of Venetoclax comprising slurrying venetoclax in a solvent comprising methyl ethyl ketone. Preferably, the solvent comprises at least 50%, more preferably at least 70%, most preferably at least 90% of methyl ethyl ketone, or at least 95% or at least 98% of methyl ethyl ketone (by volume).

All of the solid state forms of Venetoclax disclosed above can be used for preparation of other solid state forms of Venetoclax and Venetoclax pre-mix. Preferably, the disclosure provides the use of form 2 for the preparation of amorphous Venetoclax or Venetoclax Premix. The disclosure also provides for form 2 for use for the preparation of amorphous Venetoclax or Venetoclax premix.

Amorphous Venetoclax may be prepared, for example by a process comprising providing a solution of form 2 of Venetoclax in a solvent, followed by rapid precipitation or by rapid solvent removal.

For example, amorphous Venetoclax can be prepared by a process comprising a) providing form 2 of Venetoclax; b) dissolving Venetoclax in a solvent comprising at least one suitable organic solvents, preferably polar aprotic solvents; c) removing the solvent from the solution in step b) by any method known in the art; d) optionally slurrying the product of step c in water and e) optionally isolating amorphous Venetoclax. The solvent removal can be carried out, for example, by vacuum distillation or by spray drying.

Suitable polar aprotic solvents may include for example esters, ethers, ketones and amides, such as, for example n-propylacetate, DMF, THF, acetone and EtOAc.

Alternatively, amorphous Venetoclax may be prepared for example by a process comprising a) providing form 2 of Venetoclax; b) dissolving Venetoclax in a solvent comprising at least one suitable organic solvent, preferably polar aprotic solvents; c) pouring the solution formed in step b into ice water, and d) optionally isolating amorphous Venetoclax.

Suitable polar aprotic solvents may include for example esters, ethers ketone and amides, such as, for example n-propylacetate, DMF, THF, acetone and EtOAc.

Amorphous Venetoclax can be isolated by any method known in the art, for example, amorphous Venetoclax can be separated by filtering the slurry or decanting the solvent from the slurry. The isolating method can further comprise washing and drying.

The Venetoclax pre-mix can be a co-precipitate of Venetoclax with a pharmaceutically acceptable carrier, and optionally other pharmaceutically acceptable excipients. Preferably the pharmaceutically acceptable carrier is copovidone and/or povidone.

The Venetoclax premix can be a crystalline premix or an amorphous premix.

Preferably, the pre-mix comprises Venetoclax and a carrier, preferably wherein the carrier is copovidone. Preferably the pre-mix contains a weight ratio of carrier: Venetoclax of: about 8:2, about 7:3 to about 3:7, about 6:4 to about 4:6, about 45:55 to about 55:45, about 50:50.

Preferably, the pre-mix comprises the carrier, preferably wherein the carrier is copovidone and/or povidone, in an amount of about 80 to about 20 wt %, 70 to about 30 wt %, about 40 to about 60 wt %, about 50 wt %. Preferably, the pre-mix comprises Venetoclax in an amount of about 70 to about 30 wt %, about 60 to about 40 wt %, about 50 wt %.

In some embodiments the present disclosure relates to processes for preparation of a premix of Venetoclax comprising combining any one of the above solid state forms of Venetoclax, preferably form 2, with a pharmaceutically acceptable carrier, preferably copovidone and/or povidone, and optionally other pharmaceutically acceptable excipients.

In some embodiments, Venetoclax amorphous pre-mix can be prepared by mixing Venetoclax with at least one carrier, preferably povidone and/or copovidone, and optionally other pharmaceutically acceptable excipients or mixture of excipients, providing a mixture that is then combined with an alcohol such as ethanol, isopropanol, or the like, to yield a second mixture. Preferably, both Venetoclax and the carrier are dissolved in the second mixture. The solvent is then removed from the second mixture by evaporation techniques such as spray drying, EKATO or rotavapor. The resulting mixture may be in the form of a powder, which may be subjected to a particle size reduction step (e.g., by milling).

Preferably, Venetoclax amorphous pre-mix can be prepared by mixing any one of the above solid state forms of Venetoclax with povidone and/or copovidone and optionally other pharmaceutically acceptable excipients, providing a mixture that is then combined with ethanol to yield a second mixture. The solvent is then removed from the second mixture by evaporation techniques such as spray drying, an agitated dryer (e.g. EKATO). The resulting mixture may be in the form of a powder, which may be subjected to a particle size reduction step (e.g., by milling).

In some embodiments, Venetoclax crystalline pre-mix can be prepared by dissolving the carrier, such as povidone and/or copovidone, in a solvent such as water or alcohols or other organic solvent, adding venetoclax and removing the solvent by methods such as lyophilization or vacuum distillation. Preferably, the venetoclax is not dissolved in the solution of the carrier and the solvent. The resulting mixture may be in the form of a powder, which may be subjected to a particle size reduction step (e.g., by milling).

In some embodiments, Venetoclax crystalline pre-mix can be prepared by adding the carrier, such as povidone and/or copovidone, to a solvent such as water or alcohols or other organic solvent, heating the reaction mass to a temp in the range of about 30 deg. C. to about 65 deg. C. to afford a clear solution, or heat up to the boiling point of the applied solvent to form clear solution adding Venetoclax with stirring to provide a mixture that is then lyophilized. The resulting mixture may be in the form of a powder, which may be subjected to a particle size reduction step (e.g., by milling).

In some embodiments the present disclosure relates to processes for preparation of a premix of Venetoclax and other active pharmaceutical ingredients, which can be used in combination with Venetoclax, comprising combining any one of the above solid state forms or amorphous form of Venetoclax with other active pharmaceutical ingredients, a pharmaceutically acceptable carrier and optionally other pharmaceutically acceptable excipients.

The above solid state forms may be used to purify Venetoclax, or may be used as intermediates for the purification of Venetoclax.

The above solid state forms can be used to prepare other solid state forms of Venetoclax, Venetoclax salts, and solid state forms thereof.

The present disclosure provides solid state forms of Venetoclax for use in the preparation of pharmaceutical compositions comprising Venetoclax.

The present disclosure also encompasses the use of the Venetoclax solid state forms of the present disclosure for the preparation of pharmaceutical compositions of Venetoclax.

The present disclosure comprises processes for preparing the above mentioned pharmaceutical compositions. The processes comprise combining the Venetoclax solid state forms with at least one pharmaceutically acceptable excipient.

The solid state forms and the pharmaceutical compositions of Venetoclax of the present disclosure can be used as medicaments, particularly for the treatment of chronic lymphocytic leukemia.

The present disclosure also provides methods of treating of chronic lymphocytic leukemia comprising administering a therapeutically effective amount of a venetoclax solid state form of the present disclosure, or at least one of the above pharmaceutical compositions, to a subject in need of the treatment.

The solid state forms of Venetoclax of the present disclosure may be used for preparation of amorphous venetoclax or Venetoclax pre-mix.

In another aspect the disclosure relates to processes for preparation of Venetoclax. The process of the present disclosure can be illustrated by the following scheme 1:

Scheme 1

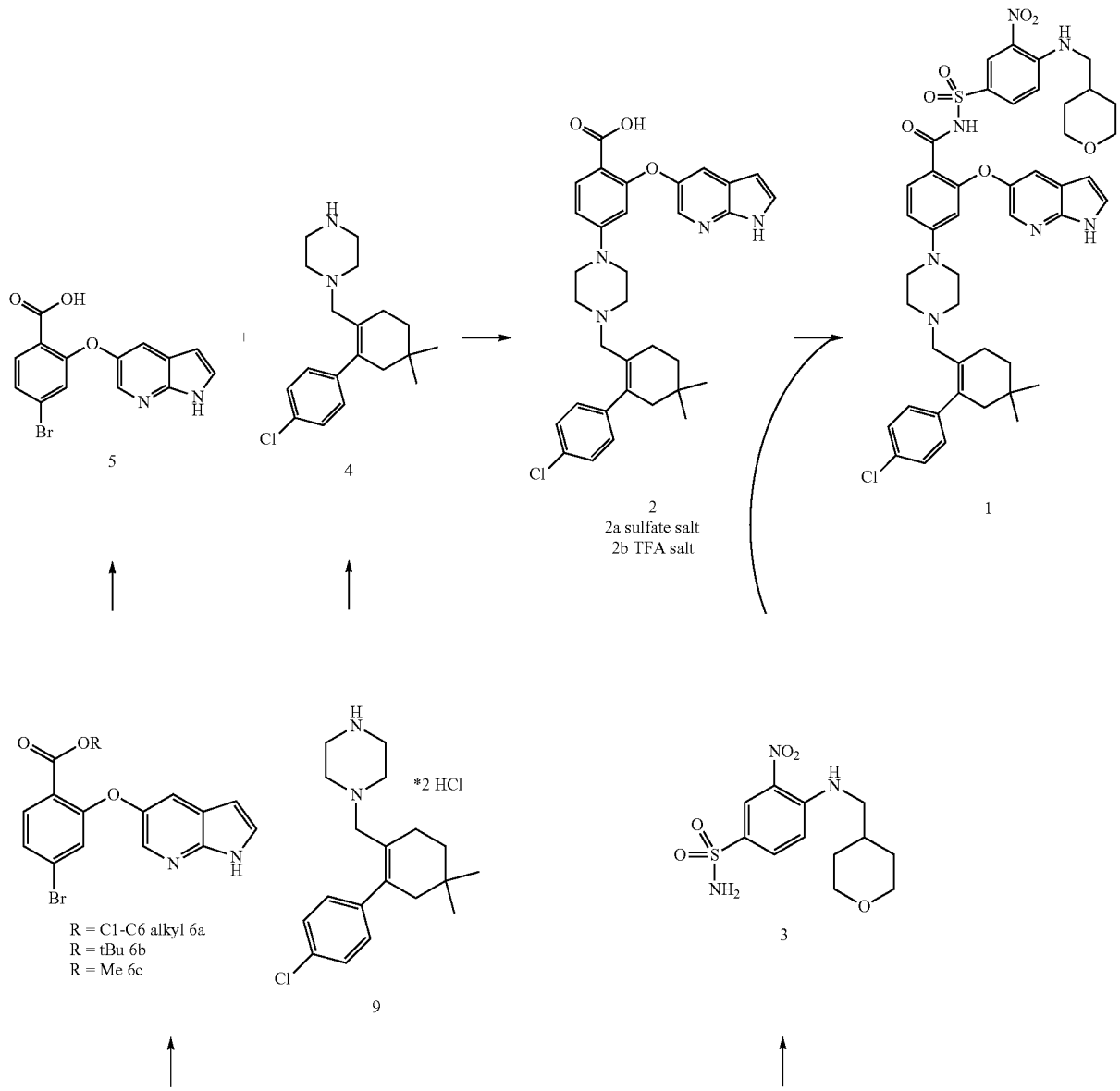

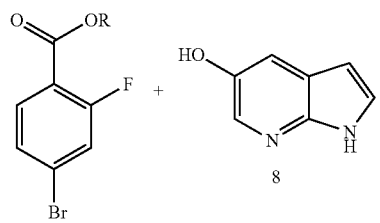

R = C1-C6 alkyl 7a
R = tBu 7b
R = Me 7c

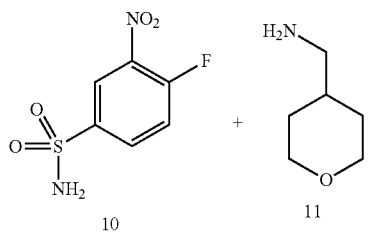

In another aspect the disclosure provides a process for the preparation of Venetoclax that comprises:
a) reacting a compound of formula 5, with a compound of formula 4, to provide compound of formula 2;
b) reacting the compound of formula 2 with compound of formula 3 to afford Venetoclax (compound 1).

Compound 2 may be in free base form, or may be acid salt, for example, a mono or diacid salt such as monohydrogen phosphate, dihydrogen phosphate, HCl, TFA or $H_2SO_4$). Preferably compound 2 is the sulfate salt 2a of the TFA salt 2b.

Step a) is typically carried out in the presence of a suitable solvent, a source of palladium, suitable phosphine ligand, or alternatively a pre-prepared phosphine complex, and a (tetrahydrofuran), dioxane, DMF (dimethylformamide), DMA (dimethylacetamide), MeCN (acetonitrile), DMSO (dimethylsulfoxide) or combination thereof. Preferably, the solvent is THF, toluene, dioxane, MeCN or combination thereof. Most preferably, the solvent is a combination of THF and toluene.

Suitable sources of palladium may include, for example, $Pd_2(dba)_3$, $Pd(OAc)_2$, $Pd(dppf)Cl_2$, preferably the palladium source is tris(dibenzylideneacetone)-dipalladium (0).

Suitable phosphine ligand may include, for example, $PPh_3$, BINAP (2,2'-bis(diphenylphosphino)-1,1'-binaphthyl), $(Me_3Ph)_3P$ (Tris(2,4,6-trimethylphenyl)phosphine), XPhos (2-Dicyclohexylphosphino-2',4',6'-triisopropylbiphenyl), APhos ((4-(N,N-Dimethylamino)phenyl)di-tert-butyl phosphine), XantPhos (4,5-Bis(diphenylphosphino)-9,9-dimethylxanthene), BrettPhos (2-(Dicyclohexylphosphino)3,6-dimethoxy-2',4',6'-triisopropyl-1,1'-biphenyl), preferably XPhos, APhos, XantPhos, more preferably the ligand is APhos (4-(N,N-dimethylamino)phenyl)-di-tert-butylphosphine.

Suitable pre-prepared phosphine complexes may include, for example, Superstable Pd(0) catalyst, $Pd[(o-tolyl)_3P]_2$, $Pd(Ph_3P)_4$, $Pd[(c-hexyl)_3P]_2$, $Pd[(t-butyl)_3P]_2$, preferably Superstable Pd(0) catalyst, $Pd[(o-tolyl)_3P]_2$, more preferably Superstable Pd(0) catalyst $(Pd(Ar_3P)_3$ where Ar=3,5-trifluoromethyl-phenyl).

Suitable bases may include, for example, NaOtBu, KOtBu, LiHMDS (lithium bis(trimethylsilyl)amide), $Na_3PO_4$, $K_3PO_4$, $Na_2CO_3$, $K_2CO_3$, $Cs_2CO_3$, NaOH, KOH, preferably LiHMDS, NaOtBu, more preferably the base is lithium bis(trimethylsilyl)amide.

Step a) may be carried out at a temperature ranging from about 20° C. to about 100° C., preferably step a) is carried out at a temperature of from about 20° C. to about 80° C., most preferably step a) is carried out at a temperature of about 50-60° C.

Step b) is typically carried out in the presence of a suitable solvent, a suitable coupling agent, a suitable activating agent and a suitable base. Suitable solvents may include, for example, DCM, THF, toluene, NMP, DMF or combination thereof. Preferably, the solvent is Dichloromethane, THF, toluene or combination thereof. Most preferably, the solvent is Dichloromethane.

Suitable coupling agents may include, for example, EDCI (1-Ethyl-3-(3-dimethylaminopropyl)carbodiimide), DCC (N,N'-Dicyclohexylcarbodiimide), DIC (N,N'-diisopropylcarbodiimide), HBTU (N,N,N',N'-tetramethyl-O-(1H-benzotriazol-1-yl)uronium hexafluorophosphate), HATU (1-[Bis(dimethylamino)methylene]-1H-1,2,3-triazolo[4,5-b]pyridinium 3-oxid hexafluorophosphate), preferably EDCI, DIC, more preferably the coupling agent is N,N-diisopropylcarbodiimide (DIC).

Suitable activating agents may include for example DMAP (4-dimethylaminopyridine), HOBt (1-hydroxybenzotriazole), HOAt (1-hydroxy-7-azabenzotriazole, preferably DMAP, HOBt, most preferably the activating agent is DMAP.

Suitable bases may include for example-triethylamine, Hünig's base, tributylamine, preferably triethylamine, Hünig's base, most preferably the base is triethylamine.

Step b) involves reacting the compound of formula 2 with the compound of formula 3 to form Venetoclax. In this reaction, the compound of formula 2 can be in the form of the free base, or an acid addition salt, preferably wherein the acid addition salt is a trifluoroacetate salt or a sulfate salt. The compound of formula 3 and the compound of formula 2 are reacted in approximately 1:1 molar ratio, calculated with respect to the free base of both compounds. For example, when the compound of formula 2 is used in the form of an acid addition salt, the reaction may be conducted in the presence of a base, such as an organic base (e.g. an organic amine base such as a trialkylamine base) in order to liberate the free base. The same base may also be used for regenerating the activating agent. The base is therefore preferably added in an excess amount relative to the organic acid present in the compound of formula 2 (e.g. about 2 to about 4 equivalents).

Step b) may be carried out at a temperature ranging from about 20° C. to about 100° C., preferably step b) is carried out at a temperature of from about 20° C. to about 60° C., most preferably step b) is carried out at a temperature of about 20 to about 40° C., or about 20 to about 30° C.

In another embodiment, the above process further comprises the generation of compound of formula 5 by a process that comprises:
i) reacting compound of formula 7c and compound of formula 8 to obtain the compound of formula 6c; and
ii) hydrolyzing the compound of formula 6c to obtain compound of formula 5;
wherein the compound of formula 6c is not isolated.

Step i) is typically performed in the presence of a suitable solvent and a suitable base. Suitable solvents may include, for example, DMF, DMA, MeCN, toluene, NMP (N-methylpyrrolidone) or combination thereof. Preferably, the solvent is N,N-dimethylformamide, acetonitrile, DMA or combination thereof. Most preferably, the solvent comprises N,N-dimethylformamide and acetonitrile.

Suitable bases may include for example alkali carbonates, phosphates, hydrogenphosphates, hydroxides, preferably alkali phosphates, most preferably the base is $K_3PO_4$.

Step i) may be carried out at a temperature ranging from about 20° C. to about 110° C., preferably step i) is carried out at a temperature of from about 50° C. to about 100° C., most preferably step i) is carried out at a temperature of about 75° C. to about 95° C.

Step ii) is typically performed in the presence of a suitable base. Suitable bases may include for example alkali carbonates, phosphates, hydrogenphosphates, hydroxides preferably alkali hydroxides, most preferably the base is NaOH.

Step ii) may be carried out at a temperature ranging from about 20° C. to about 110° C., preferably step ii) is carried out at a temperature of from about 40° C. to about 90° C., most preferably step ii) is carried out at a temperature of about 55° C. to about 75° C.

In an alternative embodiment, compound 5 may be generated by a process that comprises:
  i) reacting compound of formula 7a and compound of formula 8 to obtain the compound of formula 6a; and
  ii) hydrolyzing the compound of formula 6a to obtain compound of formula 5;

Step i) is typically performed in the presence of a suitable solvent and a suitable base. Suitable solvents may include, for example, DMF, DMA, MeCN, toluene, NMP or combination thereof. Preferably, the solvent is N,N-dimethylformamide, acetonitrile, DMA or combination thereof. Most preferably, the solvent comprises N,N-dimethylformamide and acetonitrile.

Suitable bases may include for example alkali carbonates, phosphates, hydrogenphosphates, hydroxides, preferably alkali phosphates, most preferably the base is $K_3PO_4$.

Step i) may be carried out at a temperature ranging from about 20° C. to about 110° C., preferably step i) is carried out at a temperature of from about 50° C. to about 100° C., most preferably step i) is carried out at a temperature of about 75° C. to about 95° C.

Step ii) is typically performed in the presence of a suitable solvent and suitable base. Suitable solvents may include, for example, THF, dioxane, DMF, MeCN, toluene, MTBE (methyl t-butyl ether) or combination thereof. Preferably, the solvent is THF, dioxane or combination thereof. Most preferably, the solvent is THF.

Suitable bases may include for example alkali tert-butoxides, hydroxides, alkali hydrides, preferably alkali tert-butoxides, and hydroxides, and most preferably the base is sodium tert-butoxide.

Step ii) may be carried out at a temperature ranging from about 20° C. to about 110° C., preferably step ii) is carried out at a temperature of from about 40° C. to about 90° C., most preferably step ii) is carried out at a temperature of about 55° C. to about 65° C.

In a most preferred embodiment the disclosure provides a process for the preparation of Venetoclax that comprises the following steps:
  a) reacting compound of formula 7c and compound of formula 8 in the presence of $K_3PO_4$ to obtain the compound of formula 6c; and
  b) hydrolyzing the compound of formula 6c in the presence of NaOH to obtain compound of formula 5; wherein the compound of formula 6c is not isolated;
  c) reacting a compound of formula 5, with a compound of formula 4, in the presence of Lithium bis(trimethylsilyl)amide to provide compound of formula 2;
  d) isolating compound of formula 2 in free base form, or as acid salt, for example, preferably a mono or diacid salt such as monohydrogen phosphate, dihydrogen phosphate, HCl, TFA or $H_2SO_4$, more preferably isolating compound 2 as a sulfate salt (2a) or a TFA salt (2b); and
  e) reacting the compound of formula 2 or the acid salt thereof with compound of formula 3 to afford Venetoclax (compound 1).

In another aspect, the present disclosure provides a novel intermediate of formula 5 that can be advantageously used in the preparation of Venetoclax:

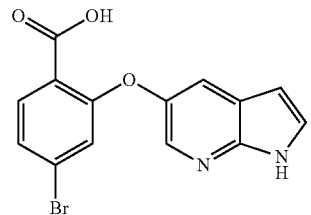

5

In another embodiment the disclosure provides use of compound of formula 5 for the preparation of Venetoclax. In a further embodiment the disclosure provides for compound 5 for use in the preparation of Venetoclax.

In a preferred embodiment compound 5 may be crystalline.

Figure 23:
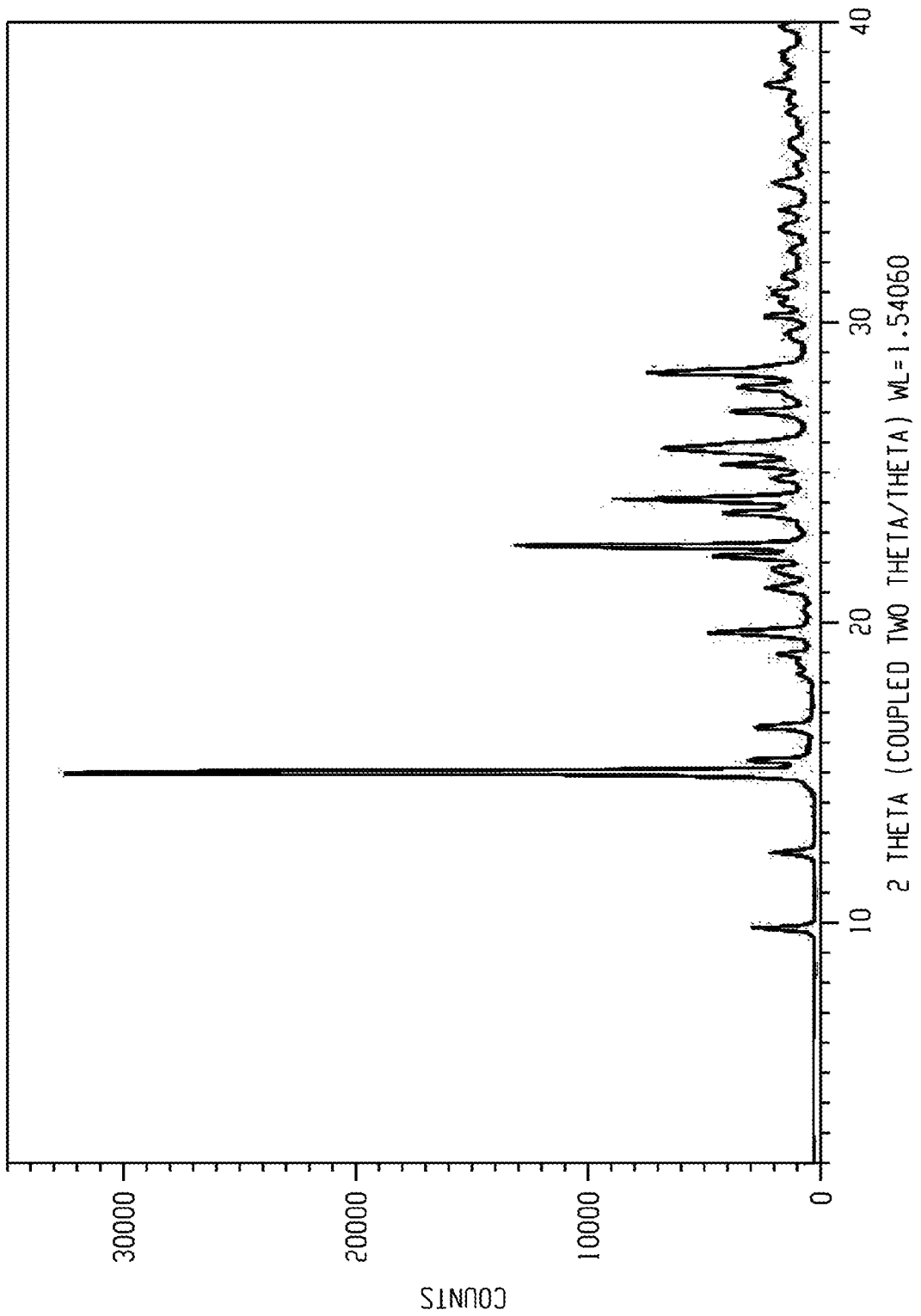
FIG. 23 shows a characteristic X-ray powder diffraction pattern of form alpha of compound 5.

In another aspect, the present disclosure comprises a crystalline form of compound 5, designated form alpha. The crystalline form alpha of compound 5 may be characterized by data selected from one or more of the following: an X-ray powder diffraction pattern substantially as depicted in FIG. 23; an X-ray powder diffraction pattern having peaks at 9.8, 15.0, 19.6, 27.0 and 28.3 degrees two theta±0.2 degrees two theta; and combinations of these data.

Crystalline form alpha of compound 5 may be further characterized by an X-ray powder diffraction pattern having peaks as described above and also having any one, two, three, four, five or six additional peaks selected from 12.3, 16.5, 21.1, 22.5, 23.6 and 24.1 degrees two theta±0.2 degrees two theta.

Crystalline form alpha of compound 5 may be characterized by each of the above characteristics alone/or by all possible combinations.

In one embodiment of the present disclosure, crystalline form alpha of compound 5 is isolated.

In another embodiment of the present disclosure, crystalline form alpha of compound 5 is polymorphically pure.

Figure 24:
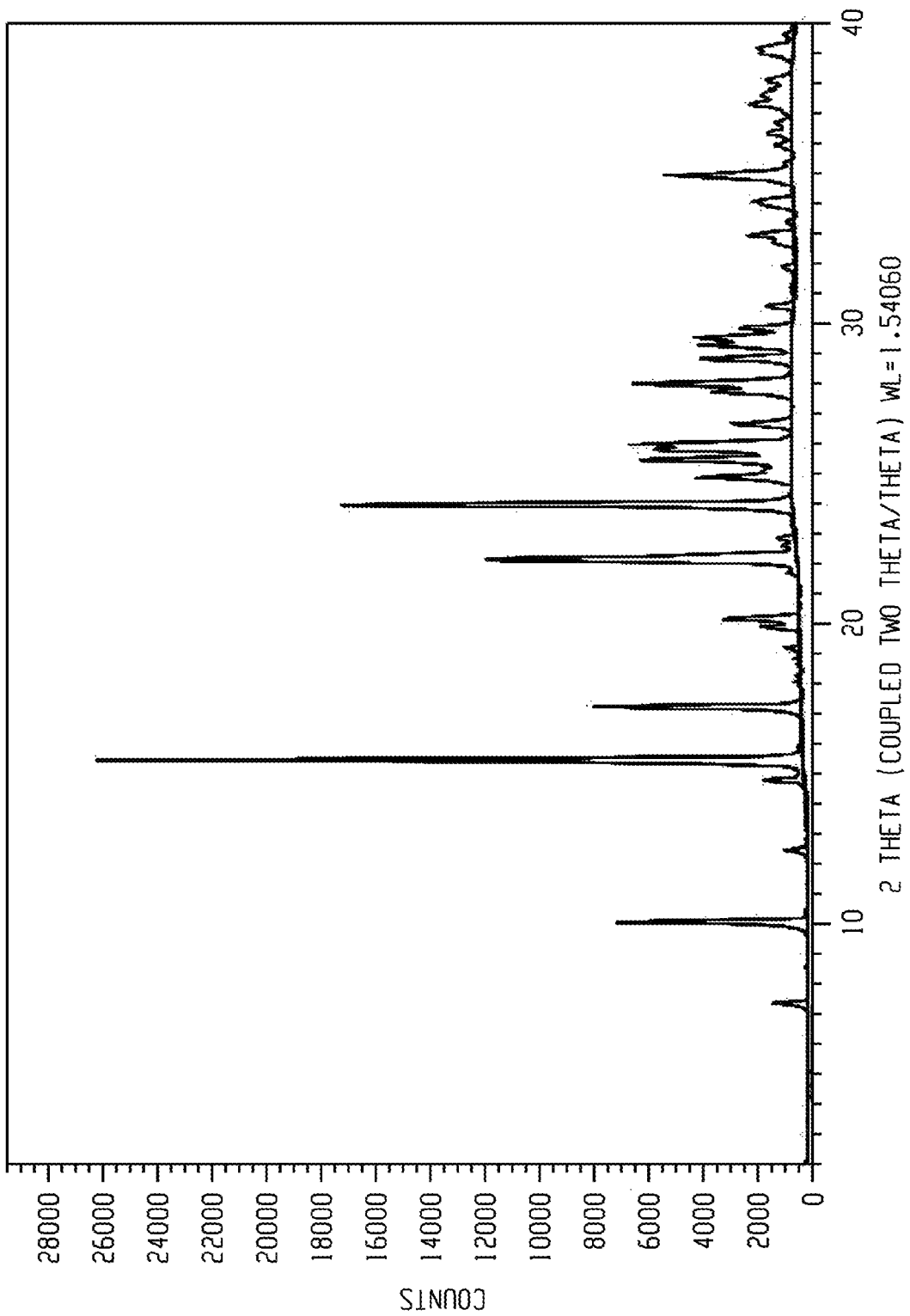
FIG. 24 shows a characteristic X-ray powder diffraction pattern of form beta of compound 5.

In another aspect, the present disclosure comprises a crystalline form of compound 5, designated form beta. The crystalline form beta of compound 5 may be characterized by data selected from one or more of the following: an X-ray powder diffraction pattern substantially as depicted in FIG. 24; an X-ray powder diffraction pattern having peaks at 10.1, 15.5, 17.3, 20.2 and 28.9 degrees two theta±0.2 degrees two theta; and combinations of these data.

Crystalline form beta of compound 5 may be further characterized by an X-ray powder diffraction pattern having peaks as described above and also having any one, two, three, four, five or more additional peaks selected from 7.4, 14.8, 22.2, 24.0, 25.5, 26.7 and 28.0 degrees two theta±0.2 degrees two theta.

Crystalline form beta of compound 5 may be characterized by each of the above characteristics alone/or by all possible combinations.

In one embodiment of the present disclosure, crystalline form beta of compound 5 is isolated.

In another embodiment of the present disclosure, crystalline form beta of compound 5 is polymorphically pure.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("PXRD") Method

BRUKER D8 Advance X-ray powder diffractometer, CuKα radiation (λ=1.5418 Å); Lynxeye XE detector, low amount PMMA sample holder with zero background plate was used. Prior to analysis, the dry samples were gently ground by means of mortar and pestle in order to obtain a fine powder. The ground sample was adjusted into a cavity of the sample holder and the surface of the sample was smoothed by means of a cover glass.

Measurement parameters:
Sample: Spin mode, rotation speed 30 rpm;
Scan range: 2-40 degrees 2-theta;
Scan mode: continuous;
Step size: 0.05±0.005 degrees;
Time per step: 0.5 sec;
Divergence slit: V20

The accuracy of peak positions is defined as +0.2 degrees two theta due to experimental differences like instrumentations, sample preparations etc.

FT-IR Spectroscopy

Perkin-Elmer Spectrum One FT-IR Spectrometer, at 4 cm$^{-1}$ resolution with 16 scans, in the range of 4000-400 cm$^{-1}$. Samples were analyzed in Nujol mull. The spectra were recorded using an empty cell as a background.

$^{13}$C NMR Method

Solid state CP/MAS 13C NMR spectra were recorded with variable amplitude cross polarization, magic angle spinning and high power proton decoupling using BRUKER Avance II+ spectrometer operating at 125 MHz and 303 K used for the measurement. A probe using 4 mm i.d. zirkonia rotors was employed. The operation conditions were acquisition time 27 µs, pre-scan-delay 6.5 s, number of scans 2048, and spin rate 11 kHz. Chemical shifts were referenced via a replacement sample of glycine (carboxyl carbon chemical shift assigned as 176.03 ppm relative to the signal of tetramethylsilane).

EXAMPLES

Example 1. Preparation of Venetoclax

Venetoclax was prepared according to the following scheme 1 below, which are illustrated by the following Procedures 1-10). In any of Procedures 1-10, the sulfonamide compound (3) can be reacted with either the free base of the benzoic acid derivative (compound 2) or its corresponding sulfate salt (compound 2a) or trifluoroacetic acid salt (compound 2b). For example, Procedures 1-8 may be carried out with the trifluoroacetic acid salt of the benzoic acid derivative (i.e. compound 2b).

Scheme 1

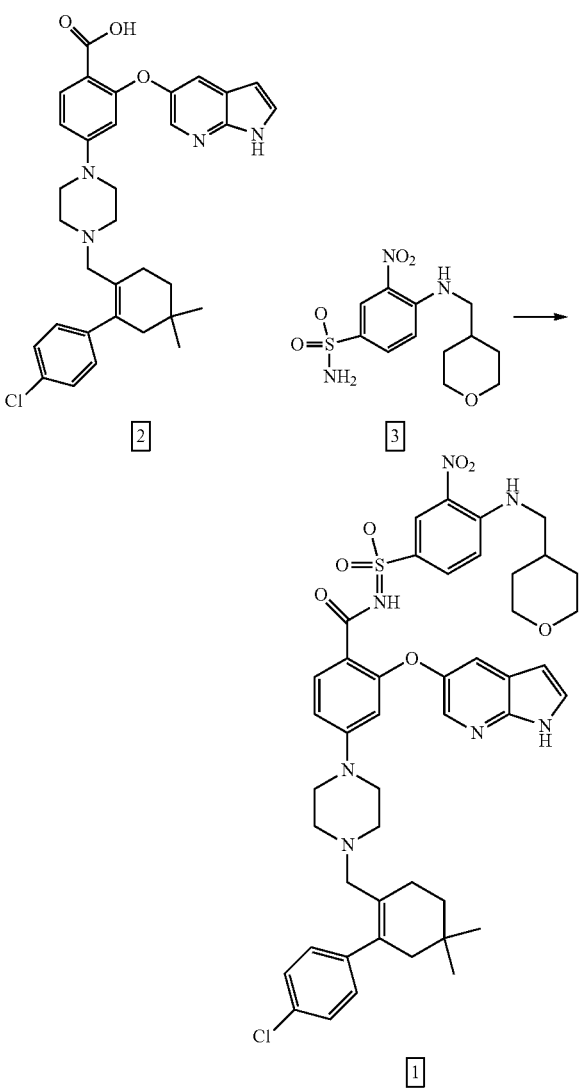

A. Procedure 1

The sulfonamide (compound 3, 10.17 g; 32 mmol), DMAP (1.26 g, 3 mmol), EDCI (10.09 g, 52 mmol) and dichloromethane (226 mL) were combined at room temperature (flask I). In a second flask (flask II), the benzoic acid derivative (compound 2, 20 g, 33 mmol), Et$_3$N (9 mL) and dichloromethane (90 mL) were combined and stirred for 15 minutes. The resulting acid solution (flask II) was slowly added to the suspension of the sulfonamide (flask I) within 30 minutes and agitated until reaction completion (after ~4 h an orange solution resulted). After 22 hours N,N-dimethylethylenediamine (8.6 mL) was then charged to the reaction mixture, stirring was continued for another 1.5 hours. The reaction mixture was washed with 10% acetic acid solution twice (2×140 mL). The lower organic layer was diluted with more dichloromethane (60 mL) and methanol (10 mL), before separation of the organic layer. After phase separation the organic layer was washed with 5% NaHCO$_3$ aq (140 mL) and then with 5% NaCl solution (140 mL) at room temperature. The lower organic layer was separated and the concentrated to dryness, resulting a yellow solid. Dichloromethane (205 mL) and methanol (21 mL) were added, the suspension was heated to 38° C. under stirring. Ethyl acetate (184 mL) was added slowly within 30 minutes to the yellow solution. Heating was turned off and the suspension was cooled to room temperature and kept in a refrigerator (2-8° C.) over-weekend. The filtrated product was washed with mix of EtOAc-dichloromethane 1-1 twice (2×52 mL). The product was dried under vacuum at 50° C. and 100 mbar 5 hours to yield Venetoclax as yellow solid (10.84 g, 39%, HPLC purity: 93.80 A %).

B. Procedure 2

The sulfonamide (compound 3, 10.17 g, 32.2 mmol), DMAP (8.4 g, 68.7 mmol), EDCI (10.1 g, 52.7 mmol) and dichloromethane (240 mL) were combined at room temperature (flask I). In a second flask (flask II), the benzoic acid derivative (compound 2, 20 g, 35.0 mmol), Et$_3$N (9 mL) and dichloromethane (90 mL) were combined and stirred for 15 minutes. The resulting acid solution (flask II) was slowly added to the suspension of the sulfonamide (flask I) within 30 minutes (after ~1 hour a brown solution resulted) and reaction mixture agitated until reaction completion. After 20 hours N,N-dimethylethylenediamine (8.6 mL) was then charged to the reaction mixture, stirring was continued for another 1.5 hours. The reaction mixture was washed with 10% acetic acid solution twice (2×140 mL). The lower organic layer was diluted with more dichloromethane (60 mL) and methanol (10 mL), before separation of the organic layer. After phase separation the organic layer was washed with 5% aq. NaHCO$_3$ (140 mL) and then with 5% NaCl solution (140 mL) at room temperature. The lower organic layer was separated and the concentrated to dryness, resulting a yellow solid. Dichloromethane (205 mL) and methanol (21 mL) were added, the suspension was heated to 38° C. under stirring. Ethyl acetate (184 mL) was added slowly within 30 minutes to the yellow solution. Heating was turned off and the suspension was cooled to room temperature and kept in a refrigerator (2-8° C.) overnight. The filtrated product was washed with mixture of EtOAc-dichloromethane 1-1 twice (2×52 mL). The product was dried under vacuum (~100 mbar) at 50° C. overnight to yield Venetoclax as yellow solid (9.78 g, 35%, HPLC purity: 97.74 A %).

C. Procedure 3

The sulfonamide (compound 3, 10.81 g, 34.3 mmol), DMAP (8.42 g, 68.9 mmol), EDCI (8.61 g, 44.9 mmol) and dichloromethane (250 mL) were combined at room temperature (flask I). In a second flask (flask II), the benzoic acid derivative (compound 2, 20 g, 35.0 mmol), Et$_3$N (9.5 mL) and dichloromethane (200 mL) were combined and stirred for 15 minutes. The resulting acid solution (flask II) was slowly added to the suspension of the sulfonamide (flask I) within 150 minutes and reaction mixture agitated until reaction completion. After 21 hours the reaction mixture was washed with 10% acetic acid solution twice (2×93 mL). The lower organic layer was diluted with more dichloromethane (40 mL) and methanol (6.6 mL), before separation of the organic layer. After phase separation the organic layer was washed with 5% aq. NaHCO$_3$ (93 mL) and then with 5% NaCl solution (93 mL) at room temperature. The lower organic layer was separated and the concentrated to dryness, resulting a yellow solid. Dichloromethane (137 mL) and methanol (14 mL) were added, the suspension was heated to 38° C. under stirring. Ethyl acetate (123 mL) was added slowly within 45 minutes to the yellow solution. Heating was turned off and the suspension was cooled to ~0-5° C. and stirred for 2 hours. The filtrated product was washed with cold EtOAc (50 mL). The product was dried under vacuum (~60 mbar) at 50° C. overnight to yield Venetoclax as yellow solid (16.96 g; 57%, HPLC purity 96.50 A %).

D. Procedure 4

The sulfonamide (compound 3, 5.41 g; 17.16 mmol), DMAP (4.21 g, 34.36 mmol), EDCI (4.31 g; 22.48 mmol) and dichloromethane (125 mL) were combined at room temperature (flask I). In a second flask (flask II), the benzoic acid derivative (compound 2, 10 g; 17.5 mmol), Et$_3$N (4.75 mL) and dichloromethane (100 mL) were combined and stirred for 15 minutes. The resulting acid solution (flask II) was slowly added to the suspension of the sulfonamide (flask I) within 120 minutes and reaction mixture agitated until reaction completion. After 20 hours the reaction mixture was washed with 10% acetic acid solution twice (2×47 mL). The lower organic layer was diluted with more dichloromethane (20 mL) and methanol (4 mL), before separation of the organic layer. After phase separation the organic layer was washed with 5% aq. NaHCO$_3$ (47 mL) and then with 5% NaCl solution (47 mL) at room temperature. The lower organic layer was separated and then concentrated to dryness, resulting a yellow solid. Dichloromethane (68.5 mL) and methanol (7 mL) were added, the suspension was heated to 38° C. under stirring. Ethyl acetate (61.5 mL) was added slowly within 30 minutes to the yellow solution. Heating was turned off and the suspension was cooled to ~0-5° C. and stored in refrigerator overnight. The filtrated product was dried under vacuum (~60 mbar) at 50° C. overnight to yield Venetoclax as yellow solid (8.76 g; 58%, HPLC purity 93.10 A %).

E. Procedure 5

The sulfonamide (compound 3, 21.62 g; 68.56 mmol), DMAP (16.84 g, 34.36 mmol), EDCI (17.22 g; 89.83 mmol) and dichloromethane (500 mL) were combined at room temperature (flask I). In a second flask (flask II), the benzoic acid derivative (compound 2, 40 g; 70.04 mmol), Et$_3$N (19 mL) and dichloromethane (400 mL) were combined and stirred for 15 minutes. The resulting acid solution (flask II) was slowly added to the suspension of the sulfonamide (flask I) within 180 minutes and reaction mixture agitated until reaction completion. After 22 hours the reaction mixture was washed with 10% acetic acid solution twice (2×280 mL). The lower organic layer was diluted with more dichloromethane (120 mL) and methanol (20 mL), before separation of the organic layer. After phase separation the organic layer was washed with 5% aq. NaHCO$_3$ (280 mL) and then with 5% NaCl solution (280 mL) at room temperature. The lower organic layer was separated and the concentrated to dryness, resulting in a yellow solid. Dichloromethane (274 mL) and methanol (28 mL) were added, the suspension was heated to 38° C. under stirring. Ethyl acetate (250 mL) was added slowly within 40 minutes to the yellow solution. Heating was turned off and the suspension was cooled to ~0-5° C. and stored in refrigerator overnight. The filtrated product was washed with Ethyl acetate (100 ml) and dried under vacuum (~60 mbar) at 50° C. overnight to yield Venetoclax as yellow solid (35.9 g; 60.4%, HPLC purity 96.04 A %).

F. Procedure 6

The sulfonamide (compound 3, 57.8 g), DMAP (45.0 g), EDCI (46.0 g) and dichloromethane (1337 mL) were combined at 25° C. (flask I). In a second flask (flask II), the benzoic acid derivative (compound 2, 136.0 g), Et$_3$N (50.9 mL) and dichloromethane (1068 mL) were combined and stirred for 15 minutes. The resulting acid solution (flask II) was slowly added to the suspension of the sulfonamide (flask I) within 120 minutes and reaction mixture agitated until reaction completion. After 23 hours the reaction mixture was washed with 10% acetic acid solution twice (2×750 mL). After phase separation the organic layer was washed with 5% aq. NaHCO$_3$ (750 mL) and then with 5% NaCl solution (750 mL) at room temperature. The lower organic layer was separated and the concentrated to dryness, resulting a yellow solid. Dichloromethane (733 mL) and methanol (75 mL) were added, the suspension was heated to 38° C. under stirring. Ethyl acetate (670 mL) was added slowly within 40 minutes to the yellow solution. Heating was turned off and the suspension was cooled to ~0-5° C. and stirred at 5° C. overnight. The filtrated product was washed with Ethyl acetate (268 ml) and dried under vacuum (~100 mbar) at 50° C. overnight to yield Venetoclax as yellow solid (96.7 g; 60.4%, HPLC purity 91.89 A %).

G. Procedure 7

The sulfonamide (compound 3, 158.9 g), DMAP (123.7 g), EDCI (126.5 g) and dichloromethane (3678 mL) were combined at 25° C. (reactor I). In a second reactor (reactor II), the benzoic acid derivative (compound 2, 340.0 g), Et$_3$N (140 mL) and dichloromethane (2936 mL) were combined and stirred for 15 minutes. The resulting acid solution (reactor II) was slowly added to the suspension of the sulfonamide (reactor I) within 120 minutes and reaction mixture agitated until reaction completion. After 22 hours the reaction mixture was washed with 10% acetic acid solution twice (2×2056 mL). The lower organic layer was diluted with more dichloromethane (882 mL) and methanol (146 mL), before separation of the organic layer. After phase separation the organic layer was washed with 5% aq. NaHCO$_3$ (2059 mL) and then with 5% NaCl solution (2059 mL) at room temperature. The lower organic layer was separated and the concentrated to dryness, resulting a yellow solid. Dichloromethane (2014 mL) and methanol (206 mL) were added, the suspension was heated to 38° C. under stirring. Ethyl acetate (1840 mL) was added slowly within 40 minutes to the yellow solution. Heating was turned off and the suspension was cooled to ~0-5° C. and stirred at 5° C. overnight. The filtrated product was washed with Ethyl acetate (735 ml) and dried under vacuum (~100 mbar) at 50° C. overnight to yield Venetoclax as yellow solid (273.6 g; 62.5%, HPLC purity 95.36 A %).

H. Procedure 8

The sulfonamide (compound 3, 107.2 g), DMAP (83.5 g), EDCI (85.4 g) and dichloromethane (2482 mL) were combined at 25° C. (reactor I). In a second reactor (reactor II), the benzoic acid derivative (compound 2, 240 g), Et$_3$N (94.4 mL) and dichloromethane (1982 mL) were combined and stirred for 15 minutes. The resulting acid solution (reactor II) was slowly added to the suspension of the sulfonamide (reactor I) within 120 minutes and reaction mixture agitated until reaction completion. After 22 hours the reaction mixture was washed with 10% acetic acid solution twice (2×1390 mL). The lower organic layer was diluted with more dichloromethane (595 mL) and methanol (99 mL), before separation of the organic layer. After phase separation the organic layer was washed with 5% aq. NaHCO$_3$ (1390 mL) and then with 5% NaCl solution (1390 mL) at room temperature. The lower organic layer was separated and the concentrated to dryness, resulting a yellow solid. Dichloromethane (1360 mL) and methanol (139 mL) were added, the suspension was heated to 38° C. under stirring. Ethyl acetate (1241 mL) was added slowly within 40 minutes to the yellow solution. Heating was turned off and the suspension was cooled to ~0-5° C. and stirred at 5° C. overnight. The filtrated product was washed with Ethyl acetate (496 ml) and dried under vacuum (~100 mbar) at 50° C. overnight to yield as yellow solid (165.5 g; 68%, HPLC purity 94.13 A %).

I. Procedure 9

In a 100-mL flask (flask I) 2-[(1H-Pyrrolo[2,3-b]pyridine-5-yl)oxy]-4-[4-[[2-(4-chlorophenyl)-4,4-dimethylcyclohex-1-enyl]methyl]piperazin-1-yl]benzoic acid TFA salt (compound 2b) (assay: 7.45 mmol), Et$_3$N (2 mL, 14.61 mmol) and dichloromethane (43 mL) were combined at 20-25° C. and stirred for complete dissolution. In a 100-mL three necked round bottom flask (flask II) equipped with mechanical stirrer, thermometer, 3-nitro-4-[[(tetrahydropyran-4-yl)methyl]amino]-benzenesulfonamide (2.30 g, 7.31 mmol), DMAP (1.79 g, 14.68 mmol), N,N-diisopropylcarbodiimide (1.5 mL, 9.64 mmol) and dichloromethane (53 mL) were combined and stirred for 15 minutes. The resulting acid solution (flask I) was slowly added to the suspension of the sulfonamide (flask II) within 1 hour and reaction mixture agitated at 20-25° C. until reaction completion. The reaction mixture was extracted with 10% aqueous acetic acid (2×29 mL), 5% aqueous NaHCO$_3$ (29 mL) and 5% aqueous NaCl (29 mL). After phase separation the organic layer was evaporated. Yield: 80%, HPLC: 57.7 A %

Purification

The obtained material (7.63 g) was suspended in 2-butanone (152 mL) at 20-25° ° C. and stirred overnight. The slurry was filtered and the wet-cake was suspended in 2-butanone (80 mL) and stirred overnight. The slurry was filtered and the wet-cake was dried under vacuum at 60-65° C. overnight to obtain Venetoclax in 80% yield. HPLC: 97.7 A %

Recrystallization

To a solution of purified Venetoclax (2.87 g in THF (36 mL) cyclohexane (14 mL) was added at 60-65° C. and the mixture is cooled to 20-25° C. to precipitate Venetoclax. The slurry was filtered and the wet-cake was dried at 40-45° C. for 3 days to obtain purified Venetoclax in 86% yield (HPLC purity: 98.7 A %).

J. Procedure 10

In a 100-mL flask (flask I) 2-[(1H-Pyrrolo[2,3-b]pyridine-5-yl)oxy]-4-[4-[[2-(4-chlorophenyl)-4,4-dimethylcyclohex-1-enyl]methyl]piperazin-1-yl]benzoic acid sulfate salt (compound 2a) (assay: 14.88 mmol), Et$_3$N (12 mL, 87.5 mmol) and dichloromethane (85 mL) were combined at 20-25° C. and stirred for complete dissolution. In a 250-mL three necked round bottom flask (flask II) equipped with magnetic stirrer, thermometer, 3-nitro-4-[[(tetrahydropyran-4-yl)methyl]amino]-benzenesulfonamide (4.60 g, 14.58 mmol), DMAP (7.12 g, 58.34 mmol), N,N-diisopropylcarbodiimide (6 mL, 38.5 mmol) and dichloromethane (106 mL) were combined and stirred for 15 minutes. The resulting acid solution (flask I) was slowly added to the suspension of the sulfonamide (flask II) within 1 hour and reaction mixture agitated at 35-40° C. until reaction completion. The reaction mixture was extracted with 10% aqueous acetic acid (2×57 mL), 5% aqueous NaHCO$_3$ (57 mL) and 5% aqueous NaCl (57 mL). After phase separation the organic layer was evaporated. Yield: 55%

Example 2. Preparation of Form 1 of Venetoclax 250 mg of Venetoclax prepared according to procedure 2 of example 1 was suspended in 5 ml MIBK, and stirred in a closed vial with magnetic stirrer at 50° C., for 3 weeks, with ~500 rpm.

After 3 weeks it was filtered and the wet material obtained was analyzed by XRD.

Half of the sample was dried overnight at ambient conditions (atmospheric pressure, at 23° C.).

The obtained wet and dry (HPLC purity: 99.44 A %) samples were analyzed by XRPD. The wet and dry samples obtained were identified as form 1.

The XRPD of the dry sample is presented in FIG. 1.

Example 3. Preparation of Form 2a of Venetoclax

A. Procedure 1

450 mg of Venetoclax prepared according to procedure 3 of example 1 was dissolved in 25 ml ethyl acetate at reflux temperature, 25 ml cyclohexane was dropped in at 70° C. The solution was cooled down to 24° C., meanwhile crystallization of the product occurred (at ~54° C.). The suspension was stirred at 24° C. for one night, with ~300 rpm and filtered.

The obtained wet material was analyzed by XRPD and the XRPD pattern is presented in FIG. 2.

B. Procedure 2

1 g of Venetoclax prepared according to procedure 5 of example 1 was dissolved in 100 ml acetone at reflux temperature, 150 ml cyclohexane was dropped in at 50° C. The solution was cooled down to 5° C., meanwhile crystallization of the product occurred (at ~10° C.). The suspension was stirred at 5° C. for one night, with ~120 rpm and filtered.

The obtained wet material was analyzed by XRPD and the polymorphic form was identified as form 2a.

Example 4. Preparation of Form 2 of Venetoclax

A. Procedure 1

One part of wet material obtained in procedure 1 of example 3 was dried overnight at ambient conditions (atm. pressure, 24° C.). The obtained dry material was analyzed by XRPD and the XRPD pattern is presented in FIG. 3.

B. Procedure 2

Another part of the wet material obtained in procedure 1 of example 3 was dried overnight in vacuum, at 40° C. The obtained dry material was analyzed by XRPD and identified as form 2.

C. Procedure 3

One part of wet material obtained in procedure 2 of example 3 was dried overnight at ambient conditions (atm. pressure, 24° C.). The obtained dry material was analyzed by XRPD and the polymorphic form was identified as form 2.

D. Procedure 4

Another part of the wet material obtained in procedure 2 of example 3 was dried overnight under vacuum, at 40° C. The obtained dry material (HPLC purity: 97.46 A %) was analyzed by XRPD; the polymorphic form was identified as form 2.

E. Procedure 5

To solution of 110 g of Venetoclax in 1375 ml of THF, 550 ml of cyclohexane was added at 60-65° C. and the stirred mixture was cooled to 20-25° C. in 3 hours to form a suspension and stirred overnight. The suspension was filtered and the wet cake was washed twice with cyclohexane (each with 550 ml of cyclohexane). The resulting form 2a of Venetoclax was dried under vacuum at 80° C. for 6 days followed by further drying at 94° C. for 7 days. The obtained product was analyzed by XRPD and the XRPD pattern is presented in FIG. 20.

Example 5. Preparation of Form 3 of Venetoclax 450 mg of Venetoclax prepared according to procedure 3 of example 1 was dissolved in 25 ml ethyl acetate at reflux temperature and 25 ml toluene was dropped in at 70° C. The solution was cooled down to 24° C. and stirred for one night with ~300 rpm on a magnetic stirrer. Small amount of crystalline substance was observed. Further 25 ml toluene was dropped in at 24° C., and the suspension was cooled to 5° C. After one night it was filtered.

The obtained wet material was analyzed by XRPD and the XRPD pattern is presented in FIG. 4.

Example 6. Preparation of Form 4 of Venetoclax

The material obtained in example 5 was dried overnight at ambient conditions (atm. pressure, 24° C.). The obtained dry material was analyzed by XRPD and the XRPD pattern is presented in FIG. 5.

Example 7. Preparation of Form 5 of Venetoclax 250 mg of Venetoclax prepared according to procedure 1 of example 1 was suspended in 5 ml solvent mixture (THF:water=4:1), and stirred in a closed vial with magnetic stirrer at 23° C. The starting material was dissolved after 15-20 minutes, and recrystallized immediately after 45-60 minutes. The suspension was stirred for 5 days, with ~500 rpm.

After 5 days it was filtered and dried overnight at ambient conditions (atmospheric pressure, at 23° C.). The obtained dry material (HPLC purity: 98.73 A %) was analyzed by XRPD and the XRPD pattern is presented in FIG. 6.

Example 8. Preparation of Form 6 of Venetoclax 1.55 g of Venetoclax prepared according to procedure 4 of example 1 was suspended in 31 ml MIBK, and stirred in a closed vial with magnetic stirrer at 50° C., for 5 days, with ~500 rpm. It was filtered and dried overnight under vacuum, at 40° C.

Figure 7:
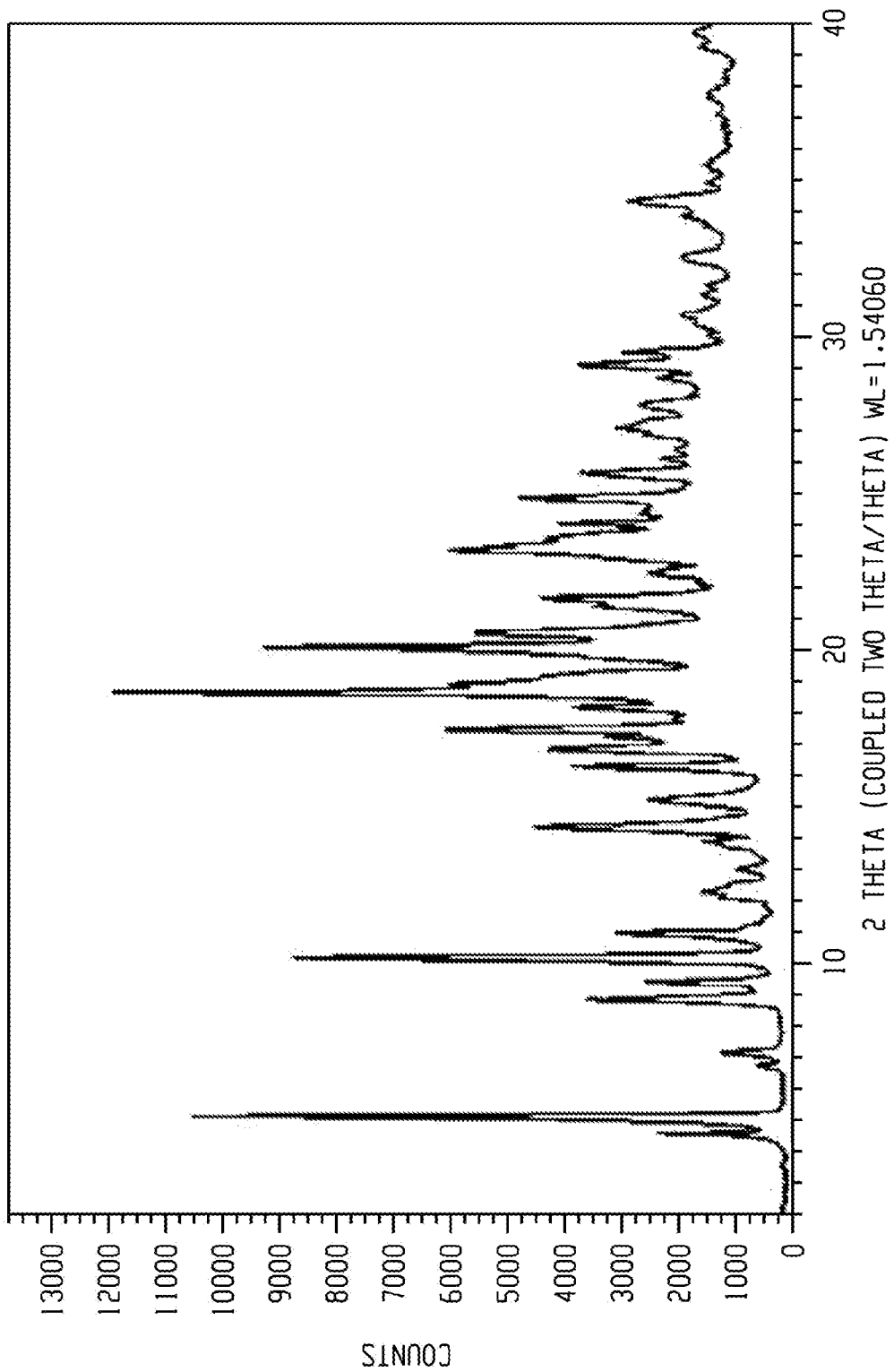
FIG. 7 shows an X-ray powder diffraction of the product obtained by example 8, comprising form 6 of Venetoclax.

The obtained dry (HPLC purity: 98.68 A %) sample was analyzed by XRPD and the XRPD pattern is presented in FIG. 7.

Example 9. Preparation of Form 7 of Venetoclax 2 g of Venetoclax prepared according to procedure 6 of example 1 was dissolved in 10 ml n-propyl acetate at reflux temperature. The solution was cooled down to 28° C. and stirred for half an hour and it was filtered.

The obtained wet material was analyzed by XRPD and the XRPD pattern is presented in FIG. 8.

Example 10. Preparation of Form 8 of Venetoclax

The material obtained in example 9 was dried at 60° C. under vacuum for 66 hours. The obtained dry material (HPLC purity: 95.73 A %) was analyzed by XRPD and the XRPD pattern is presented in FIG. 9.

Example 11. Preparation of Form 9 of Venetoclax 2 g of Venetoclax prepared according to procedure 6 of example 1 was suspended in 20 ml dimethyl carbonate at room temperature and it was stirred one hour. After one hour the solid material was filtered and the obtained wet material was analyzed by XRPD and the XRPD pattern is presented in FIG. 10.

Example 12. Preparation of Form 10 of Venetoclax

A. Procedure 1

25 ml 1,4-Dioxane was added to 2 g of Venetoclax prepared according to procedure 6 of example 1 and the mixture was heated to 40-60° C. Stirring continued at this temperature, then the mixture was cooled to 10-15° C. Solid material was isolated by filtration and dried at 20-25° C. on filter.

One portion of solid material was analyzed by XRPD and was identified as form 10. Material was further washed with water and dried at 20-25° C. on filter. The solid material was analyzed again by XRPD and was identified as form 10.

Another portion of the material was further washed with water and dried at 75-85° C. on filter. The solid material was analyzed by XRPD and the XRPD pattern is presented in FIG. 11.

B. Procedure 2

25 ml 1,4-Dioxane was added to 2 g of Venetoclax prepared according to procedure 6 of example 1 and the mixture was heated to 40-60° C., followed by the addition of 75 ml cyclohexane (75 V/V % of cyclohexane). The suspension was cooled to 10-15° C. Solid material was isolated by filtration.

One portion of the wet material was dried at 20-25° C. on filter and was analyzed by PXRD and identified as Form 10.

Another portion of the wet material was washed with water followed by drying at 20-25° C. on filter and was analyzed by XRPD and identified as Form 10.

A third portion of the wet material was dried at 75-85° C. in vacuum and was analyzed by XRPD and identified as Form 10.

C. Procedure 3

25 ml 1,4-Dioxane was added to 2 g of Venetoclax prepared according to procedure 6 of example 1 and the mixture was heated to 40-60° C., followed by the addition of 100 ml cyclohexane (80 V/V % of cyclohexane). The suspension was cooled to 10-15° C. Solid material was isolated by filtration.

One portion of the wet material was dried at 20-25° C. on filter and was analyzed by PXRD and identified as Form 10.

Another portion of the wet material was washed with water followed by drying at 20-25° C. on filter and was analyzed by XRPD and identified as Form 10.

A third portion of the wet material was dried at 75-85° C. in vacuum and was analyzed by XRPD and identified as Form 10.

D. Procedure 4

40 ml 1,4-Dioxane was added to 2 g of Venetoclax prepared according to procedure 6 of example 1 and the mixture was stirred at 20-25° C. Solid material was isolated by filtration, and 25 ml 1,4-dioxane was added to the wet material. The mixture was heated to 65-75° C. until dissolution, then the mixture was cooled to 20-25° C. Solid material was isolated by filtration and dried at 20-25° C. on filter. The solid material was analyzed by XRPD and identified as Form 10.

Example 13. Preparation of Form 11 of Venetoclax

A. Procedure 1

25 ml 1,4-Dioxane: isobutyl acetate 40:60 solvent mixture was added to 2 g of Venetoclax prepared according to procedure 7 of example 1 and the mixture was heated to 70-80° C. 100 ml isobutyl acetate was added to the suspension, and stirring was continued at 75-80° C. for 10 minutes. The solution was cooled to 45-50° C., seeded with seeds prepared according to example 14. The mixture was further cooled to 12-16° C. Solid material was isolated by filtration and was analyzed by PXRD and identified as Form 11.

One portion of the wet material was dried at 20-25° C. on filter. The solid material was analyzed by PXRD and identified as Form 11.

Another portion of the wet material was washed with water and then dried on filter at 20-25° C., and was analysed by PXRD and identified as Form 11.

A third portion of the wet material was dried at 75-85° C. on filter. The solid material was analyzed by PXRD and the XRPD pattern is presented in FIG. 12.

B. Procedure 2

2 g of Venetoclax prepared according to procedure 7 of example 1 was dissolved in 80 ml isobutyl acetate at 90° C. The solution was cooled down to 5° C. over 6 hours and stirring was continued at 5° C. overnight. The solid material was filtered and the wet material was analyzed by XRPD and identified as Form 11.

One portion of the wet material was dried at 20-25° C. on filter. The solid material was analyzed by XRPD and identified as Form 11.

Another portion of the wet material was washed with cold water (7 ml) and then dried in vacuum at 80° C. overnight and was analyzed by XRPD and identified as Form 11.

A third portion of the wet material was dried at 80° C. in vacuum and the solid material was analyzed by XRPD and identified as Form 11.

C. Procedure 3

2 g of Venetoclax prepared according to procedure 7 of example 1 was dissolved in 105 ml diethyl carbonate at 90° C. The solution was cooled down to 5° C. over 6 hours and stirring was continued at 5° C. overnight. The solid material was filtered and the wet material was analyzed by XRPD and the XRPD pattern corresponds to Form 11.

One portion of the wet material was dried at 20-25° C. on filter. The solid material was analyzed by XRPD—Form 11.

Another portion of the wet material was washed with cold water (7 ml) and then dried in vacuum at 80° C. overnight and was analyzed by XRPD and identified as Form 11.

A third portion of the wet material was dried at 80° C. in vacuum and the solid material was analyzed by XRPD and identified as Form 11.

D. Procedure 4

100 ml isobutyl acetate was added to 2 g of Venetoclax prepared according to procedure 7 of example 1 and the mixture was stirred and heated to 48-52° C. The suspension was cooled to 20-25° C., and solid material was isolated by filtration. The Wet material was dried at 20-25° C. on filter and was analyzed by PXRD and identified as Form 11.

Figure 13:
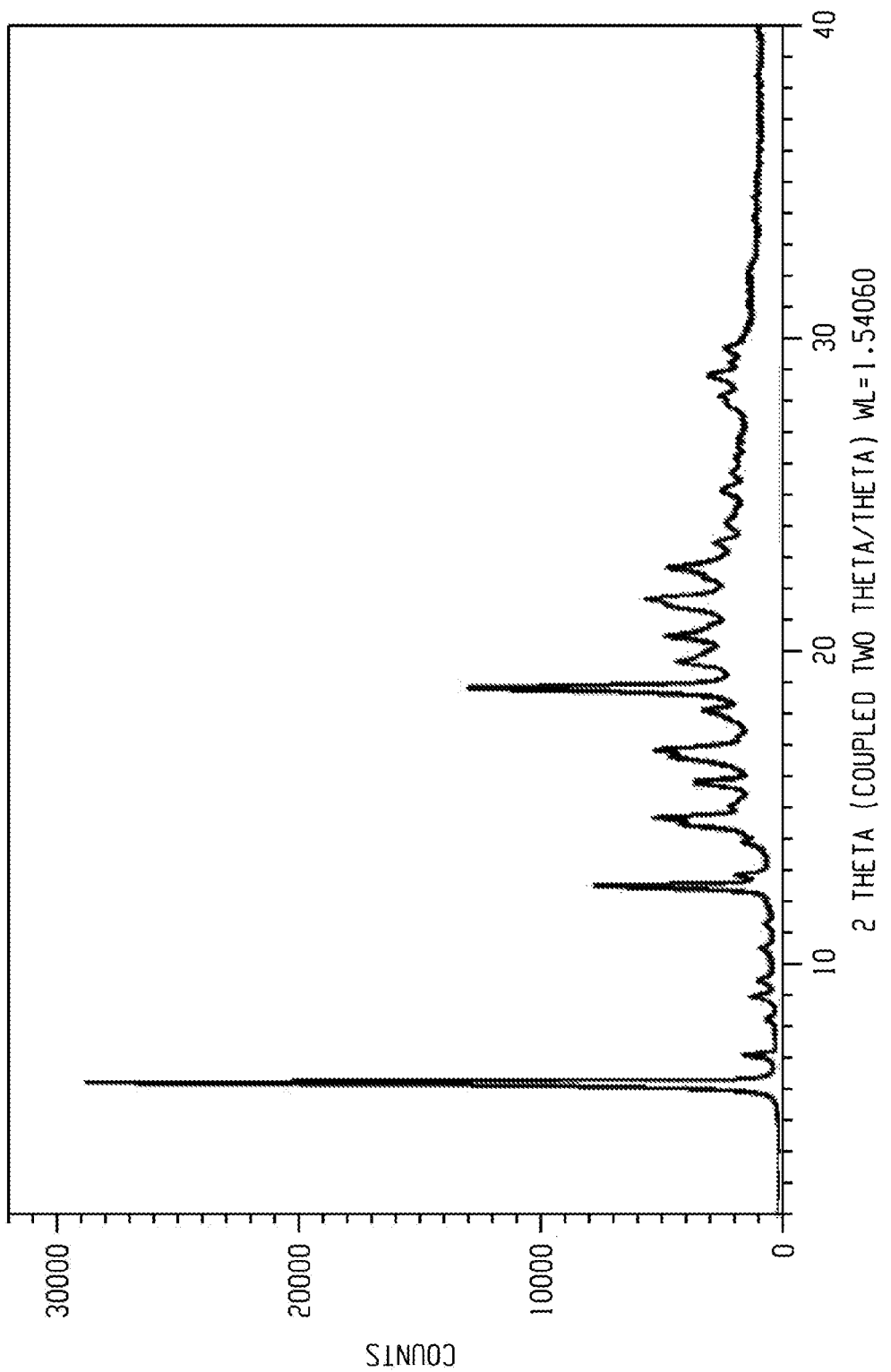
FIG. 13 shows a characteristic X-ray powder diffraction pattern of Venetoclax obtained by example 14.

Example 14. Preparation of Venetoclax Seeds 20.01 g of Venetoclax was dissolved in 500.0 ml dichloromethane at reflux temperature. The warm solution was filtered and the filtrate cooled down to 25° C. The solution was concentrated to half volume and the obtained slurry was stirred at 20° C. overnight. The solid material was filtered and washed with ethyl acetate (27 ml). The obtained wet material was dried with N2 flow at 28° C. overnight. The dry material (14.64 g; 73%; HPLC purity: 97.73 A %) was analyzed by XRPD and the XRPD pattern is presented in FIG. 13.

Example 15. Preparation of Form 12 of Venetoclax 2500 ml dioxane was added to 200 g of Venetoclax prepared according to procedure 7 of example 1 and the mixture was heated to 50° C. The mixture was stirred at 50° C. for one hour and it was cooled to 15° C. over 4 hours. Stirring was continued at 15° C. for one night. The solid material was isolated by filtration and it was washed with dioxane (125 ml). The wet material was analyzed by PXRD and identified as form 12.

Example 16. Preparation of Form 13 of Venetoclax 2 g of Venetoclax form 10 was dissolved at 80-85° C. in 25 ml dimethyl carbonate. To the resulted suspension 75 ml cyclohexane was added and was stirred at 82-85° C. The suspension was cooled to 10° C. Stirring was continued at 10° C. Solid material was isolated by filtration. Wet material was dried and was analyzed by PXRD and identified as form 13.

Example 17. Preparation of Form 14 of Venetoclax 25 ml dioxane was added to 2 g of Venetoclax prepared according to procedure 6 of example 1 and the mixture was heated to 65-70° C. 75 ml ethyl acetate was added to the mixture at 65-70° C. The mixture was cooled to 10-15° C., and 80 ml water was added. Stirring was continued at 10-15° C. for 19 hours. Solid material was isolated by filtration. Wet material was analyzed by PXRD and identified as Form 14.

Example 18. Preparation of Form 15 of Venetoclax 33.6 ml Dichloromethane and 3.4 ml methanol was added to 9.6 g of Venetoclax prepared according to procedure 8 of example 1 and the mixture was heated to 38° C. The mixture was stirred at 38° C. for half an hour and 30.7 ml ethyl acetate was added at this temperature over 40 minutes. It was cooled to 5° C. over one hour. Stirring was continued at 5° C. for one night. Solid material was isolated by filtration. 192 ml Methyl ethyl ketone (MEK) was added to the isolated compound and the mixture was heated to 50° C. The mixture was stirred at 50° C. for 2 hours and it was cooled to 15° C. over 2 hours. Stirring was continued at 15° C. at least one night. Solid material was isolated by filtration. Wet material was analyzed by PXRD and identified as form 15.

Example 19. Preparation of Compound 5

A. Procedure 1
Step 1—Preparation of Compound 6b
In a 10-L reactor equipped with mechanical stirrer, thermometer and condenser, charged 5-hydroxy-7-azaindole (compound 8, 97.5 g, 0.73 mol), tert-butyl 4-bromo-2-fluorobenzoate (compound 7b, 200 g, 0.73 mol), N,N-dimethylformamide (1.4 L) and acetonitrile (1.4 L). The mixture was stirred at 20-25° C. for ~15 minutes (until complete dissolution). The solution was treated with K3PO4 (216 g, 1.02 mol, 1.4 equiv) at 20-25° C. The reaction mixture (suspension was heated and stirred for 24 h at 90-95° C. then cooled to 10-15° C., water (8.2 L) was added and the reaction mixture was stirred for 2 days at below 25° C. The slurry was filtered and the wet-cake was washed with water (2×0.8 L), n-heptane (2×0.8 L) and dried overnight under vacuum at 60-65° C. to obtain tert-butyl 4-bromo-2-(1H-pyrrolo[2,3-b]pyridine-5-yloxy)benzoate (246 g, 87%).
Step 2—Preparation of Compound 5
In a 10-L reactor equipped with mechanical stirrer, thermometer and condenser, charged tert-butyl 4-bromo-2-(1H-pyrrolo[2,3-b]pyridine-5-yloxy)benzoate (compound 6b, 235 g, 0.6 mol) and THF (5.6 L). The mixture was stirred at 20-25° C. for ~15 minutes (until complete dissolution). The solution treated with NaOtBu (162.5 g, 1.7 mol, 2.8 equiv) and water (282 ml). The reaction mixture was heated and stirred overnight at 60-65° C. then NaOtBu (162.5 g, 1.7 mol, 2.8 equiv) was added. The reaction mixture was stirred overnight at 60-65° C. then NaOtBu (81.25 g, 0.85 mol, 1.4 equiv) was added. The reaction mixture was stirred for 5 h at 60-65° C. then NaOtBu (81.25 g, 0.85 mol, 1.4 equiv) was added. The reaction mixture was stirred overnight at 60-65° C. then water (4.7 L) was added. The reaction mixture cooled to below 25° C. and acidified to pH 2-3 using aqueous sulfuric acid. After THF was removed in vacuum the reaction mixture was stirred overnight at below 25° C. The slurry was filtered and the wet-cake was washed with water (2×0.78 L), n-heptane (2×0.78 L) and dried under vacuum at 60-65° C. for 26 h to obtain desired compound (206 g, 102%; THF: 5.2%).
B. Procedure 2
In a 15-L reactor equipped with mechanical stirrer, thermometer and condenser, charged 5-hydroxy-7-azaindole (compound 8, 115 g, 0.86 mol), methyl 4-bromo-2-fluorobenzoate (compound 7c, 200 g, 0.86 mol), N,N-dimethylformamide (1.4 L) and acetonitrile (1.4 L). The mixture was stirred at 20-25° C. for ~15 minutes (until complete dissolution). The solution treated with $K_3PO_4$ (255 g, 1.20 mol, 1.4 equiv) at 20-25° C. The reaction mixture (suspension) was heated and stirred for 26 h at 90-95° C. then cooled to 60-65° C. and 10% aqueous NaOH (3.2 L) was added. The reaction mixture was stirred for 30 min at 90-95° C. then cooled to below 25° C. and acidified to pH 2-3 using aqueous sulfuric acid. After acetonitrile was removed in vacuum water (12 L) was added and the reaction mixture was stirred overnight at below 25° C. The slurry was filtered and the wet-cake was washed with water (2×0.8 L), n-heptane (2×0.8 L) and dried under vacuum at 60-65° C. for 26 h to obtain desired compound (278 g, 97%).

Example 20. Preparation of Compound 4

In a 2-L reactor equipped with mechanical stirrer, charged 1-[[2-(4-chlorophenyl)-4,4-dimethylcyclohex-1-enyl]methyl]piperazine bis-hydrochloride (1:2) (compound 9, 130 g, 0.33 mol), toluene (0.87 L) and 20% aqueous $K_3PO_4$ (0.87 L). The mixture was stirred at 20-25° C. for ~15 minutes (until complete dissolution). After phase separation the organic layer was extracted with 25% aqueous NaCl. After phase separation the organic layer was concentrated in vacuum, the residue was diluted with toluene (0.29 L) and evaporated to dryness. The residue dissolved in toluene (0.29 L) and stored at below 0° C.

Example 21. Preparation of Compound 2

In a 500-mL three necked round bottom flask equipped with magnetic stirrer, thermometer, condenser, charged 4-bromo-2-(1H-pyrrolo[2,3-b]pyridine-5-yloxy)benzoic acid (8.67 g, 26 mmol), (4-(N,N-dimethylamino)phenyl)-di-tert-butyl-phosphine (APhos®, 895 mg, 0.78 mmol, 0.13 equiv), tris(dibenzylideneacetone)-dipalladium(0) (1.54 g, 1.69 mmol, 0.065 equiv), THF (87 mL) and 1-[[2-(4-chlorophenyl)-4,4-dimethylcyclohex-1-enyl]methyl]piperazine in toluene (31.2 g, 29 mmol, 1.12 equiv). The reaction mixture was stirred under inert atmosphere, 1.5 M lithium bis(trimethylsilyl)amide in THF (74 mL, 112 mmol, 4.3 equiv) was added, and heated to 55-56° C. The reaction mixture was stirred at 55-56° C. for 30 min then quenched by addition of cold (2-8° C.) 12% aqueous NaCl (347 mL).

After phase separation the organic layer was filtered and concentrated in vacuum to ~⅓ volume. The residue was added to a cold (0-5° C.) suspension of perlite (22 g) in n-heptane (364 mL). The suspension was stirred for 1 hour at 0-5° C. then filtered. The wet-cake was washed with n-heptane (3×87 mL), and dried under vacuum at 20-25° C. for 2 hours. The solid was suspended in THF (87 mL), filtered and the wet cake was washed with THF (4×87 mL). HPLC-analysis of the combined THF solution comprised 8.3 g of VNT-08 content (yield: 56%).

Example 22. Preparation of Compound 2a

In a 500-mL three necked round bottom flask equipped with magnetic stirrer, thermometer, condenser, charged 150 mL of 2-[(1H-Pyrrolo[2,3-b]pyridine-5-yl)oxy]-4-[4-[[2-(4-chlorophenyl)-4,4-dimethylcyclohex-1-enyl]methyl]piperazin-1-yl]benzoic acid in THF (assay: 12 g, 21 mmol), heated up to 50-55° C. and 3.36 mL (63 mmol) sulfuric acid in THF (23.5 mL) was added. The reaction mixture was stirred for 30 min at 50-55° C. and n-heptane (300 mL) was added dropwise at this temperature. The reaction mixture was cooled to 0-5° C., stirred for 30 min and filtered. The wet cake was washed with n-heptane (30 mL) and dried under vacuum at 40-45° C. overnight to obtain desired compound (assay: 11 g, 92%, sulfate: 14.5%).

Example 23. Preparation of Compound 2b

In a 100-mL three necked round bottom flask equipped with magnetic stirrer, thermometer, condenser, charged 15 mL of 2-[(1H-Pyrrolo[2,3-b]pyridine-5-yl)oxy]-4-[4-[[2-(4-chlorophenyl)-4,4-dimethylcyclohex-1-enyl]methyl]piperazin-1-yl]benzoic acid in THF (assay: 1 g, 1.75 mmol), heated up to 50-55° C. and 0.4 mL (5.25 mmol) trifluoroacetic acid in THF (2 mL) was added. The reaction mixture was stirred for 30 min at 50-55° C. and n-heptane (25 mL) was added dropwise at this temperature. The reaction mixture was cooled to 0-5° C., stirred for 30 min and filtered. The wet cake was washed with n-heptane (2.5 mL) and dried under vacuum at 40-45° C. overnight to obtain desired compound (assay: 0.85 g, 85%, TFA: 14.8%).

Example 24. Preparation of Compound 3

In a 10-L reactor equipped with mechanical stirrer, thermometer and condenser, 4-fluoro-3-nitrobenzenesulfonamide (160 g, 0.73 mmol) was dissolved in 2-propanol (4.8 L) at 55-60° C. To this solution Na$_2$CO$_3$ (46.2 g, 0.44 mol, 0.6 equiv), 4-aminomethyltetrahydropyran (125.5 g, 1.09 mol, 1.5 equiv) were added and reaction mixture was stirred for 4 h at 55-65° C. The reaction mixture was diluted with water (4.8 L), cooled to 20-30° C. and stirred overnight at 20-30° C. The slurry was filtered, the wet-cake was washed with water (5×0.8 L), and dried under vacuum at 90-95° C. for 2 days to obtain desired compound (216.5 g, 94%).

Example 25. Preparation of Form Alpha of Compound 5

In a 100-mL flask (I) 4-bromo-2-(1H-pyrrolo[2,3-b]pyridine-5-yloxy)benzoic acid (2 g, 6 mmol) was dissolved in a mixture of DMF (4.6 mL) and EtOH (1.4 mL) at 80° C. In a 250-mL reactor (II) equipped with mechanical stirrer, thermometer and condenser, DMF (5.2 mL), EtOH (21.9 mL) and n-heptane (26.9 mL) are mixed and heated up to 80° C.

The resulting acid solution (flask I) was added into the reactor (II) at 80° C. and the mixture was cooled to 0° C. in 10 hours and stirred for 69 hours at 0° C. The slurry was filtered and the wet-cake was dried under vacuum at 60° C. overnight to obtain 1.18 g of product.

Example 26. Preparation of Form Beta of Compound 5

In a 100-mL flask (I) 4-bromo-2-(1H-pyrrolo[2,3-b]pyridine-5-yloxy)benzoic acid (2 g, 6 mmol) was dissolved in a mixture of DMF (6.2 mL) and EtOH (1.8 mL) at 80° C. In a 250-mL reactor (II) equipped with mechanical stirrer, thermometer and condenser, DMF (0.1 mL), EtOH (50.06 mL) and n-heptane (16.7 mL) are mixed and heated up to 80° C.

The resulting acid solution (flask I) was added into the reactor (II) at 80° C. and the mixture was cooled to 0° C. in 10 hours and stirred for 59 hours at 0° C. The slurry was filtered and the wet-cake was dried under vacuum for 5 hours at 20-25° C. to obtain 1.42 g of product.

The invention claimed is:

1. A process for preparing venetoclax comprising:
   a) reacting a compound of formula 5, wherein the compound of formula 5 is a solid

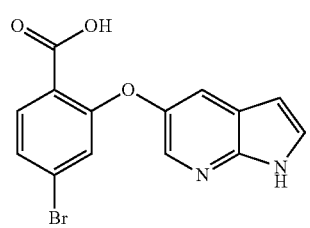

5 with a compound of formula 4

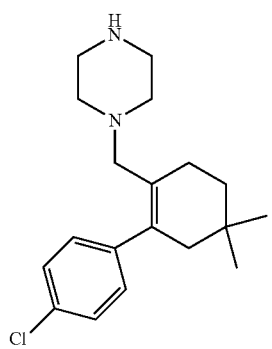

4 to provide compound of formula 2 in free base or acid salt form

2

[Structure of compound 2: benzoic acid with ortho-oxy linkage to 7-azaindole, and para-piperazine linked via methylene to a 4-chlorophenyl-dimethylcyclohexenyl group]

b) reacting the compound of formula 2 with compound of formula 3

3

[Structure of compound 3: 2-nitro-4-sulfamoyl-N-((tetrahydro-2H-pyran-4-yl)methyl)aniline]

to afford Venetoclax 1

[Structure of Venetoclax 1]

2. The process according to claim 1 wherein compound of formula 2 is an acid salt.

3. The process according to claim 1 wherein the compound of formula 5 is crystalline.

4. The process according to claim 1 wherein step a) is carried out in the presence of solvent, a base and a source of palladium and a phosphine ligand or a pre-prepared phosphine complex.

5. The process of according to claim 4 wherein the solvent is selected from a group consisting of THF, toluene, dioxane, and acetonitrile.

6. The process according to claim 4 wherein the palladium source is tris(dibenzylideneacetone)-dipalladium (0).

7. The process according to claim 4 wherein the base of step a) is LiHMDS or NaOtBu.

8. The process according to claim 1 wherein step b) is carried out in the presence of a coupling agent, an activating agent, and a base.

9. The process according to claim 8 wherein the coupling agent is selected from the group consisting of EDCI and DIC.

10. The process according to claim 8 wherein the activating agent is selected from DMAP or HOBt.

11. The process according to claim 8 wherein the base of step b) is triethylamine.

12. The process according to claim 1 wherein the compound of formula 5 is prepared by a process comprising:

i) reacting compound of formula 7a

7a

[Structure of compound 7a: alkyl 4-bromo-2-fluorobenzoate]

R = C1-C6 alkyl and compound of formula 8

8

[Structure of compound 8: 5-hydroxy-7-azaindole]

to obtain the compound of formula 6a

6a

[Structure of compound 6a: alkyl 4-bromo-2-((1H-pyrrolo[2,3-b]pyridin-5-yl)oxy)benzoate]

R = C1-C6 alkyl and ii) hydrolyzing the compound of formula 6a to obtain compound of formula 5.

13. The process according to claim 12 wherein step i) is carried out in the presence of a solvent and a base.

14. The process according to claim 13 wherein the solvent is DMF, acetonitrile, DMA, or combination thereof.

15. The process according to claim 13 wherein the base of step i) is $K_3PO_4$.

16. Compound of formula 5 having the formula;

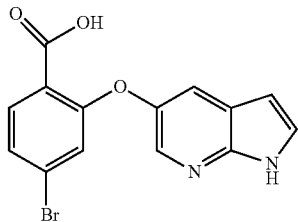

in crystalline form.

17. Compound of formula 5 according to claim 16 wherein the compound is crystalline form alpha characterized by an X-ray powder diffraction pattern having peaks at 9.8, 15.0, 19.6, 27.0 and 28.3 degrees two theta±0.2 degrees two theta.

18. A process for preparing Venetoclax comprising reacting a compound of formula 5

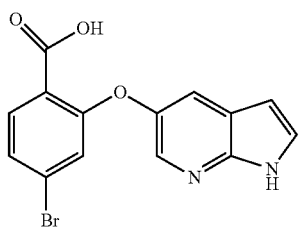

with a compound of formula 4

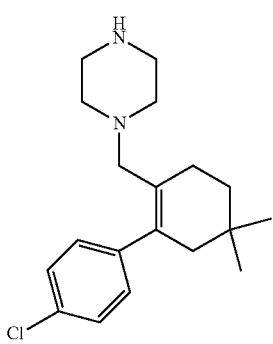

to provide compound of formula 2 in free base or acid salt form

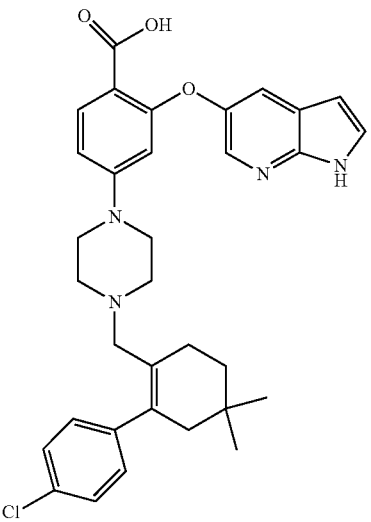

wherein the reaction is carried out in the presence of solvent, LiHMDS, and a source of palladium and a phosphine ligand or a pre-prepared phosphine complex; and reacting the compound of formula 2 with compound of formula 3

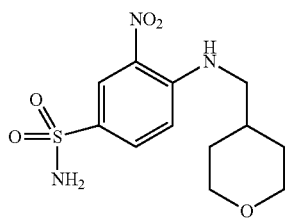

to afford Venetoclax 1

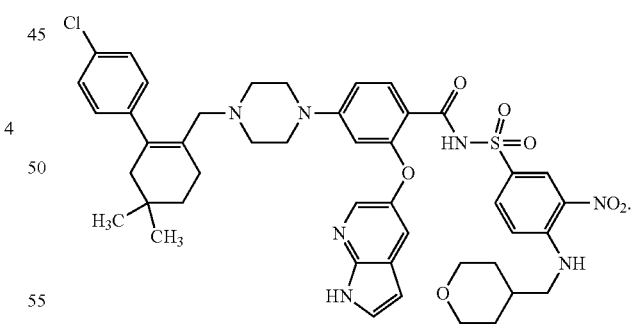

19. The process according to claim 18 wherein compound of formula 5 is crystalline.

20. Compound of formula 5 according to claim 16 wherein the compound is crystalline form beta characterized by an X-ray powder diffraction pattern having peaks at 10.1, 15.5, 17.3, 20.2 and 28.9 degrees two theta±0.2 degrees two theta.

21. The process according to claim 18 wherein compound of formula 2 is an acid salt.

22. The process of according to claim 18 wherein the solvent is selected from a group consisting of THF, toluene, dioxane, and acetonitrile.

23. The process of according to claim 18 wherein the palladium source is tris(dibenzylideneacetone)-dipalladium (0).

24. The process of according to claim 18 wherein the reacting the compound of formula 2 with compound of formula 3 is carried out in the presence of a coupling agent, an activating agent, and a base.

25. The process of according to claim 24 wherein the coupling agent is selected from the group consisting of EDCI and DIC.

26. The process of according to claim 24 wherein the activating agent is selected from DMAP or HOBt.

27. The process of according to claim 24 wherein the base is triethylamine.

28. The process of according to claim 18 wherein the compound of formula 5 is prepared by a process comprising:
i) reacting compound of formula 7a

7a

R = C1-C6 alkyl and compound of formula 8

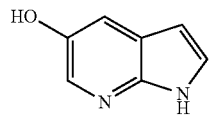

8 to obtain the compound of formula 6a

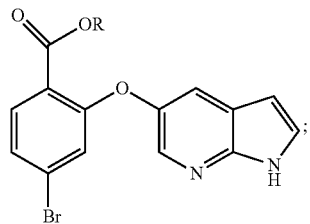

6a

R = C1-C6 alkyl and
ii) hydrolyzing the compound of formula 6a to obtain compound of formula 5.

29. The process of according to claim 28 wherein step i) is carried out in the presence of a solvent and a base.

30. The process of according to claim 29 wherein the solvent is DMF, acetonitrile, DMA, or combination thereof.

31. The process of according to claim 29 wherein the base of step i) is $K_3PO_4$.

* * * * *